US010408841B2

(12) United States Patent
Ataman-Onal et al.

(10) Patent No.: US 10,408,841 B2
(45) Date of Patent: Sep. 10, 2019

(54) MUTATED HEV POLYPEPTIDES AND THE USE THEREOF FOR ASSAYING ANTI-HEV ANTIBODIES

(71) Applicant: BIOMERIEUX, Marcy l'Etoile (FR)

(72) Inventors: Yasemin Ataman-Onal, Reyrieux (FR); Soizic Daniel, Trevoux (FR); Nadège Goutagny, Lyons (FR); Françoise Luciani, Saint-Jean des Vignes (FR)

(73) Assignee: BIOMERIEUX SA, Marcy l'Etoile (FR)

( * ) Notice: Subject to any disclaimer, the term of this patent is extended or adjusted under 35 U.S.C. 154(b) by 0 days.

(21) Appl. No.: 15/774,366

(22) PCT Filed: Nov. 29, 2016

(86) PCT No.: PCT/FR2016/053127
§ 371 (c)(1),
(2) Date: May 8, 2018

(87) PCT Pub. No.: WO2017/093649
PCT Pub. Date: Jun. 8, 2017

(65) Prior Publication Data
US 2018/0328929 A1 Nov. 15, 2018

(30) Foreign Application Priority Data
Nov. 30, 2015 (FR) ...................................... 15 61596

(51) Int. Cl.
| C12N 15/00 | (2006.01) |
| C12N 15/86 | (2006.01) |
| C12N 15/861 | (2006.01) |
| C12N 7/00 | (2006.01) |
| A61K 9/51 | (2006.01) |
| G01N 33/576 | (2006.01) |
| C07K 14/005 | (2006.01) |
| C07K 14/10 | (2006.01) |
| C07K 16/10 | (2006.01) |

(52) U.S. Cl.
CPC ......... *G01N 33/576* (2013.01); *C07K 14/005* (2013.01); *C07K 14/10* (2013.01); *C07K 16/10* (2013.01); *C12N 2770/28122* (2013.01)

(58) Field of Classification Search
CPC .......... C12N 15/86; C12N 2710/10043; C12N 2710/10052; C12N 2710/10343; C12N 2710/10352
See application file for complete search history.

(56) References Cited

FOREIGN PATENT DOCUMENTS

| EP | 2 298 793 A2 | 3/2011 |
| WO | 93/14116 A1 | 7/1993 |
| WO | 95/08632 A1 | 3/1995 |
| WO | 01/22916 A2 | 4/2001 |

OTHER PUBLICATIONS

Ellington et al., "In vitro selection of RNA molecules that bind specific ligands," Nature, Aug. 30, 1990, vol. 346, pp. 818-822.
Boersma et al., "DARPins and other repeat protein scaffolds: advances in engineering and applications," Current Opinion in Biotechnology, 2011, vol. 22, pp. 849-857.
Emerson et al., "Hepatitis E Virus," Fields Virology, 5th Ed., pp. 3047-3058.
Fields et al., "Solid phase peptide synthesis utilizing 9-fluorenylmethoxycarbonyl amino acids," Int. J. Peptide Protein Res., 1990, vol. 35, pp. 161-214.
Meng et al., "Identification and Characterization of the Neutralization Epitope(s) of the Hepatitis E Virus," Virology, 2001, vol. 288, pp. 203-211.
Merrifield, R. B., "Solid Phase Peptide Synthesis. I. The Synthesis of a Tetrapeptide," J. Am. Chem. Soc., 1963, vol. 85, pp. 2149-2154.
Riddell et al., "Identification of Immunodominant and Conformational Epitopes in the Capsid Protein of Hepatitis E Virus by Using Monoclonal Antibodies," Journal of Virology, Sep. 2000, vol. 74, No. 17, pp. 8011-8017.
Coursaget et al., "Mapping of linear B cell epitopes on open reading frames 2- and 3-encoded proteins of hepatitis E virus using synthetic peptides," FEMS Microbiology Letters, 1993, vol. 109, pp. 251-255.
Khudyakov et al., "Antigenic Domains of the Open Reading Frame 2-Encoded Protein of Hepatitis E Virus," Journal of Clinical Microbiology, vol. 37, No. 9, Sep. 1999, pp. 2863-2871.
Li et al., "Essential Elements of the Capsid Protein for Self-Assembly into Empty Virus-Like Particles of Hepatitis E Virus," Journal of Virology, Oct. 2005 vol. 79, No. 20, pp. 12999-13006.
Feb. 3, 2017 International Search Report issued in International Patent Application No. PCT/FR2016/053127.

*Primary Examiner* — Barry A Chestnut
(74) *Attorney, Agent, or Firm* — Oliff PLC

(57) ABSTRACT

Polypeptides of the p-ORF2 protein of the hepatitis E virus, including at least the amino acid sequence 394-660, numbered in relation to a p-ORF2 protein of 660 amino acids, in which the three cysteines at positions 627, 630 and 638 have been mutated or, for a p-ORF2 protein of different length, at least the amino acid sequence corresponding to amino acids 394-660 of the p-ORF2 protein of 660 amino acids, in which the three cysteines located at the three positions corresponding to positions 627, 630 and 638 of the p-ORF2 protein of 660 amino acids have been mutated. Also, methods for determining the presence of the humoral response or the titer of antibodies directed against the p-ORF2 protein using these polypeptides, and also the use thereof in the context of infection with the hepatitis E virus.

Figure 2:
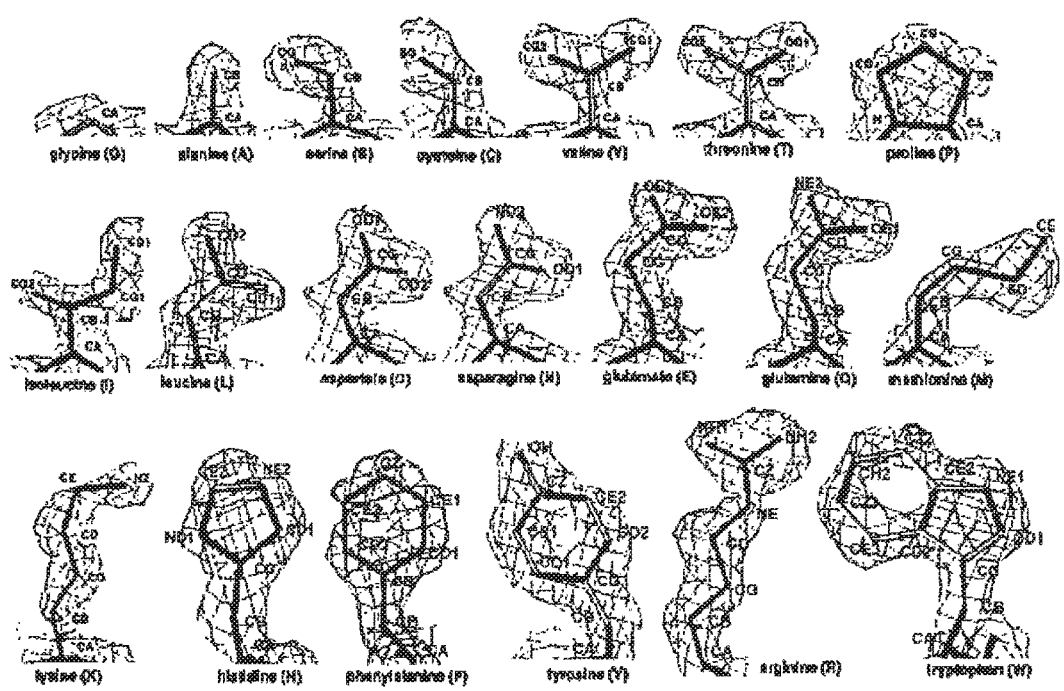

17 Claims, 23 Drawing Sheets
Specification includes a Sequence Listing.

```
Q8JJN2    Q8JJN2_HEV        1 MNNMFFCSVHGDATMRSRAFLFLFVLLPMLPAPPAGQPSGRRRGRRSGGAGGGFWGDRV  60
Q8OIR5    Q8OIR5_HEV        1 MNNMFFCSVHGDATMRSRAFLFLFVLLPMLPAPPAGQPSGRRRGRRSGGAGGGFWGDRV  60
Q806D7    Q806D7_HEV        1 MNNMFFCSVHGDATMRSRAFLFLFVLLPMLPAPPAGQPSGRRRGRRSGGAGGGFWGDRV  60
Q6BD83    Q6BD83_HEV        1 MNNMFFCSVHGDATMRSRALLFLLFVLLPMLPAPPAGQPSGRRRGRRSGGAGGGFWGDRV 60
Q6BD78    Q6BD78_HEV        1 MNNMFFCSVHGDATMRSRAFLFLFVLLPMLPAPPAGQPSGRRRGRRSGGAGGGFWGDRV  60
B6VC89    B6VC89_HEV        1 MNNMFFCSLHGDATMRSRALLFLLLLLVELPMLPAPPAGQPSGRRRGRRSGGAGSGFWGDRV 60
Q6PMR3    Q6PMR3_HEV        1 MNNMFFCSAHGDATMRSRALLFLLFLLLVFLPMLPAPPAGQPSGRRRGRRSGGAGSGFWGDRV 60
Q9IVZ8    CAPSD_HEVCT       1 MNNMFFCSVHGDATMRSRALLFLLLFLLLVFVLLPMLPAPPAGQPSGRRRGQ--AGCGGFWGDRV 58
Q8JJM1    Q8JJM1_HEV        1 ------MFFCSVHGDATMRSRALLFLLFLLLVFLPMLPAPPAGQPSGRRRGRRSGGAGGGFWGDRV 57
Q2PYP3    Q2PYP3_HEV        1 ------MFFCSVHGDATMRSRALLFLLLVFLPMLPALPAGQPSGRRRGRRSSAGGGFWGDRA 57
Q81871    CAPSD_HEVCH       1 --------------MRPRPILLLLMFLPMLPAPPPGQPSGRRRGRRSGGSGGGFWGDRV 46
P29326    CAPSD_HEVBU       1 --------------MRPRPILLLLMFLPMLPAPPPGQPSGRRRGRRSGGSGGGFWGDRV 46
Q6J8F7    CAPSD_HEVMG       1 --------------MRPRPILLLLMFLPMLPAPPAGQPSGRRRGRRNGAGGGFWGDRV 46
Q04611    CAPSD_HEVMY       1 --------------MRPRPILLLLMFLPMLPAPPAGQPSGRRRGRRSGGSGGGFWGDRV 46
Q68985    CAPSD_HEVHY       1 --------------MGPRPILLLLMFLMELPMLLAPPGQPSGRRRGRRSGGSGGGFWGDRV 46
Q9YLQ9    CAPSD_HEVUS       1 --------------MRPRPILLLLMFLPMLPAPPAGQPSGRRRGRRSGGAGGGFWGDRV 46
P33426    CAPSD_HEVPA       1 --------------MRPRPILLLLMFLPMLPAPPGQPSGRRRGRRSGGSGGGFWGDRV 46
Q9YLR2    Q9YLR2_HEV        1 --------------MRPRPILLLLMFLPMLPAPPAGQPSGRRRGRRSGAGGGFWSDRV 46
Q0QC51    Q0QC51_HEV        1 --------------MRPRPILLLLMFLPMLPAPPAGQPSGRRRGRRSGGTGGFWGDRV 46
Q69411    Q69411_HEV        1 --------------MRPRAVLLLFVLLPMLPAPPGQPSGRRRGRRSGGSGGGFWGDRV 46
A0A024D9U6 A0A024D9U6_HEV   1 --------------MRPRAVLLLFLLFVLLPMLPAPPAGQPSGRRRGRRSGGAGGGFWGDRV 46
A0A024D9R2 A0A024D9R2_HEV   1 --------------MRPRAVLLLLLFVLLPMLPAPPAGQPSGRRRGRRSGGAGGGFWGDRV 46
Q8V729    Q8V729_HEV        1 --------------MCPRAVLLLLFVLLPMLPAPPAGQPSGRRRGRRSGGAGGGFWGDRV 46
Q03500    CAPSD_HEVME       1 --------------MRPRPLLLFLLFLPMLPAPPTGQPSGRRRGRRSGGTGGGFWGDRV 46
                                          *    *    ***:*:****   * *********:   .*   ***.**.
```

Figure 1A

```
Q8JJN2      Q8JJN2_HEV      61 DSQPFALPYIHPTNPFASDIPAAAGAGARPRQPARPLGSAWRDQSQRPATSARRRSAPAG 120
Q80IR5      Q80IR5_HEV      61 DSQPFALPYIHPTNPFASDIPTAAGSGARPRQPARPLGSAWRDQSQRPAAPARRRSAPAG 120
Q806D7      Q806D7_HEV      61 DSQPFALPYIHPTNPFASDIPTAAGSGARPRQPARPLGSAWRDQSQRPAASARRRSAPAG 120
Q6BD83      Q6BD83_HEV      61 DSQPFALPYIHPTNPFASDIPAAAGAGARPRQPARPLGSAWRDQSQRPATSARRRSAPAG 120
Q6BD78      Q6BD78_HEV      61 DSQPFALPYIHPTNPFASDIPAAAGAGARPRQPARPLGSAWRDQSQRPATSARRRSAPAG 120
B6VC89      B6VC89_HEV      61 DSQPFALPYIHPTNPFASDIPAAAGAGARPRQPARPLGSAWRDQSQRPAAPARRRSAPAG 120
Q6PMR3      Q6PMR3_HEV      61 DSQPFALPYIHPTNPFASDIPAAAGAGARPRQPARPLGSAWRDQSQRPAASTRRRPAPAG 120
Q9IVZ8      CAPSD_HEVCT     59 DSQPFALPYIHPTNPFASDIPAAAGTGARPRQPIRPLGSAWRDQSQRPAASTRRRPAPAG 118
Q8JJM1      Q8JJM1_HEV      58 DSQPFALPYIHPTNPFASDIPTAAGSGARPRQPVRPLGSAWRDQSQRPAASARRRPAPAG 117
Q2PYP3      Q2PYP3_HEV      58 DSQPFALPYIHPTNPFASDIPTAAGAGARPRQPARPLGSAWRDQSQRPATSTRRRSAPVG 117
Q81871      CAPSD_HEVCH     47 DSQPFAIPYIHPTNPFAPDVTAAAGAGPRVRQPARPLGSAWRDQAQRPAAASRRRPTTAG 106
P29326      CAPSD_HEVBU     47 DSQPFAIPYIHPTNPFAPDVTAAAGAGPRVRQPARPLGSAWRDQAQRPAVASRRRPTTAG 106
Q6J8F7      CAPSD_HEVMG     47 DSQPFALPYIHPTNPFAADVVSQPGAGARPRQPPRPLGSAWRDQSQRPSTAPRRRSAPAG 106
Q04611      CAPSD_HEVMY     47 DSQPFAIPYIHPTNPFAPDVTAAAGAGPRVRQPARPLGSAWRDQAQRPAVASRRRPTTAG 106
Q68985      CAPSD_HEVHY     47 DSQPFAIPYIHPTNPFAPNVTAAAGAGPRVRQPVRPLGSAWRDQAQRPAAASRRRPTTAG 106
Q9YLQ9      CAPSD_HEVUS     47 DSQPFALPYIHPTNPFAADVVSQPGAGTRPRQPPRPLGSAWRDQSQRPSAAPRRRSAPAG 106
P33426      CAPSD_HEVPA     47 DSQPFAIPYIHPTNPFAPDVTAAAGAGPRVRQPARPLGSAWRDQAQRPAAASRRRPTTAG 106
Q9YLR2      Q9YLR2_HEV      47 DSQPFALPYIHPTNPFAADVVSQPGAGTRPRQPPRPLGSAWRDQSKRPSVAPRRRSTPAG 106
Q0QC51      Q0QC51_HEV      47 DSQPFALPYIHPTNPFASDIPTATGAGARPRQPARPLGSAWRDQSQRPAAPARRRSAPAG 106
Q69411      Q69411_HEV      47 DSQPFAIPHIHPTNPFAPDVTAAAGAGPRVRQPARPLGSAWRDQAQRPAATSRRRPTTAG 106
A0A024D9U6  A0A024D9U6_HEV  47 DSQPFALPYIHPTNPFAADVASQSGAGARPRQPPRPLGSAWRDQSQRPPAVPRRRSAPAG 106
A0A024D9R2  A0A024D9R2_HEV  47 DSQPFALPYIHPTNPFAADVVSQPGAGTRPRQPPRPLGSAWRDQSQRPSAAPRRRPAPAG 106
Q8V729      Q8V729_HEV      47 DSQPFALPYIHPTNPFAADVFSQSGAGARPRQPPRPLGSAWRDQSQRPSAAPRRRSTPAG 106
Q03500      CAPSD_HEVME     47 DSQPFAIPYIHPTNPFAPDVAAASGSGPRLRQPARPLGSTWRDQAQRPSAASRRRPATAG 106
                               ******:*:******** :: :  *:* * *** *****:****::** .  *** : .*
```

Figure 1B

```
Q8JN2      Q8JN2_HEV         121 ASPLTAVAPAPDTAPVPDVDSRGAILRRQYNLSTSPLTSTIATGTNLVLYAAPLSPLLPL 180
Q8OIR5     Q8OIR5_HEV        121 ASPLTAVAPAPDTAPVPDVDSRGAILRRQYNLSTSPLTSTIATGTNLVLYAAPLSPLLPL 180
Q806D7     Q806D7_HEV        121 ASPLTAVAPAPDTAPVPDVDSRGAILRRQYNLSTSPLTSTIATGTNLVLYAAPLSPLLPL 180
Q6BD83     Q6BD83_HEV        121 ASPLTAVAPAPDTAPVPDVDSRGAILRRQYNLSTSPLTSTIATGTNLVLYAAPLSPLLPL 180
Q6BD78     Q6BD78_HEV        121 ASPLTAVAPAPDTAPVPDVDSRGAILRRQYNLSTSPLTSTIATGTNLVLYAAPLSPLLPL 180
B6VC89     B6VC89_HEV        121 ASPLTAVAPAPDTAPVPDVDSRGAILRRQYNLSTSPLTSTIATGTNLVLYAAPLSPLLPL 180
Q6PMR3     Q6PMR3_HEV        121 ASPLTAVAPAPDTAPVPDVDSRGAILRRQYNLSTSPLTSTIATGTNLVLYAAPLSPLLPL 180
Q9IVZ8     CAPSD_HEVCT       119 ASPLTAVAPAPDTAPVPDADSRGAILRRQYNLSTSPLTSTIATGNFVLYAAPLSPLLPL  178
Q8JJM1     Q8JJM1_HEV        118 ASPLTAVAPAPDTAPVPDVDSRGAILRRQYNLSTSPLTSTIATGTNLVLYAAPLSPLLPL 177
Q2PYP3     Q2PYP3_HEV        118 ASPLTAVAPAPDTAPVPDVDSRGAILRRQYNLSTSPLTSTIATGTNLVLYAAPLSPLLPL 177
Q81871     CAPSD_HEVCH       107 AAPLTAVAPAHDTPPVPDVDSRGAILRRQYNLSTSPLTSSVATGTNLVLYAAPLNPLLPL 166
P29326     CAPSD_HEVBU       107 AAPLTAVAPAHDTPPVPDVDSRGAILRRQYNLSTSPLTSSVATGTNLVLYAAPLNPLLPL 166
Q6J8F7     CAPSD_HEVMG       107 AAPLTAVAPAHDTPPVPDVDSRAAILRRQYNLSTSPLTSSVATGTNLVLYAAPLSPLLPL 166
Q04611     CAPSD_HEVMY       107 AAPLTAVSPAPDTAPVPDVDSRGAILRRQYNLSTSPLTSSVATGTNLVLYAAPLNPLLPL 166
Q68985     CAPSD_HEVHY       107 AAPLTAVSPAPDTAPVPDVDSRGAILRRQYNLSTSPLTSSVASGTNLVLYAAPLNPLLPL 166
Q9YLQ9     CAPSD_HEVUS       107 AAPLTAVAPAPDTPPVPDVDSRGAILRRQYNLSTSPLTSSVATGTNLVLYAAPLNPLLPL 166
F33426     CAPSD_HEVPA       107 AAPLTAIISPAPDTAPVPDVDSRGAILRRQYNLSTSPLTSSVATGTNLVLYAAPLSPLLPL 166
Q9YLR2     Q9YLR2_HEV        107 ASPLTAVAPAPDTAPVPDVDSRGAILRRQYNLSTSPLTSTIATGTNLVLYAAPLSPLLPL 166
Q0QC51     Q0QC51_HEV        107 AAPLTAVAPAHDTPPVPDVDSRGAILRRQYNLSTSPLTSSVASGTNLVLYAAPLNPLLPL 166
Q69411     Q69411_HEV        107 AAPLTAISPAPDTAPVPDVDSRGAILRRQYNLSTSPLTSSVASGTNLVLYAAPLNPLLPL 166
A0A024D9U6 A0A024D9U6_HEV    107 ATPLTAVSPEAPDAAPVPDVDSRGAILRRQYNLSTSPLTSSVASGTNLVLYAAPLNPLLPL 166
A0A024D9R2 A0A024D9R2_HEV    107 AAPLTATSPAPDTAPVPDVDSRGAILRRQYNLSTSPLTSSVASGTNLVLYAAPLNPLLPL 166
Q8V729     Q8V729_HEV        107 AAALTAVAPAHDTSPVPDVDSRGAILRRQYNLSTSPLTSSVASGTNLVLYAAPLNPLLPL 166
Q03500     CAPSD_HEVME       107 AAALTAVAPAHDTSPVPDVDSRGAILRRQYNLSTSPLTSSVASGTNLVLYAAPLNPPLPL 166
                                 *: ***  :* .*** *: ***** ************.*:**  :.*********:*** 
```

Figure 1C

| | | | |
|---|---|---|---|
| Q8JJN2 | Q8JJN2_HEV | 181 | QDGTNTHIMATEASNYAQYRVVRATIRYRPLVPNAVGGYAISISFWPQTTTPTSVDMNS 240 |
| Q8OIR5 | Q8OIR5_HEV | 181 | QDGTNTHIMATEASNYAQYRVVRATIRYRPLVPNAVGGYAISISFWPQTTTPTSVDMNS 240 |
| Q806D7 | Q806D7_HEV | 181 | QDGTNTHIMATEASNYAQYRVVRATIRYRPLVPNAVGGYAISISFWPQTTTPTSVDMNS 240 |
| Q6BD83 | Q6BD83_HEV | 181 | QDGTNTHIMATEASNYAQYRVVRATIRYRPLVPNAVGGYAISISFWPQTTTPTSVDMNS 240 |
| Q6BD78 | Q6BD78_HEV | 181 | QDGTNTHIMATEASNYAQYRVVRATIRYRPLVPNAVGGYAISISFWPQTTTPTSVDMNS 240 |
| B6VC89 | B6VC89_HEV | 181 | QDGTNTHIMATEASNYAQYRVVRATIRYRPLVPNAVGGYAISISFWPQTTTPTSVDMNS 240 |
| Q6PMR3 | Q6PMR3_HEV | 181 | QDGTNTHIMATEASNYAQYRVVRATIRYRPLVPNAVGGYAISISFWPQTTTPTSVDMNS 240 |
| Q9IVZ8 | CAPSD_HEVCT | 179 | QDGTNTHIMATEASNYAQYRVVRATIRYRPLVPNAVGGYAISISFWPQTTTPTSVDMNS 238 |
| Q8JJM1 | Q8JJM1_HEV | 178 | QDGTNTHIMATEASNYAQYRVVRATIRYRPLVPNAVGGYAISISFWPQTTTPTSVDMNS 237 |
| Q2PYP3 | Q2PYP3_HEV | 178 | QDGTNTHIMATEASNYAQYRVVRATIRYRPLVPNAVGGYAISISFWPQTTTPTSVDMNS 237 |
| Q81871 | CAPSD_HEVCH | 167 | QDGTNTHIMATEASNYAQYRVVRATIRYRPLVPNAVGGYAISISFWPQTTTPTSVDMNS 226 |
| P29326 | CAPSD_HEVBU | 167 | QDGTNTHIMATEASNYAQYRVVRATIRYRPLVPNAVGGYAISISFWPQTTTPTSVDMNS 226 |
| Q6C8F7 | CAPSD_HEVMG | 167 | QDGTNTHIMATEASNYAQYRVVRATIRYRPLVPNAVGGYAISISFWPQTTTPTSVDMNS 226 |
| Q04611 | CAPSD_HEVNY | 167 | QDGTNTHIMATEASNYAQYRVARATIRYRPLVPNAVGGYAISISFWPQTTTPTSVDMNS 226 |
| Q68985 | CAPSD_HEVHY | 167 | QDGTNTHIMATEASNYAQYRVVRARATIRYRPLVPNAVGGYAISISFWPQTTTPTSVDMNS 226 |
| Q9YLQ9 | CAPSD_HEVUS | 167 | QDGTNTHIMATEASNYAQYRVVRATIRYRPLVPNAVGGYAISISFWPQTTTPTSVDMNS 226 |
| P33426 | CAPSD_HEVPA | 167 | QDGTNTHIMATEASNYAQYRVVRATIRYRPLVPNAVGGYAISISFWPQTTTPTSVDMNS 226 |
| Q9YLR2 | Q9YLR2_HEV | 167 | QDGTNTHIMATEASNYAQYRVVRATIRYRPLVPNAVGGYAISISFWPQTTTPTSVDMNS 226 |
| Q0QC51 | Q0QC51_HEV | 167 | QDGTNTHIMATEASNYAQYRVVRATIRYRPLVPNAVGGYAISISFWPQTTTPTSVDMNS 226 |
| Q69411 | Q69411_HEV | 167 | QDGTNTHIMATEASNYAQYRVVRATIRYRPLVPNAVGGYAISISFWPQTTTPTSVDMNS 226 |
| A0A024D9U6 | A0A024D9U6_HEV | 167 | QDGTNTHIMATEASNYAQYRVVRATIRYRPLVPNAVGGYAISISFWPQTTTPTSVDMNS 226 |
| A0A024D9R2 | A0A024D9R2_HEV | 167 | QDGTNTHIMATEASNYAQYRVVRATIRYRPLVPNAVGGYAVSISFWPQTTTPTSVDMNS 226 |
| Q8V729 | Q8V729_HEV | 167 | QDGTNTHIMATEASNYAQYRVVRATIRYRPLVPNAVGGYAISISFWPQTTTPTSVDMNS 226 |
| Q03500 | CAPSD_HEVME | 167 | QDGTNTHIMATEASNYAQYRVVRATIRYRPLVPNAVGGYAISISFWPQTTTPTSVDMNS 226 |
| | | | ***** .:**.:  *:*************:******** |

Figure 1D

| | | | |
|---|---|---|---|
| Q8JJN2 | Q8JJN2_HEV | 241 | ITSTDVRILVQPGIASELVIPSERLHYRNQGWRSVETSGVAEEEATSGLVMLCIHGSPVN 300 |
| Q80IR5 | Q80IR5_HEV | 241 | ITSTDVRILVQPGIASELVIPSERLHYRNQGWRSVETSGVAEEEATSGLVMLCIHGSPVN 300 |
| Q806D7 | Q806D7_HEV | 241 | ITSTDVRILVQPGIASELVIPSERLHYRNQGWRSVETSGVAEEEATSGLVMLCIHGSPVN 300 |
| Q6BD83 | Q6BD83_HEV | 241 | ITSTDVRILVQPGIASELVIPSERLHYRNQGWRSVETSGVAEEEATSGLVMLCIHGSPVN 300 |
| Q6BD78 | Q6BD78_HEV | 241 | ITSTDVRILVQPGIASELVIPSERLHYRNQGWRSVETSGVAEEEATSGLVMLCIHGSPVN 300 |
| B6VC89 | B6VC89_HEV | 241 | ITSTDVRILVQPGIASELVIPSERLHYRNQGWRSVETSGVAEEEATSGLVMLCIHGSPVN 300 |
| Q6PMR3 | Q6PMR3_HEV | 241 | ITSTDVRILVQPGIASELVIPSERLHYRNQGWRSVETSGVAEEEATSGLVMLCIHGSPVN 300 |
| Q9IVZ8 | CAPSD_HEVCT | 239 | ITSTDVRILVQPGIASELVTPSERLHYRNQGWRSVETSGVAEEEATSGLVMLCIHGSPVN 298 |
| Q8JJM1 | Q8JJM1_HEV | 238 | ITSTDVRILVQSGIASELVIPSERLHYRNQGWRSVETSGVAEEEATSGLVMLCIHGSPVN 297 |
| Q2PYP3 | Q2PYP3_HEV | 238 | ITSTDVRILVQPGIASEHVIPSERLHYRNQGWRSVETSGVAEEEATSGLVMLCIHGSLVN 297 |
| Q81871 | CAPSD_HEVCH | 227 | ITSTDVRILVQPGIASELVIPSERLHYRNQGWRSVETSGVAEEEATSGLVMLCIHGSPVN 286 |
| P29326 | CAPSD_HEVBU | 227 | ITSTDVRILVQPGIASELVIPSERLHYRNQGWRSVETSGVAEEEATSGLVMLCIHGSPVN 286 |
| Q6J8F7 | CAPSD_HEVMG | 227 | ITSTDVRILVQPGIASELVIPSERLHYRNQGWRSVETTGVAEEEATSGLVMLCIHGSPVN 286 |
| Q04611 | CAPSD_HEVMY | 227 | ITSTDVRILVQPGIASELVIPSERLHYRNQGWRSVETSGVAEEEATSGLVMLCIHGSPVN 286 |
| Q68985 | CAPSD_HEVHY | 227 | ITSTDVRILVQPGIASELVIPSERLHYRNQGWRSVETTGVAEEEATSGLVMLCIHGSPVN 286 |
| Q9YLQ9 | CAPSD_HEVUS | 227 | ITSTDVRILVQPGVASELVIPSERLHYRNQGWRSVETTGVAEEEATSGLVMLCIHGSPVN 286 |
| P33426 | CAPSD_HEVPA | 227 | ITSTDVRILVQPGIASELVIPSERLHYRNQGWRSVETSGVAEEEATSGLVMLCIHGSPVN 286 |
| Q9YLR2 | Q9YLR2_HEV | 227 | ITSTDVRILVQPGIASELVIPSERLHYRNQGWRSVETSGVAEEEATSGLVMLCIHGSPVN 286 |
| Q0QC51 | Q0QC51_HEV | 227 | ITSTDVRILVQPGIASELVIPSERLHYRNQGWRSVETSGVAEEEATSGLVMLCIHGSPVN 286 |
| Q69411 | Q69411_HEV | 227 | ITSTDVRILVQPGIASELVIPSERLHYRNQGWRSVETSGVAEEEATSGLVMLCIHGSPVN 286 |
| A0A024D9U6 | A0A024D9U6_HEV | 227 | ITSTDVRILVQPGIASELVIPSERLHYRNQGWRSVETSGVAEEEATSGLVMLCIHGLPVN 286 |
| A0A024D9R2 | A0A024D9R2_HEV | 227 | ITSTDVRILVQPGIASELVIPSERLHYRNQGWRSVETSGVAEEEATSGLVMLCIHGSPVN 286 |
| Q8V729 | Q8V729_HEV | 227 | ITSTDVRILVQPGIASELVIPSERLHYRNQGWRSVETSGVAEEEATSGLVMLCIHGSPVN 286 |
| Q03500 | CAPSD_HEVME | 227 | ITSTDVRILVQPGIASELVIPSERLHYRNQGWRSVETSGVAEEEATSGLVMLCIHGSPVN 286 |
| | | | ********* *:**** * *:********:*****************:**** |

Figure 1E

```
Q8JJN2        Q8JJN2_HEV       301  SYTNTPYTGALGLLDFALELEFRNLTPGNTNTRVSRYSSSARHKLRRGPDGTAELTTTAA  360
Q8OIR5        Q8OIR5_HEV       301  SYTNTPYTGALGLLDFALELEFRNLTPGNTNTRVSRYSSSARHKLRRGPDGTAELTTTAA  360
Q806D7        Q806D7_HEV       301  SYTNTPYTGALGLLDFALELEFRNLTPGNTNTRVSRYSSSARHKLRRGPDGTAELTTTAA  360
Q6BD83        Q6BD83_HEV       301  SYTNTPYTGALGLLDFALELEFRNLTPGNTNTRVSRYSSSARHKLRRGPDGTAELTTTAA  360
Q6BD78        Q6BD78_HEV       301  SYTNTPYTGALGLLDFALELEFRNLTPGNTNTRVSRYSSSARHKLRRGPDGTAELTTTAA  360
B6VC89        B6VC89_HEV       301  SYTNTPYTGALGLLDFALELEFRNLTPGNTNTRVSRYSSSARHKLRRGPDGTAELTTTAA  360
Q6PMR3        Q6PMR3_HEV       301  SYTNTPYTGALGLLDFALELEFRNLTPGNTNTRVSRYSSSARHKLRRGPDGTVELTTTAA  360
Q9IV28        CAPSD_HEVCT      299  SYTNTPYTGALGLLDFALELEFRNLTPGNTNTRVSRYSSSARHKLRRGPDGTAELTTTAA  358
Q8JJM1        Q8JJM1_HEV       298  SVTNTPYTGALGLLDFALELEFRNLTPGNTNTRVSRYSSSARHKLRRGPDGTAELTTTAA  357
Q2PYP3        Q2PYP3_HEV       298  SVTNTPYTGALGLLDFALELEFRNLTPGNTNMRVSRHSSSARHKLRRGPDGTAELTTTAA  357
Q81871        CAPSD_HEVCH      287  SYTNTPYTGALGLLDFALELEFRNLTPGNTNTRVSRYSSSTARHRLRRGADGTAELTTTAA  346
P29326        CAPSD_HEVBU      287  SYTNTPYTGALGLLDFALELEFRNLTPGNTNTRVSRYSSSTARHRLRRGADGTAELT-TAA  346
Q6J8F7        Q6J8F7_HEV       287  SYTNTPYTGALGLLDFALELEFRNLTPGNTNTRVSRYTSSTARHRLRRGADGTAELTTTAA  346
Q04611        CAPSD_HEVMG      287  SYTNTPYTGALGLLDFALELEFRNLTPGNTNTRVSRYTSSTARHRLRRGADGTAELTTTAA  346
Q68985        CAPSD_HEVMY      287  SYTNTPYTGALGLLDFALELEFRNLTPGNTNTRVSRYTSTARHRLRRGADGTAELTTTAA  346
Q9YLQ9        CAPSD_HEVHY      287  SYTNTPYTGALGLLDFALELEFRNLTPGNTNTRVSRYTSTARHRLRRGADGTAELTTTAA  346
P33426        CAPSD_HEVUS      287  SYTNTPYTGALGLLDFALELEFRNLTPGNTNTRVSRYTSTARHRLRRGADGTAELTTTAA  346
Q9YLR2        CAPSD_HEVPA      287  SYTNTPYTGALGLLDFALELEFRNLTPGNTNTRVSRYTSTARHRLRRGADGTAELTTTAA  346
Q0QC51        Q9YLR2_HEV       287  SYTNTPYTGALGLLDFALEFEFRNLTPGNTNTRVSRYSSSARHKLRRGADGTAELTTTAA  346
Q69411        Q0QC51_HEV       287  SYTNTPYTGALGLLDFALELEFRNLTPGNTNTRVSRYTSTARHRLRRGADGTAELTTTAA  346
A0A024D9U6    Q69411_HEV       287  SYTNTPYTGALGLLDFALELEFRNLTPGNTNTRVSRYTSTARHRLRRGADGTAELTTTAA  346
A0A024D9R2    A0A024D9U6_HEV   287  SVTNTPYTGALGLLDFALELEFRNLTPGNTNTRVSRYTSTARHRLRRGADGTAELTTTAA  346
Q8V729        A0A024D9R2_HEV   287  SVTNTPYTGALGLLDFALELEFRNLTPGNTNTRVSRYTSTARHRLRRGADGTAELTTTAA  346
Q03500        Q8V729_HEV       287  SYTNTPYTGALGLLDFALELEFRNLTPGNTNTRVSRYTSTARHRLRRGADGTAELTTTAA  346
              CAPSD_HEVME      287  SYTNTPYTGALGLLDFALELEFRNLTTCNTNTRVSRYSSSTARHS-ARGADGTAELTTTAA  345
                                    *******************:******  ***.******::*****   ** .******
```

Figure 1F

| | | | |
|---|---|---|---|
| Q8JJN2 | Q8JJN2_HEV | 361 | TRFMKDLHFTGTNGVGEVGRGIALTLFNLADTLLGGLPTELISSAGGQLFYSRPVVSANG 420 |
| Q8OIR5 | Q8OIR5_HEV | 361 | TRFMKDLHFTGTNGVGEVGRGIALTLFNLADTLLGGLPTELISSAGGQLFYSRPVVSANG 420 |
| Q8O6D7 | Q8O6D7_HEV | 361 | TRFMKDLHFTGTNGVGEVGRGIALTLFNLADTLLGGLPTELISSAGGQLFYSRPVVSANG 420 |
| Q6BD83 | Q6BD83_HEV | 361 | TRFMKDLHFTGTNGVGEVGRGIALTLFNLADTLLGGLPTELISSAGGQLFYSRPVVSANG 420 |
| Q6BD78 | Q6BD78_HEV | 361 | TRFMKDLHFTGTNGVGEVGRGIALTLFNLADTLLGGLPTELISSAGGQLFYSRPVVSANG 420 |
| B6VC89 | B6VC89_HEV | 361 | TRFMKDLHFTGTNGVGEVGRGIALTLFNLADTLLGGLPTELISSAGGQLFYSRPVVSANG 420 |
| Q6PMR3 | Q6PMR3_HEV | 361 | TRFMKDLHFTGTNGVGEVGRGIALTLFNLADTLLGGLPTELISSAGGQLFYSRPVVSANG 420 |
| Q9IVZ8 | CAPSD_HEVCT | 359 | TRFMKDLHFTGTNGVGEVGRGIALTLFNLADTLLGGLPTELISSAGGQLFYSRPVVSANG 418 |
| Q8JJM1 | Q8JJM1_HEV | 358 | TRFMKDLHFTGTNGVGEVGRGIALTLFNLADTLLGGLPTELISSAGGQLFYSRPVVSANG 417 |
| Q2PYP3 | Q2PYP3_HEV | 358 | TRFMKDLHFTGTNGVGEVGRGIALTLFNLADTLLGGLPTELISSAGGQLFYSRPVVSANG 417 |
| Q81871 | CAPSD_HEVCH | 347 | TRFMKDLYFTSTNGVGEIGRGIALTLFNLADTLLGGLPTELISSAGGQLFYSRPVVSANG 406 |
| P29326 | CAPSD_HEVBU | 347 | TRFMKDLYFTSTNGVGEIGRGIALTLFNLADTLLGGLPTELISSAGGQLFYSRPVVSANG 406 |
| Q6J8F7 | CAPSD_HEVMG | 347 | TRFMKDLYFTSTNGVGEIGRGIALTLFNLADTLLGGLPTELISSAGGQLFYSRPVVSANG 406 |
| Q04611 | CAPSD_HEVMY | 347 | TRFMKDLYFTSTNGVGEIGRGIALTLFNLADTLLGGLPTELISSAGGQLFYSRPVVSANG 406 |
| Q68985 | CAPSD_HEVHY | 347 | TRFMKDLHFAGTNGVGEVGRGIALTLFNLADTLLGGLPTELISSAGGQLFYSRPVVSAHG 406 |
| Q9YLQ9 | CAPSD_HEVUS | 347 | TRFMKDLHFTGTNGVGEVGRGIALTLFNLADTLLGGLPTELISSAGGQLFYSRPVVSANG 406 |
| P33426 | CAPSD_HEVPA | 347 | TRFMKDLHFTGTNGVGEVGRGIALTLFNLADTLLGGLPTELISSAGGQLFYSRPVVSANG 406 |
| Q9YLR2 | Q9YLR2_HEV | 347 | TRFMKDLHFTGTNGVGEVGRGIALTLFNLADTLLGGLPTELISSAGGQLFYSRPVVSANG 406 |
| Q0QC51 | Q0QC51_HEV | 347 | TRFMKDLHFTGTNGVGEVGRGIALTLFNLADTLLGGLPTELISSAGGQLFYSRPVVSANG 406 |
| Q69411 | Q69411_HEV | 347 | TRFMKDLHFTGTNGVGEVGRGIALTLFNLADTLLGGLPTELISSAGGQLFYSRPVVSANG 406 |
| A0A024D9U6 | A0A024D9U6_HEV | 347 | TRFMKDLHFTGTNGVGEVGRGIALTLFNLADTLLGGLPTELISSAGGQLFYSRPVASANG 406 |
| A0A024D9R2 | A0A024D9R2_HEV | 347 | TRFMKDLHFTGTNGVGEVGRGIALTLFNLADTLLGGLPTELISSAGGQLFYSRPVVSANG 406 |
| Q8V729 | Q8V729_HEV | 347 | TRFMKDLHFTGTNGVGEVGRGIALTLFNLADTLLGGLPTELISSAGGQLFYSRPVVSANG 406 |
| Q03500 | CAPSD_HEVME | 346 | TRFMKDLHFTGLNGVGEVGRGIALTLLNLADTLLGGLPTELISSAGGQLFYSRPVVSANG 405 |

Figure 1G

```
Q8JJN2      Q8JJN2_HEV        421 EPTVKLYTSVENAQQDKGIAIPHDIDLGESRVVIQDYDNQHEQDRPTPSPAPSRPFSVLR 480
Q8OIR5      Q8OIR5_HEV        421 EPTVKLYTSVENAQQDKGIAIPHDIDLGESRVVIQDYDNQHEQDRPTPSPAPSRPFSVLR 480
Q806D7      Q806D7_HEV        421 EPTVKLYTSVENAQQDKGIAIPHDIDLGESRVVIQDYDNQHEQDRPTPSPAPSRPFSVLR 480
Q6BD83      Q6BD83_HEV        421 EPTVKLYTSVENAQQDKGIAIPHDIDLGESRVVIQDYDNQHEQDRPTPSPAPSRPFSVLR 480
Q6BD78      Q6BD78_HEV        421 EPTVKLYTSVENAQQDKGIAIPHDIDLGESRVVIQDYDNQHEQDRPTPSPAPSRPFSVLR 480
B6VC89      B6VC89_HEV        421 EPTVKLYTSVENAQQDKGIAIPHDIDLGESRVVIQDYDNQHEQDRPTPSPAPSRPFSVLR 480
Q6PMR3      Q6PMR3_HEV        421 EPTVKLYTSVENAQQDKGIAIPHDIDLGESRVVIQDYDNQHEQDRPTPSPAPSRPFSVLR 480
Q9IVZ8      CAPSD_HEVCT       419 ELTVKLYTSVENAQQDKGVAIPHDIDLGESRVVIQDYDNQHEQDRPTPSPAPSRPFSVLR 478
Q8JJM1      Q8JJM1_HEV        418 EPTVKLYTSVENAQQDKGIAIPHDIDLGESRVVIQDYDNQHEQDRPTPSPAPSRPFSVLR 477
Q2PYP3      Q2PYP3_HEV        418 EPTVKLYTSVENAQQDKGIAIPHDIDLGESRVGIQDYDNQHEQDRPTPSPAPSRPFSVLR 477
Q81871      CAPSD_HEVCH       407 EPTVKLYTSVENAQQDKGIAIPHDIDIDLGESRVVIQDYDNQHEQDRPTPSPAPSRPFSVLR 466
P29326      CAPSD_HEVBU       407 EPTVKLYTSVENAQQDKGIAIPHDIDLGESRVVIQDYDNQHEQDRPTPSPAPSRPFSVLR 466
Q6J8F7      CAPSD_HEVMG       407 EPTVKLYTSVENAQQDKGITIPHDIDLGDSRVVIQDYDNQHEQDRPTPSPAPSRPFSVLR 466
Q04611      CAPSD_HEVMY       407 EPTVKLYTSVENAQQDKGIAIPNDIDLGESRVVIQDYDNQHEQDRPTPSPAPSRPFSVLR 466
Q68985      CAPSD_HEVHY       407 EPTVKLYTSVENAQQDKGIAIPHDIDLGESRVVIQDYDNQHEQDRPTPSPAPSRPFSVLR 466
Q9YLQ9      CAPSD_HEVUS       407 EPTVKLYTSVENAQQDKGITIPHDIDLGDSRVVIQDYDNQHEQDRPTPSPAPSRPFSVLR 466
P33426      CAPSD_HEVPA       407 EPTVKLYTSVENAQQDKGIAIPHDIDLGESRVVIQDYDNQHEQDRPTPSPAPSRPFSVLR 466
Q9YLR2      Q9YLR2_HEV        407 EPTVKLYTSVENAQQDKGIAIPHDIDLGESRVVIQDYDNQHEQDRPTPSPAPSRPFSVLR 466
Q0QC51      Q0QC51_HEV        407 EPTVKLYTSVENAQQDKGIAIPHDIDLGDSRVVIQDYDNQHEQDRPTPSPAPSRPFSVLR 466
Q69411      Q69411_HEV        407 EPTVKLYTSVENAQQDKGIAIPHDIDLGDSRVVIQDYDNQHEQDRPTPSPAPSRPFSVLR 466
A0A024D9U6  A0A024D9U6_HEV    407 EPTVKLYTSVENAQQDKGITIPHDIDLGDSRVVIQDYDNQHEQDRPTPSPAPSRPFSVLR 466
A0A024D9R2  A0A024D9R2_HEV    407 EPTVKLYTSVENAQQDKGITIPHDIDLGDSRVVIQDYDNQHEQDRPTPSPAPSRPFSVLR 466
Q8V729      Q8V729_HEV        407 EPTVKLYTSVENAQQDKGITIPHDIDLGDSRVVIQDYDNQHEQDRPTPSPAPSRPFSVLR 466
Q03500      CAPSD_HEVME       406 EPTVKLYTSVENAQQDKGVAIPHDIDLGDSRVVIQDYDNQHEQDRPTPSPAPSRPFSVLR 465
                                    * *************::::***.:*******************************
```

Figure 1H

| | | |
|---|---|---|
| Q8JJN2 | Q8JJN2_HEV | 481 ANDVLMLSLTAAEYDQTTYGSSTNPMYVSDTVTFVNVATGAQGVSRSLDWSKVTLDGRPL 540 |
| Q8OIR5 | Q8OIR5_HEV | 481 ANDVLMLSLTAAEYDQTTYGSSTNPMYVSDTVTFVNVATGAQGVSRSLDWSKVTLDGRPL 540 |
| Q806D7 | Q806D7_HEV | 481 ANDVLMLSLTAAEYDQTTYGSSTNPMYVSDTVTFVNVATGAQGVSRSLDWSKVTLDGRPL 540 |
| Q6BD83 | Q6BD83_HEV | 481 ANDVLMLSLTAAEYDQTTYGSSTNPMYVSDTVTFVNVATGAQGVSRSLDWSKVTLDGRPL 540 |
| Q6BD78 | Q6BD78_HEV | 481 ANDVLMLSLTAAEYDQTTYGSSTNPMYVSDTVTFVNVATGAQGVSRSLDWSKVTLDGRPL 540 |
| B6VC89 | B6VC89_HEV | 481 ANDVLMLSLTAAEYDQTTYGSSTNPMYVSDTVTFVNVATGAQGVSRSLDWSKVTLDGRPL 540 |
| Q6PMR3 | Q6PMR3_HEV | 481 ANDVLMLSLTAAEYDQTTYGSSTNPMYVSDTVTFVNVATGAQGVSRSLDWSKVTLDGRPL 540 |
| Q9IVZ8 | CAPSD_HEVCT | 479 ANDVLMLSLTAAEYDQTTYGSSTNPMYVSDTVTFVNVATGAQGVSRSLDWSKVTLDGRPL 538 |
| Q8JJM1 | Q8JJM1_HEV | 478 ANDVLMLSLTAAEYDQTTYGSSTNPMYVSDTVTFVNVATGAQGVSRSLDWSKVTLDGRPL 537 |
| Q2PYP3 | Q2PYP3_HEV | 478 ANDVLMLSLTAAEYDQTTYGSSTNPMYVSDTVTFVNVATGAQGVSRSLDWSKVTLDGRPL 537 |
| Q81871 | CAPSD_HEVCH | 467 ANDVLMLSLTAAEYDQSTYGSSTGPVYVSDSVTLVNVATGAQAVARSLDWTKVTLDGRSL 526 |
| P29326 | CAPSD_HEVBU | 467 ANDVLMLSLTAAEYDQSTYGSSTGPVYVSDSVTLVNVATGAQAVARSLDWTKVTLDGRPL 526 |
| Q6J8F7 | CAPSD_HEVMG | 467 ANDVLMLSLTAAEYDQSTYGSSTGPVYVSDTVTLVNVATGAQAVARSLDWTKVTLDGRPL 526 |
| Q04611 | CAPSD_HEVMY | 467 ANDVLMLSLTAAEYDQSTYGSSTAPVYVSDSVTLVNVATGAQAVARSLDWTKVTLDGRPL 526 |
| Q68985 | CAPSD_HEVHY | 467 ANDVLMLSLTAAEYDQSTYGSSTGPVYVSDSVTLVNVATGAQAVARSLDWTKVTLDGRPL 526 |
| Q9YLQ9 | CAPSD_HEVUS | 467 ANDVLWLSLTAAEYDQSTYGSSTGPVYVSDTVTLVNVATGAQAVARSLDWTKVTLDGRPL 526 |
| P33426 | CAPSD_HEVPA | 467 ANDVLMLSLTAAEYXQTTYGSSTGPVYVSDTVTLVNVATGAQAVARSLDWTKVTLDGRPL 526 |
| Q9YLR2 | Q9YLR2_HEV | 467 ANDVLMLSLTAAEYDQTTYGSSTNPMYVSDTVTFVNVATGTQGVSRSLDWSKVTLDGRPL 526 |
| Q0QC51 | Q0QC51_HEV | 467 ANDVLMLSLTAAEYDQTTYGSSTNPMYVSDTATFVNVATGAQAVARSLDWTKVTLDGRPL 526 |
| Q69411 | Q69411_HEV | 467 ANDVLMLSLTAAEYDQTTYGSSTNPMYVSDTVTLVNVATGAQAVARSLDWTKVTLDGRPL 526 |
| A0A024D9U6 | A0A024D9U6_HEV | 467 ANDVLMLSLTAAEYDQTTYGSSTNPMYVSDTVTFVNVATGAQAVARSLDWTKVTLDGRPL 526 |
| A0A024D9R2 | A0A024D9R2_HEV | 467 ANDVLMLSLTAAEYDQTTYGSSTNPMYVSDTVTFVNVATGAQAVARSLDWTKVTLDGRPL 526 |
| Q8V729 | Q8V729_HEV | 467 ANDVLMLSLTAAEYDQTTYGSSTNPMVSVDTVTFVNVATGAQAVARSLDWSKVTLDGRPL 526 |
| Q03500 | CAPSD_HEVME | 466 ANDVLMLSLTAAEYDQSTYGSSTGPVYISDSVTLVNVATGAQAVARSLDWSKVTLDGRPL 525 |
| | | *********:. *: * *  ..: * **** *::******* |

Figure 1I

| | | |
|---|---|---|
| Q8JJN2 | Q8JJN2_HEV | 541 MTIQQYSKTFFVLPLRGKLSFWEAGTTKAGYPYNYNTTASDQILIENAAGHRVCISTYTT 600 |
| Q8OIR5 | Q8OIR5_HEV | 541 TTIQQYSKTFFVLPLRGKLSFWEAGTTKAGYPYNYNTTASDQILIENAAGHRVCISTYTT 600 |
| Q806D7 | Q806D7_HEV | 541 TTIQQYSKTFFVLPLRGKLSFWEAGTTKAGYPYNYNTTASDQILIENAAGHRVCISTYTT 600 |
| Q6BD83 | Q6BD83_HEV | 541 MTIQQYSKTFFVLPLRGKLSFWEAGTTKAGYPYNYNTTASDQILIENAAGHRVCISTYTT 600 |
| Q6BD78 | Q6BD78_HEV | 541 TTIQQYSKTFFVLPLRGKLSFWEAGTTKAGYPYNYNTTASDQILIENAAGHRVCISTYTT 600 |
| B6VC89 | B6VC89_HEV | 541 TTIQQYSKTFFVLPLRGKLSFWEAGTTKAGYPYNYNTTASDQILIENAAGHRVCISTYTT 600 |
| Q6PMR3 | Q6PMR3_HEV | 541 TTIQQYSKTFFVLPLRGKLSFWEAGTTKAGYPYNYNTTASDQILIENAAGHRVCISTYTT 600 |
| Q9IVZ8 | CAPSD_HEVCT | 539 TTIQQYSKTFFVLPLRGKLSFWEAGTTKAGYPYNYNTTASDQILIENAAGHRVCISTYTT 598 |
| Q8JJM1 | Q8JJM1_HEV | 538 TTIQQYSKTFFVLPLRGKLSFWEAGTTKAGYPYNYNTTASDQILIENAAGHRVCISTYTT 597 |
| Q2PYP3 | Q2PYP3_HEV | 538 TTIQQYSKTFFVLPLRGKLSFWEAGTTKAGYPYNYNTTASDQILIENAAGHRVCISTYTT 597 |
| Q81871 | CAPSD_HEVCH | 527 STTQQYSKTFFVLPLRGKLSFWEAGTTKAGYPYNYNTTASDQLVENAAGHRVAISTYTT 586 |
| P29326 | CAPSD_HEVBU | 527 STIQQYSKTFFVLPLRGKLSFWEAGTTKAGYPYNYNTTASDQLLVENAAGHRVAISTYTT 586 |
| Q6J8F7 | CAPSD_HEVMG | 527 TTIQQYSKTFFVLPLRGKLSFWEAGTTKAGYPYNYNTTASDQILENAAGHRVAISTYTT 586 |
| Q04611 | CAPSD_HEVMY | 527 STIQQYPKTFFVLPLRGKLSFWEAGTTKAGYPYNYNTTASDQLLVENAAGHRVAISTYTT 586 |
| Q68985 | CAPSD_HEVHY | 527 STIQQYSKIFFVLPLRGKLSFWEAGTTKAGYPYNYNTTASDQLLVENAAGHRVAISTYTT 586 |
| Q9LQ9 | CAPSD_HEVUS | 527 TTIQQYSKTFFVLPLRGKLSFWEAGTTKRPGYPYNYNTTASDQILIENAAGHRVAISTYTT 586 |
| P33426 | CAPSD_HEVPA | 527 STIQQYSKTFFVLPLRGKLSFWEAGTTKAGYPYNYNTTASDQLLVENAAGHRVAISTYTT 586 |
| Q9YLR2 | Q9YLR2_HEV | 527 TTIQQYSKTFFVLPLRGKLSFWEAGTTKAGYPYNYNTTASDQILIENAAGHRVAISTYTT 586 |
| Q0QC51 | Q0QC51_HEV | 527 TTIQQYSKKFYVLPLRGKLSFWEAGTTKAGY?PYNYNTTASDQILIENAAGHRVCISTYTT 586 |
| Q69411 | Q69411_HEV | 527 STIQQYSKTFYVLPLRGKLSFWEAGTTKAGYPYNYNTAASDQILIENAAGHRVAISTYTT 586 |
| A0A024D9U6 | A0A024D9U6_HEV | 527 TTIQQYSKTFYVLPLRGKLSFWEAGTTKAGYPYNYNTTASDQILIENASGHRVAISTYTT 586 |
| A0A024D9R2 | A0A024D9R2_HEV | 527 TTIQQYSKTFYVLPLRGKLSFWEAGTTKAGYPYNYNTTASDQILIENAAGHRVAISTYTT 586 |
| Q8V729 | Q8V729_HEV | 527 TTIQQYSKTFFVLPLRGKLSFWEAGTTKAGYPYNYNTTASDQILIENAAGHRVAISTYTT 586 |
| Q03500 | CAPSD_HEVME | 526 PTVEQYSKTFFVLPLRGKLSFWEAGTTKAGYPYNYNTTASDQILIENAAGHRVAISTYTT 585 |
| | | * :** * *::********* ********* *:.::***.:* *** |

Figure 1J

| | | |
|---|---|---|
| Q8JJN2 | Q8JJN2_HEV | 601 NLGSGPVSISAVGVLAPHSALAALEDTVDYPARAHTFDDFCPECRALGLQGCAFQSTVAE 660 |
| Q8OIR5 | Q8OIR5_HEV | 601 NLGSGPVSISSVGVLAPHSALAALEDTVDYPARAHTFDDFCPECRTLGLQGCAFQSTVAE 660 |
| Q806D7 | Q806D7_HEV | 601 NLGSGPVSISAVGVLAPHSALAALEDTVDYPARAHTFDDFCPECRTLGLQGCAFQSTVAE 660 |
| Q6BD83 | Q6BD83_HEV | 601 NLGSGPVSISAVGVLAPHSALAALEDTVDYPARAHTFDDFCPECRALGLQGCAFQSTVAE 660 |
| Q6BD78 | Q6BD78_HEV | 601 NLGSGPVSISAVGVLAPHSALAALEDTVDYPARAHTFDDFCPECRALGLQGCAFQSTVAE 660 |
| B6VC89 | B6VC89_HEV | 601 NLGSGPVSISAVGVLAPHSALAVLEDTVDYPARAHTFDDFCPECRALGLQGCAFQSTVAE 660 |
| Q6PMR3 | Q6PMR3_HEV | 601 NLGSGPVSISAVGVLAPHSALAILEDTADYPARAHTFDDFCPECRSLGLQGCAFQSTVAE 660 |
| Q9IVZ8 | CAPSD_HEVCT | 599 NLGSGPVSVSAVGVLAPHSALAALEDTADYPARAHTFDDFCPECRALGLQGCAFQSTVGE 658 |
| Q8JJM1 | Q8JJM1_HEV | 598 NLGSGPVSISAVGVLAPHSALAVLEDTVDYPARAHTFDDFCPECRTLGLQGCAFQSTVAE 657 |
| Q2PYP3 | Q2PYP3_HEV | 598 NLGSGPVSISAVGVLAPHSALAVLEDTVDYPARAHTFDDFCPECRALGLQGCAFQSTVAE 657 |
| Q81871 | CAPSD_HEVCH | 587 SLGAGPVSISAVAVLAPHSALALLEDTMDYPARAHTFDDFCPECRPLGLQGCAFQSTVAE 646 |
| P29326 | CAPSD_HEVBU | 587 SLGAGPVSISAVAVLAPHSALALLEDTMDYPARAHTFDDFCPECRPLGLQGCAFQSTVAE 646 |
| Q6J8F7 | CAPSD_HEVMG | 587 SLGAGPVSISAVAVLGPHSALAVLEDTLDYPACAHTFDDFCPECRPLGLQGCAFQSTVAE 646 |
| Q04611 | CAPSD_HEVMY | 587 SLGAGPVSISAVAVLAPHSALAVLEDTLDYPARAHTFDDFCPECRTLGLQGCAFQSTIAE 646 |
| Q68985 | CAPSD_HEVHY | 587 SLGAGPVSISAVAVLAPHSALAVLEDTLDYPARAHTFDDFCPECRTLGLQGCAFQSTVAE 646 |
| Q9YLQ9 | CAPSD_HEVUS | 587 SLGAGPVSISAVAVLAPHSVLALLEDTIDYPARAHTFDDFCPECRPLGLQGCAFQSTIAE 646 |
| P33426 | CAPSD_HEVPA | 587 SLGAGPVSISAVAVLAPHSALAVLEDTVDYPARAHTFDDFCPECRPLGLQGCAFQSTVAE 646 |
| Q9YLR2 | Q9YLR2_HEV | 587 NLGSGPVSISAVGVLAPHSALAVLEDTVDYPARAHTFDDFCPECRALGLQGCAFQSTVAE 646 |
| Q0QC51 | Q0QC51_HEV | 587 SLGAGPVAISAVAVLAPHSALALLEDTMDYPARAHTFDDFCPECRPLGLQGCAFQSTVAE 646 |
| Q69411 | Q69411_HEV | 587 SLGASPTSISAVGVLAPHSALAVLEDTVDYPARAHTFDDFCPECRTLGLQGCAFQSTIAE 646 |
| A0A024D9U6 | A0A024D9U6_HEV | 587 SLGAGPTSISAVGVLAPHSALAVLEDTIDYPARAHTFDDFCPECRTLGLQGCAFQSTIAE 646 |
| A0A024D9R2 | A0A024D9R2_HEV | 587 SLGAGPTSISAVGVLAPHSALAVLEDTVDYPARAHTFDDFCPECRALGLQGCAFQSTVAE 646 |
| Q8V729 | Q8V729_HEV | 587 SLGAGPTSISAVGVLAPHSALAVLEDTVDYPARAHTFDDFCPECRALGLQGCAFQSTVAE 646 |
| Q03500 | CAPSD_HEVME | 586 RLGAGPVAISAAAVLAPRSALALLEDTFDYPGRAHTFDDFCPECRALGLQGCAFQSTVAE 645 |
| | | **:.*.::..**.*:.* :*.**********:: ******:*:. * |

Figure 1K

| | | | | | |
|---|---|---|---|---|---|
| Q8JJN2 | Q8JJN2_HEV | 661 | LQRLKMKVGKTREY | 674 | SEQ ID N°1 |
| Q80IR5 | Q80IR5_HEV | 661 | LQRLKMKVGKTREY | 674 | SEQ ID N°2 |
| Q806D7 | Q806D7_HEV | 661 | LQRLKMKVGKTREY | 674 | SEQ ID N°3 |
| Q6BD83 | Q6BD83_HEV | 661 | LQRLKMKVGKTREY | 674 | SEQ ID N°4 |
| Q6BD78 | Q6BD78_HEV | 661 | LQRLKMKVGKTREY | 674 | SEQ ID N°5 |
| B6VC89 | B6VC89_HEV | 661 | LQRLKMKVGKTREY | 674 | SEQ ID N°6 |
| Q6PMR3 | Q6PMR3_HEV | 661 | LQRLKMKVGKTREY | 674 | SEQ ID N°7 |
| Q9IVZ8 | CAPSD_HEVCT | 659 | LQRLKMKVGKTREY | 672 | SEQ ID N°8 |
| Q8JJM1 | Q8JJM1_HEV | 658 | LQRLKMKVGKTREY | 671 | SEQ ID N°9 |
| Q2PYP3 | Q2PYP3_HEV | 658 | LQRLKMKVGNH--- | 668 | SEQ ID N°10 |
| Q81871 | CAPSD_HEVCH | 647 | LQRLKMKVGKTREL | 660 | SEQ ID N°11 |
| P29326 | CAPSD_HEVBU | 647 | LQRLKMKVGKTREL | 660 | SEQ ID N°12 |
| Q6J8F7 | CAPSD_HEVMG | 647 | LQRLKMKVGKTRES | 660 | SEQ ID N°13 |
| Q04611 | CAPSD_HEVMY | 647 | LQRLKMKVGKTREL | 660 | SEQ ID N°14 |
| Q68985 | CAPSD_HEVHY | 647 | LQRLKMKVGKTREL | 660 | SEQ ID N°15 |
| Q9YLQ9 | CAPSD_HEVUS | 647 | LQRLKMKVGKTRES | 660 | SEQ ID N°16 |
| P33426 | CAPSD_HEVPA | 647 | LQRLKMKVGKTREL | 660 | SEQ ID N°17 |
| Q9YLR2 | Q9YLR2_HEV | 647 | LQRLKMKVGKTRES | 660 | SEQ ID N°18 |
| Q0QC51 | Q0QC51_HEV | 647 | LQRLKMKVGKTQEY | 660 | SEQ ID N°19 |
| Q69411 | Q69411_HEV | 647 | LQRLKMKVGKTREL | 660 | SEQ ID N°20 |
| A0A024D9U6 | A0A024D9U6_HEV | 647 | LQRLKMKVGKTRES | 660 | SEQ ID N°21 |
| A0A024D9R2 | A0A024D9R2_HEV | 647 | LQRLKMKVGKTRES | 660 | SEQ ID N°22 |
| Q8V729 | Q8V729_HEV | 647 | LQRLKMKVGKTRES | 660 | SEQ ID N°23 |
| Q03500 | CAPSD_HEVME | 646 | LQRLKVKVGKTREL | 659 | SEQ ID N°24 |
| | | | *****:***: | | |

Figure 1L

| | | | | |
|---|---|---|---|---|
| Q8JJN2 | Q8JJN2_HEV | 408 | QLFYSRPVVSANG | 420 |
| Q80IR5 | Q80IR5_HEV | 408 | QLFYSRPVVSANG | 420 |
| Q806D7 | Q806D7_HEV | 408 | QLFYSRPVVSANG | 420 |
| Q6BD83 | Q6BD83_HEV | 408 | QLFYSRPVVSANG | 420 |
| Q6BD78 | Q6BD78_HEV | 408 | QLFYSRPVVSANG | 420 |
| B6VC89 | B6VC89_HEV | 408 | QLFYSRPVVSANG | 420 |
| Q6PMR3 | Q6PMR3_HEV | 408 | QLFYSRPVVSANG | 420 |
| Q9IVZ8 | CAPSD_HEVCT | 406 | QLFYSRPVVSANG | 418 |
| Q8JJM1 | Q8JJM1_HEV | 405 | QLFYSRPVVSANG | 417 |
| Q2PYP3 | Q2PYP3_HEV | 405 | QLFYSRPVVSANG | 417 |
| Q81871 | CAPSD_HEVCH | 394 | QLFYSRPVVSANG | 406 |
| P29326 | CAPSD_HEVBU | 394 | QLFYSRPVVSANG | 406 |
| Q6J8F7 | CAPSD_HEVMG | 394 | QLFYSRPVVSANG | 406 |
| Q04611 | CAPSD_HEVMY | 394 | QLFYSRPVVSAHG | 406 |
| Q68985 | CAPSD_HEVHY | 394 | QLFYSRPVVSANG | 406 |
| Q9YLQ9 | CAPSD_HEVUS | 394 | QLFYSRPVVSANG | 406 |
| P33426 | CAPSD_HEVPA | 394 | QLFYSRPVVSANG | 406 |
| Q9YLR2 | Q9YLR2_HEV | 394 | QLFYSRPVVSANG | 406 |
| Q0QC51 | Q0QC51_HEV | 394 | QLFYSRPVVSANG | 406 |
| Q69411 | Q69411_HEV | 394 | QLFYSRPVVSANG | 406 |
| A0A024D9U6 | A0A024D9U6_HEV | 394 | QLFYSRPVASANG | 406 |
| A0A024D9R2 | A0A024D9R2_HEV | 394 | QLFYSRPVVSANG | 406 |
| Q8V729 | Q8V729_HEV | 394 | QLFYSRPVVSANG | 406 |
| Q03500 | CAPSD_HEVME | 393 | QLFYSRPVVSANG | 405 |
| | | | ********.**.* | |

Figure 1M

| | | |
|---|---|---|
| Q8JJN2 | Q8JJN2_HEV | 421 EPTVKLYTSVENAQQDKGIAIPHDIDLGESRVVIQDYDNQHEQDRPTPSPAPSRPFSVLR 480 |
| Q8OIR5 | Q8OIR5_HEV | 421 EPTVKLYTSVENAQQDKGIAIPHDIDLGESRVVIQDYDNQHEQDRPTPSPAPSRPFSVLR 480 |
| Q8O6D7 | Q8O6D7_HEV | 421 EPTVKLYTSVENAQQDKGIAIPHDIDLGESRVVIQDYDNQHEQDRPTPSPAPSRPFSVLR 480 |
| Q6BD83 | Q6BD83_HEV | 421 EPTVKLYTSVENAQQDKGIAIPHDIDLGESRVVIQDYDNQHEQDRPTPSPAPSRPFSVLR 480 |
| Q6BD78 | Q6BD78_HEV | 421 EPTVKLYTSVENAQQDKGIAIPHDIDLGESRVVIQDYDNQHEQDRPTPSPAPSRPFSVLR 480 |
| B6VC89 | B6VC89_HEV | 421 EPTVKLYTSVENAQQDKGIAIPHDIDLGESRVVIQDYDNQHEQDRPTPSPAPSRPFSVLR 480 |
| Q6PMR3 | Q6PMR3_HEV | 421 EPTVKLYTSVENAQQDKGIAIPHDIDLGESRVVIQDYDNQHEQDRPTPSPAPSRPFSVLR 480 |
| Q9IVZ8 | CAPSD_HEVCT | 419 ELTVKLYTSVENAQQDKGVAIPHDIDLGESRVVIQDYDNQHEQDRPTPSPAPSRPFSVLR 478 |
| Q8JJM1 | Q8JJM1_HEV | 418 EPTVKLYTSVENAQQDKGIAIPHDIDLGESRVVIQDYDNQHEQDRPTPSPAPSRPFSVLR 477 |
| Q2PYP3 | Q2PYP3_HEV | 418 EPTVKLYTSVENAQQDKGIAIPHDIDLGESRVGIQDYDNQHEQDRPTPSPAPSRPFSVLR 477 |
| Q81871 | CAPSD_HEVCH | 407 EPTVKLYTSVENAQQDKGIAIPHDIDLGESRVVIQDYDNQHEQDRPTPSPAPSRPFSVLR 466 |
| P29326 | CAPSD_HEVBU | 407 EPTVKLYTSVENAQQDKGIAIPHDIDLGDSRVVIQDYDNQHEQDRPTPSPAPSRPFSVLR 466 |
| Q6J8F7 | CAPSD_HEVMG | 407 EPTVKLYTSVENAQQDKGIAIPHDIDLGDSRVVIQDYDNQHEQDRPTPSPAPSRPFSVLR 466 |
| Q04611 | CAPSD_HEVMY | 407 EPTVKLYTSVENAQQDKGIAIPHDIDLGDSRVVIQDYDNQHEQDRPTPSPAPSRPFSVLR 466 |
| Q68985 | CAPSD_HEVHY | 407 EPTVKLYTSVENAQQDKGIAIPHDIDLGDSRVVIQDYDNQHEQDRPTPSPAPSRPFSVLR 466 |
| Q9YLQ9 | CAPSD_HEVUS | 407 EPTVKLYTSVENAQQDKGITIPHDIDLGDSRVVIQDYDNQHEQDRPTPSPAPSRPFSVLR 466 |
| P33426 | CAPSD_HEVPA | 407 EPTVKLYTSVENAQQDKGIAIPHDIDLGDSRVVIQDYDNQHEQDRPTPSPAPSRPFSVLR 466 |
| Q9YLR2 | Q9YLR2_HEV | 407 EPTVKLYTSVENAQQDKGITIPKDIDLGDSRVVIQDYDNQHEQDRPTPSPAPSRPFSVLR 466 |
| Q0QC51 | Q0QC51_HEV | 407 EPTVKLYTSVENAQQDKGIAIPHDIDLGESRVVIQDYDNQHEQDRPTPSPAPSRPFSVLR 466 |
| Q69411 | Q69411_HEV | 407 EPTVKLYTSVENAQQDKGIAIPHDIDLGDSRVVIQDYDNQHEQDRPTPSPAPSRPFSVLR 466 |
| A0A024D9U6 | A0A024D9U6_HEV | 407 EPTVKLYTSVENAQQDKGITIPHDIDLGDSRVVIQDYDNQHEQDRPTPSPAPSRPFSVLR 466 |
| A0A024D9R2 | A0A024D9R2_HEV | 407 EPTVKLYTSVENAQQDKGITIPHDIDLGDSRVVIQDYDNQHEQDRPTPSPAPSRPFSVLR 466 |
| Q8V729 | Q8V729_HEV | 407 EPTVKLYTSVENAQQDKGITIPHDIDLGDSRVVIQDYDNQHEQDRPTPSPAPSRPFSVLR 466 |
| Q03500 | CAPSD_HEVME | 406 EPTVKLYTSVENAQQDKGVAIPHDIDLGDSRVVIQDYDNQHEQDRPTPSPAPSRPFSVLR 465 |
| | | *  ******************:.******:*.****************************** |

Figure 1N

| | | |
|---|---|---|
| Q8JJN2_HEV | 481 | ANDVLWLSLTAAEYDQTTYGSSTNPMYVSDTVTFVNVATGAQGVSRSLDWSKVTLDGRPL 540 |
| Q8OIR5_HEV | 481 | ANDVLWLSLTAAEYDQTTYGSSTNPMYVSDTVTFVNVATGAQGVSRSLDWSKVTLDGRPL 540 |
| Q806D7_HEV | 481 | ANDVLWLSLTAAEYDQTTYGSSTNPMYVSDTVTFVNVATGAQGVSRSLDWSKVTLDGRPL 540 |
| Q6BD83_HEV | 481 | ANDVLWLSLTAAEYDQTTYGSSTNPMYVSDTVTFVNVATGAQGVSRSLDWSKVTLDGRPL 540 |
| Q6BD78_HEV | 481 | ANDVLWLSLTAAEYDQTTYGSSTNPMYVSDTVTFVNVATGAQGVSRSLDWSKVTLDGRPL 540 |
| B6VC89_HEV | 481 | ANDVLWLSLTAAEYDQTTYGSSTNPMYVSDTVTFVNVATGAQGVSRSLDWSKVTLDGRPL 540 |
| Q6PMR3_HEV | 481 | ANDVLWLSLTAAEYDQTTYGSSTNPMYVSDTVTFVNVATGAQGVSRSLDWSKVTLDGRPL 540 |
| Q9IV28_CAPSD_HEVCT | 479 | ANDVLWLSLTAAEYDQTTYGSSTNPMYVSDTVTFVNVATGAQGVSRSLDWSKVTLDGRPL 538 |
| Q8JJM1_HEV | 478 | ANDVLWLSLTAAEYDQTTYGSSTNPMYVSDTVTFVNVATGAQGVSRSLDWSKVTLDGRPL 537 |
| Q2PYP3_HEV | 478 | ANDVLWLSLTAAEYDQTTYGSSTNPMYVSDTVTFVNVATGAQGVSRSLDWSKVTLDGRSL 537 |
| Q81871_CAPSD_HEVCH | 467 | ANDVLWLSLTAAEYDQSTYGSSTGPVYVVSDSVTLVNVATGAQAVARSLDWTKVTLDGRPL 526 |
| P29326_CAPSD_HEVBU | 467 | ANDVLWLSLTAAEYDQSTYGSSTGPVYVVSDSVTLVNVATGAQAVARSLDWTKVTLDGRPL 526 |
| Q6J8F7_CAPSD_HEVMG | 467 | ANDVLWLSLTAAEYDQTTYGSSTAPVYVSDSVTLVNVATGAQAVARSLDWTKVTLDGRPL 526 |
| Q04611_CAPSD_HEVMY | 467 | ANDVLWLSLTAAEYDQSTYGSSTGPVYVVSDSVTLVNVATGAQAVARSLDWTKVTLDGRPL 526 |
| Q68985_CAPSD_HEVHY | 467 | ANDVLWLSLTAAEYDQSTYGSSTGPVYVVSDSVTLVTLVNVATGAQAVARSLDWTKVTLDGRPL 526 |
| Q9YLQ9_CAPSD_HEVUS | 467 | ANDVLWLSLTAAEYDQSTYGSSTGPVYVVSDSVTLVNVATGAQAVARSLDWSKVTLDGRPL 526 |
| P33426_CAPSD_HEV2A | 467 | ANDVLWLSLTAAEYXQTTYGSSTGPVYVVSDTVTLVNVATGAQAVARSLDWTKVTLDGRPL 526 |
| Q9YLR2_HEV | 467 | ANDVLWLSLTAAEYDQTTYGSSTNPMYVSDTVTLVNVATGAQAVARSLDWSKVTLDGRPL 526 |
| Q0QC51_HEV | 467 | ANDVLWLSLTAAEYDQTTYGSSTNPMYVSDTVTLVNVATGQVSRSLDWTKVTLDGRPL 526 |
| Q69411_HEV | 467 | ANDVLWLSLTVAEYDQTTYGSSTNPMYVSDTATFVNVATGAQAVARSLDWSKVTLDGRPL 526 |
| A0A024D9U6_HEV | 467 | ANDVLWLSLTAAEYDQTTYGSSTNPMYVSDTVTLVNVATGAQAVARSLDWSKVTLDGRPL

```
Q8JJN2      Q8JJN2_HEV      541 MTIQQYSKTFFVLPLRGKLSFWEAGTTKAGYPYNYNTTASDQILIENAAGHRVCISTYTT 600
Q8OIR5      Q8OIR5_HEV      541 TTIQQYSKTFFVLPLRGKLSFWEAGTTKAGYPYNYNTTASDQILIENAAGHRVCISTYTT 600
Q8O6D7      Q8O6D7_HEV      541 TTIQQYSKTFFVLPLRGKLSFWEAGTTKAGYPYNYNTTASDQILIENAAGHRVCISTYTT 600
Q6BD83      Q6BD83_HEV      541 MTIQQYSKTFFVLPLRGKLSFWEAGTTKAGYPYNYNTTASDQILIENAAGHRVCISTYTT 600
Q6BD78      Q6BD78_HEV      541 MTIQQYSKTFFVLPLRGKLSFWEAGTTKAGYPYNYNTTASDQILIENAAGHRVCISTYTT 600
B6VC89      B6VC89_HEV      541 TTIQQYSKTFFVLPLRGKLSFWEAGTTKAGYPYNYNTTASDQILIENAAGHRVCISTYTT 600
Q6PMR3      Q6PMR3_HEV      541 TTIQQYSKTFFVLPLRGKLSFWEAGTTKAGYPYNYNTTASDQILIENAAGHRVCISTYTT 600
Q9IV28      CAPSD_HEVCH     539 TTIQQYSKTFFVLPLRGKLSFWEAGTTKAGYPYNYNTTASDQILIENAAGHRVCISTYTT 598
Q8JJM1      Q8JJM1_HEV      538 TTIQQYSKTFFVLPLRGKLSFWEAGTTKAGYPYNYNTTASDQILIENAAGHRVCISTYTT 597
Q2PYP3      Q2PYP3_HEV      538 TTIQQYSKTFFVLPLRGKLSFWEAGTTKAGYPYNYNTTASDQILIENAAGHRVCISTYTT 597
Q81871      CAPSD_HEVCH     527 STTQQYSKTFFVLPLRGKLSFWEAGTTKAGYPYNYNTTASDQLLVENAAGHRVAISTYTT 586
P29326      CAPSD_HEVBU     527 STIQQYSKTFFVLPLRGKLSFWEAGTTKAGYPYNYNTTASDQLLVENAAGHRVAISTYTT 586
Q6J8F7      CAPSD_HEVMG     527 TTIQQYSKTFFVLPLRGKLSFWEAGTTKAGYPYNYNTTASDQILIENAAGHRVAISTYTT 586
Q04611      CAPSD_HEVMY     527 STIQQYPKTFFVLPLRGKLSFWEAGTTKAGYPYNYNTTASDQLLVENAAGHRVAISTYTT 586
Q68985      CAPSD_HEVHY     527 STIQQYSKIFFVLPLRGKLSFWEAGTTRPGYPYNYNTTASDQILIENAAGHRVAISTYTT 586
Q9YLQ9      CAPSD_HEVUS     527 TTIQQYSKTFFVLPLRGKLSFWEAGTTKAGYPYNYNTTASDQILIENAAGHRVAISTYTT 586
P33426      CAPSD_HEVPA     527 STIQQYSKTFFVLPLRGKLSFWEAGTTKAGYPYNYNTTASDQLLVENAAGHRVAISTYTT 586
Q9YLR2      Q9YLR2_HEV      527 TTIQQYSKKFFVLPLRGKLSFWEAGTTKAGYPYNYNTTASDQILIENAPGHRVAISTYTT 586
Q0QC51      Q0QC51_HEV      527 TTIQQYSKTFFVLPLRGKLSFWEAGTTKAGYPYNYNTTASDQILIENASGHRVAISTYTT 586
Q69411      Q69411_HEV      527 STIQQYSKTFFVLPLRGKLSFWEAGTTKAGYPYNYNTTASDQILIENAAGHRVAISTYTT 586
A0A024D9U6  A0A024D9U6_HEV  527 TTIQQYSKTFFVLPLRGKLSFWEAGTTKAGYPYNYNTTAASDQILIENAAGHRVAISTYTT 586
A0A024D9R2  A0A024D9R2_HEV  527 TTIQQYSKTFFVLPLRGKLSFWEAGTTKAGYPYNYNTTASDQILIENAAGHRVAISTYTT 586
Q8V729      Q8V729_HEV      527 TTIQQYSKTFFVLPLRGKLSFWEAGTTKAGYPYNYNTTASDQILIENAAGHRVAISTYTT 586
Q03500      CAPSD_HEVME     526 PTVEQYSKTFFVLPLRGKLSFWEAGTTKAGYPYNYNTTASDQILIENAAGHRVAISTYTT 585
                                  *  ** *:****:*************. ***************:.:*:**.***:***
```

Figure 1P

| | | |
|---|---|---|
| Q8JJN2 | Q8JJN2_HEV | 601 NLGSGPVSISAVGVLAPHSALAALEDTVDYPARAHTFDDFCPECRALGLQGCAFQSTVAE 660 |
| Q8OIR5 | Q8OIR5_HEV | 601 NLGSGPVSISSVGVLAPHSALAPHSALAALEDTVDYPARAHTFDDFCPECRTLGLQGCAFQSTVAE 660 |
| Q806D7 | Q806D7_HEV | 601 NLGSGPVSISSVGVLAPHSALAPHSALAALEDTVDYPARAHTFDDFCPECRTLGLQGCAFQSTVAE 660 |
| Q6BD83 | Q6BD83_HEV | 601 NLGSGPVSISAVGVLAPHSALAPHSALAALEDTVDYPARAHTFDDFCPECRALGLQGCAFQSTVAE 660 |
| Q6BD78 | Q6BD78_HEV | 601 NLGSGPVSISAVGVLAPHSALAPHSALAALEDTVDYPARAHTFDDFCPECRALGLQGCAFQSTVAE 660 |
| B6VC89 | B6VC89_HEV | 601 NLGSGPVSISAVGVLAPHSALAVLEDTVDYPARAHTFDDFCPECRALGLQGCAFQSTVAE 660 |
| Q6PMR3 | Q6PMR3_HEV | 601 NLGSGPVSISAVGVLAPHSALAILEDTADYPARAHTFDDFCPECRSLGLQGCAFQSTVAE 660 |
| Q9IVZ8 | CAPSD_HEVCT | 599 NLGSGPVSVSAVGVLAPHSALAILEDTADYPARAHTFDDFCPECRALGLQGCAFQSTVGE 658 |
| Q8JJM1 | Q8JJM1_HEV | 598 NLGSGPVSISAVGVLAPHSALAVLAPHSALAALEDTVDYPARAHTFDDFCPECRTLGLQGCAFQSTVAE 657 |
| Q2PYP3 | Q2PYP3_HEV | 598 NLGSGPVSISAVGVLAPHSALAVLAPHSALAVLEDTVDYPARAHTFDDFCPECRALGLQGCAFQSTV

| | | | |
|---|---|---|---|
| Q8JJN2 | Q8JJN2_HEV | 661 LQRLKMKVGKTREY 674 | SEQ ID N°28 |
| Q8IR5 | Q8IR5_HEV | 661 LQRLKMKVGKTREY 674 | SEQ ID N°29 |
| Q806D7 | Q806D7_HEV | 661 LQRLKMKVGKTREY 674 | SEQ ID N°30 |
| Q6BD83 | Q6BD83_HEV | 661 LQRLKMKVGKTREY 674 | SEQ ID N°31 |
| Q6BD78 | Q6BD78_HEV | 661 LQRLKMKVGKTREY 674 | SEQ ID N°32 |
| B6VC89 | B6VC89_HEV | 661 LQRLKMKVGKTREY 674 | SEQ ID N°33 |
| Q6PMR3 | Q6PMR3_HEV | 661 LQRLKMKVGKTREY 674 | SEQ ID N°34 |
| Q9IVZ8 | CAPSD_HEVCT | 659 LQRLKMKVGKTREY 672 | SEQ ID N°35 |
| Q8JJM1 | Q8JJM1_HEV | 658 LQRLKMKVGKTREY 671 | SEQ ID N°36 |
| Q2PYP3 | Q2PYP3_HEV | 658 LQRLKMKVGNH--- 668 | SEQ ID N°37 |
| Q81871 | CAPSD_HEVCH | 647 LQRLKMKVGKTREL 660 | SEQ ID N°26 |
| P29326 | CAPSD_HEVBU | 647 LQRLKMKVGKTREL 660 | SEQ ID N°38 |
| Q6J8F7 | CAPSD_HEVMG | 647 LQRLKMKVGKTRES 660 | SEQ ID N°39 |
| Q04611 | CAPSD_HEVMY | 647 LQRLKMKVGKTREL 660 | SEQ ID N°40 |
| Q68985 | CAPSD_HEVHY | 647 LQRLKMKVGKTRES 660 | SEQ ID N°41 |
| Q9YLQ9 | CAPSD_HEVUS | 647 LQRLKMKVGKTREL 660 | SEQ ID N°42 |
| P33426 | CAPSD_HEVPA | 647 LQRLKMKVGKTRES 660 | SEQ ID N°43 |
| Q9YLR2 | Q9YLR2_HEV | 647 LQRLKMKVGKTQEY 660 | SEQ ID N°44 |
| Q0QC51 | Q0QC51_HEV | 647 LQRLKMKVGKTREL 660 | SEQ ID N°45 |
| Q69411 | Q69411_HEV | 647 LQRLKMKVGKTRES 660 | SEQ ID N°46 |
| A0A024D9U6 | A0A024D9U6_HEV | 647 LQRLKMKVGKTRES 660 | SEQ ID N°47 |
| A0A024D9R2 | A0A024D9R2_HEV | 647 LQRLKMKVGKTRES 660 | SEQ ID N°48 |
| Q8V729 | Q8V729_HEV | 647 LQRLKMKVGKTRES 660 | SEQ ID N°49 |
| Q03500 | CAPSD_HEVME | 646 LQRLKVKVGKTREL 659 | SEQ ID N°50 |

*

A
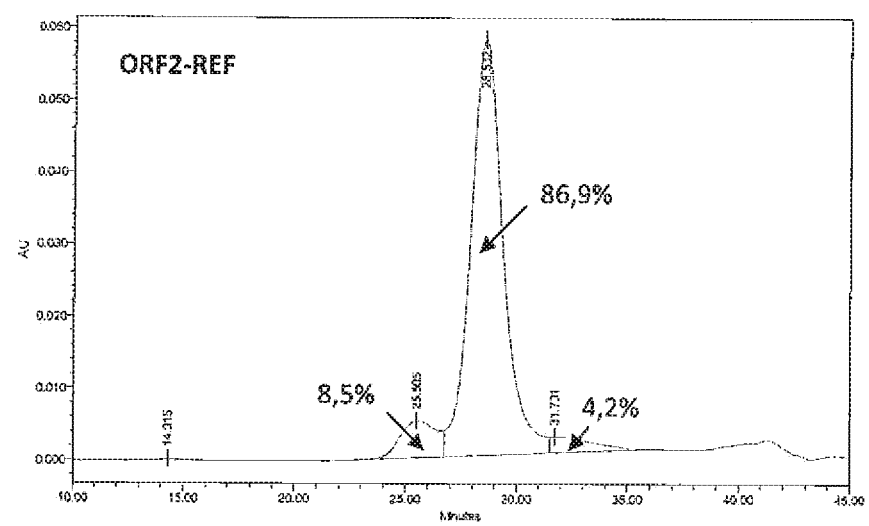
B
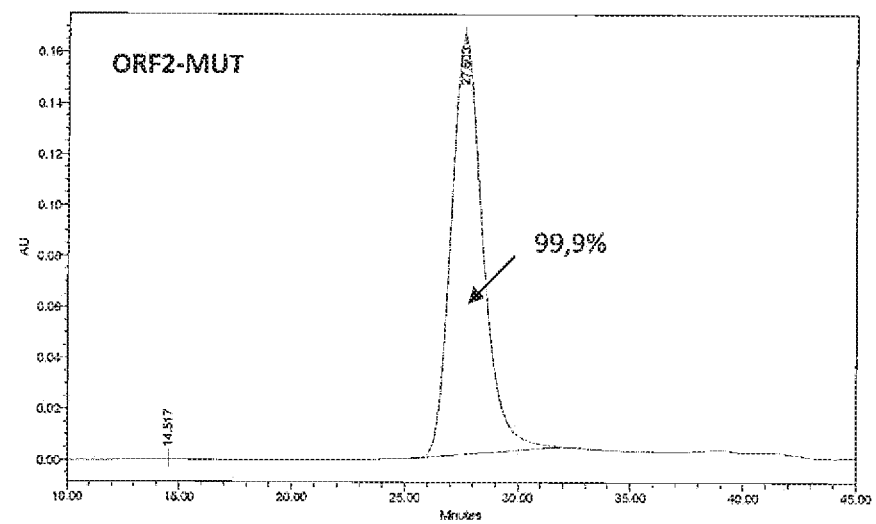
Figure 4

SEQUENCE LISTING

<160> NUMBER OF SEQ ID NOS: 50

<210> SEQ ID NO 1
<211> LENGTH: 674
<212> TYPE: PRT
<213> ORGANISM: Hepatitis E virus

<400> SEQUENCE: 1

```
Met Asn Asn Met Phe Phe Cys Ser Val His Gly Asp Ala Thr Met Arg
1               5                   10                  15

Ser Arg Ala Phe Leu Phe Leu Phe Leu Val Leu Leu Pro Met Leu Pro
            20                  25                  30

Ala Pro Pro Ala Gly Gln Pro Ser Gly Arg Arg Arg Gly Arg Arg Ser
        35                  40                  45

Gly Gly Ala Gly Gly Gly Phe Trp Gly Asp Arg Val Asp Ser Gln Pro
    50                  55                  60

Phe Ala Leu Pro Tyr Ile His Pro Thr Asn Pro Phe Ala Ser Asp Ile
65                  70                  75                  80

Pro Ala Ala Ala Gly Ala Gly Ala Arg Pro Arg Gln Pro Ala Arg Pro
                85                  90                  95

Leu Gly Ser Ala Trp Arg Asp Gln Ser Gln Arg Pro Ala Thr Ser Ala
            100                 105                 110

Arg Arg Arg Ser Ala Pro Ala Gly Ala Ser Pro Leu Thr Ala Val Ala
        115                 120                 125

Pro Ala Pro Asp Thr Ala Pro Val Pro Asp Val Asp Ser Arg Gly Ala
    130                 135                 140

Ile Leu Arg Arg Gln Tyr Asn Leu Ser Thr Ser Pro Leu Thr Ser Thr
145                 150                 155                 160

Ile Ala Thr Gly Thr Asn Leu Val Leu Tyr Ala Ala Pro Leu Ser Pro
                165                 170                 175

Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
        195                 200                 205

Arg Pro Leu Val Pro Asn Ala Val Gly Gly Tyr Ala Ile Ser Ile Ser
    210                 215                 220

Phe Trp Pro Gln Thr Thr Thr Thr Pro Thr Ser Val Asp Met Asn Ser
225                 230                 235                 240

Ile Thr Ser Thr Asp Val Arg Ile Leu Val Gln Pro Gly Ile Ala Ser
                245                 250                 255

Glu Leu Val Ile Pro Ser Glu Arg Leu His Tyr Arg Asn Gln Gly Trp
            260                 265                 270

Arg Ser Val Glu Thr Ser Gly Val Ala Glu Glu Ala Thr Ser Gly
        275                 280                 285

Leu Val Met Leu Cys Ile His Gly Ser Pro Val Asn Ser Tyr Thr Asn
    290                 295                 300

Thr Pro Tyr Thr Gly Ala Leu Gly Leu Leu Asp Phe Ala Leu Glu Leu
305                 310                 315                 320

Glu Phe Arg Asn Leu Thr Pro Gly Asn Thr Asn Thr Arg Val Ser Arg
                325                 330                 335

Tyr Ser Ser Ser Ala Arg His His Lys Leu Arg Arg Gly Pro Asp Gly Thr
            340                 345                 350

Ala Glu Leu Thr Thr Thr Ala Ala Thr Arg Phe Met Lys Asp Leu His
        355                 360                 365
```

Phe Thr Gly Thr Asn Gly Val Gly Glu Val Gly Arg Gly Ile Ala Leu
370                 375                 380

Thr Leu Phe Asn Leu Ala Asp Thr Leu Leu Gly Gly Leu Pro Thr Glu
385                 390                 395                 400

Leu Ile Ser Ser Ala Gly Gly Gln Leu Phe Tyr Ser Arg Pro Val Val
            405                 410                 415

Ser Ala Asn Gly Glu Pro Thr Val Lys Leu Tyr Thr Ser Val Glu Asn
            420                 425                 430

Ala Gln Gln Asp Lys Gly Ile Ala Ile Pro His Asp Ile Asp Leu Gly
            435                 440                 445

Glu Ser Arg Val Val Ile Gln Asp Tyr Asp Asn Gln His Glu Gln Asp
450                 455                 460

Arg Pro Thr Pro Ser Pro Ala Pro Ser Arg Pro Phe Ser Val Leu Arg
465                 470                 475                 480

Ala Asn Asp Val Leu Trp Leu Ser Leu Thr Ala Ala Glu Tyr Asp Gln
                485                 490                 495

Thr Thr Tyr Gly Ser Ser Thr Asn Pro Met Tyr Val Ser Asp Thr Val
            500                 505                 510

Thr Phe Val Asn Val Ala Thr Gly Ala Gln Gly Val Ser Arg Ser Leu
            515                 520                 525

Asp Trp Ser Lys Val Thr Leu Asp Gly Arg Pro Leu Met Thr Ile Gln
530                 535                 540

Gln Tyr Ser Lys Thr Phe Phe Val Leu Pro Leu Arg Gly Lys Leu Ser
545                 550                 555                 560

Phe Trp Glu Ala Gly Thr Thr Lys Ala Gly Tyr Pro Tyr Asn Tyr Asn
                565                 570                 575

Thr Thr Ala Ser Asp Gln Ile Leu Ile Glu Asn Ala Ala Gly His Arg
            580                 585                 590

Val Cys Ile Ser Thr Tyr Thr Thr Asn Leu Gly Ser Gly Pro Val Ser
            595                 600                 605

Ile Ser Ala Val Gly Val Leu Ala Pro His Ser Ala Leu Ala Ala Leu
610                 615                 620

Glu Asp Thr Val Asp Tyr Pro Ala Arg Ala His Thr Phe Asp Asp Phe
625                 630                 635                 640

Cys Pro Glu Cys Arg Ala Leu Gly Leu Gln Gly Cys Ala Phe Gln Ser
                645                 650                 655

Thr Val Ala Glu Leu Gln Arg Leu Lys Met Lys Val Gly Lys Thr Arg
            660                 665                 670

Glu Tyr

<210> SEQ ID NO 2
<211> LENGTH: 674
<212> TYPE: PRT
<213> ORGANISM: Hepatitis E virus

<400> SEQUENCE: 2

Met Asn Asn Met Phe Phe Cys Ser Val His Gly Asp Ala Thr Met Arg
1               5                   10                  15

Ser Arg Ala Leu Leu Phe Leu Leu Phe Val Leu Leu Pro Met Leu Pro
                20                  25                  30

Ala Pro Pro Ala Gly Gln Pro Ser Gly Arg Arg Gly Arg Arg Ser
            35                  40                  45

Gly Gly Ala Gly Gly Gly Phe Trp Gly Asp Arg Val Asp Ser Gln Pro
50                  55                  60

```
Phe Ala Leu Pro Tyr Ile His Pro Thr Asn Pro Phe Ala Ser Asp Ile
 65                  70                  75                  80

Pro Thr Ala Ala Gly Ser Gly Ala Arg Pro Gln Pro Ala Arg Pro
                 85                  90                  95

Leu Gly Ser Ala Trp Arg Asp Gln Ser Gln Arg Pro Ala Ala Pro Ala
            100                 105                 110

Arg Arg Arg Ser Ala Pro Ala Gly Ala Ser Pro Leu Thr Ala Val Ala
        115                 120                 125

Pro Ala Pro Asp Thr Ala Pro Val Pro Asp Val Asp Ser Arg Gly Ala
    130                 135                 140

Ile Leu Arg Arg Gln Tyr Asn Leu Ser Thr Ser Pro Leu Thr Ser Thr
145                 150                 155                 160

Ile Ala Thr Gly Thr Asn Leu Val Leu Tyr Ala Ala Pro Leu Ser Pro
                165                 170                 175

Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
        195                 200                 205

Arg Pro Leu Val Pro Asn Ala Val Gly Gly Tyr Ala Ile Ser Ile Ser
    210                 215                 220

Phe Trp Pro Gln Thr Thr Thr Pro Thr Ser Val Asp Met Asn Ser
225                 230                 235                 240

Ile Thr Ser Thr Asp Val Arg Ile Leu Val Gln Pro Gly Ile Ala Ser
                245                 250                 255

Glu Leu Val Ile Pro Ser Glu Arg Leu His Tyr Arg Asn Gln Gly Trp
            260                 265                 270

Arg Ser Val Glu Thr Ser Gly Val Ala Glu Glu Ala Thr Ser Gly
        275                 280                 285

Leu Val Met Leu Cys Ile His Gly Ser Pro Val Asn Ser Tyr Thr Asn
    290                 295                 300

Thr Pro Tyr Thr Gly Ala Leu Gly Leu Leu Asp Phe Ala Leu Glu Leu
305                 310                 315                 320

Glu Phe Arg Asn Leu Thr Pro Gly Asn Thr Asn Thr Arg Val Ser Arg
                325                 330                 335

Tyr Ser Ser Ser Ala Arg His Lys Leu Arg Arg Gly Pro Asp Gly Thr
            340                 345                 350

Ala Glu Leu Thr Thr Thr Ala Ala Thr Arg Phe Met Lys Asp Leu His
        355                 360                 365

Phe Thr Gly Thr Asn Gly Val Gly Glu Val Gly Arg Gly Ile Ala Leu
    370                 375                 380

Thr Leu Phe Asn Leu Ala Asp Thr Leu Leu Gly Gly Leu Pro Thr Glu
385                 390                 395                 400

Leu Ile Ser Ser Ala Gly Gly Gln Leu Phe Tyr Ser Arg Pro Val Val
                405                 410                 415

Ser Ala Asn Gly Glu Pro Thr Val Lys Leu Tyr Thr Ser Val Glu Asn
            420                 425                 430

Ala Gln Gln Asp Lys Gly Ile Ala Ile Pro His Asp Ile Asp Leu Gly
        435                 440                 445

Glu Ser Arg Val Val Ile Gln Asp Tyr Asp Asn Gln His Glu Gln Asp
    450                 455                 460

Arg Pro Thr Pro Ser Pro Ala Pro Ser Arg Pro Phe Ser Val Leu Arg
465                 470                 475                 480

Ala Asn Asp Val Leu Trp Leu Ser Leu Thr Ala Ala Glu Tyr Asp Gln
```

```
                    485                 490                 495
Thr Thr Tyr Gly Ser Ser Thr Asn Pro Met Tyr Val Ser Asp Thr Val
                500                 505                 510

Thr Phe Val Asn Val Ala Thr Gly Ala Gln Gly Val Ser Arg Ser Leu
            515                 520                 525

Asp Trp Ser Lys Val Thr Leu Asp Gly Arg Pro Leu Thr Thr Ile Gln
        530                 535                 540

Gln Tyr Ser Lys Thr Phe Phe Val Leu Pro Leu Arg Gly Lys Leu Ser
545                 550                 555                 560

Phe Trp Glu Ala Gly Thr Thr Lys Ala Gly Tyr Pro Tyr Asn Tyr Asn
                565                 570                 575

Thr Thr Ala Ser Asp Gln Ile Leu Ile Glu Asn Ala Ala Gly His Arg
            580                 585                 590

Val Cys Ile Ser Thr Tyr Thr Thr Asn Leu Gly Ser Gly Pro Val Ser
        595                 600                 605

Ile Ser Ser Val Gly Val Leu Ala Pro His Ser Ala Leu Ala Ala Leu
    610                 615                 620

Glu Asp Thr Val Asp Tyr Pro Ala Arg Ala His Thr Phe Asp Asp Phe
625                 630                 635                 640

Cys Pro Glu Cys Arg Thr Leu Gly Leu Gln Gly Cys Ala Phe Gln Ser
                645                 650                 655

Thr Val Ala Glu Leu Gln Arg Leu Lys Met Lys Val Gly Lys Thr Arg
            660                 665                 670

Glu Tyr

<210> SEQ ID NO 3
<211> LENGTH: 674
<212> TYPE: PRT
<213> ORGANISM: Hepatitis E virus

<400> SEQUENCE: 3

Met Asn

-continued

```
            180                 185                 190
Ala Ser Asn Tyr Ala Gln Tyr Arg Val Val Arg Ala Thr Ile Arg Tyr
            195                 200                 205
Arg Pro Leu Val Pro Asn Ala Val Gly Gly Tyr Ala Ile Ser Ile Ser
            210                 215                 220
Phe Trp Pro Gln Thr Thr Thr Pro Thr Ser Val Asp Met Asn Ser
225                 230                 235                 240
Ile Thr Ser Thr Asp Val Arg Ile Leu Val Gln Pro Gly Ile Ala Ser
            245                 250                 255
Glu Leu Val Ile Pro Ser Glu Arg Leu His Tyr Arg Asn Gln Gly Trp
            260                 265                 270
Arg Ser Val Glu Thr Ser Gly Val Ala Glu Glu Ala Thr Ser Gly
            275                 280                 285
Leu Val Met Leu Cys Ile His Gly Ser Pro Val Asn Ser Tyr Thr Asn
            290                 295                 300
Thr Pro Tyr Thr Gly Ala Leu Gly Leu Leu Asp Phe Ala Leu Glu Leu
305                 310                 315                 320
Glu Phe Arg Asn Leu Thr Pro Gly Asn Thr Asn Thr Arg Val Ser Arg
            325                 330                 335
Tyr Ser Ser Ala Arg His Lys Leu Arg Arg Gly Pro Asp Gly Thr
            340                 345                 350
Ala Glu Leu Thr Thr Thr Ala Ala Thr Arg Phe Met Lys Asp Leu His
            355                 360                 365
Phe Thr Gly Thr Asn Gly Val Gly Glu Val Gly Arg Gly Ile Ala Leu
            370                 375                 380
Thr Leu Phe Asn Leu Ala Asp Thr Leu Leu Gly Gly Leu Pro Thr Glu
385                 390                 395                 400
Leu Ile Ser Ser Ala Gly Gly Gln Leu Phe Tyr Ser Arg Pro Val Val
            405                 410                 415
Ser Ala Asn Gly Glu Pro Thr Val Lys Leu Tyr Thr Ser Val Glu Asn
            420                 425                 430
Ala Gln Gln Asp Lys Gly Ile Ala Ile Pro His Asp Ile Asp Leu Gly
            435                 440                 445
Glu Ser Arg Val Val Ile Gln Asp Tyr Asp Asn Gln His Glu Gln Asp
            450                 455                 460
Arg Pro Thr Pro Ser Pro Ala Pro Ser Arg Pro Phe Ser Val Leu Arg
465                 470                 475                 480
Ala Asn Asp Val Leu Trp Leu Ser Leu Thr Ala Ala Glu Tyr Asp Gln
            485                 490                 495
Thr Thr Tyr Gly Ser Ser Thr Asn Pro Met Tyr Val Ser Asp Thr Val
            500                 505                 510
Thr Phe Val Asn Val Ala Thr Gly Ala Gln Gly Val Ser Arg Ser Leu
            515                 520                 525
Asp Trp Ser Lys Val Thr Leu Asp Gly Arg Pro Leu Thr Thr Ile Gln
            530                 535                 540
Gln Tyr Ser Lys Thr Phe Phe Val Leu Pro Leu Arg Gly Lys Leu Ser
545                 550                 555                 560
Phe Trp Glu Ala Gly Thr Thr Lys Ala Gly Tyr Pro Tyr Asn Tyr Asn
            565                 570                 575
Thr Thr Ala Ser Asp Gln Ile Leu Ile Glu Asn Ala Ala Gly His Arg
            580                 585                 590
Val Cys Ile Ser Thr Tyr Thr Thr Asn Leu Gly Ser Gly Pro Val Ser
            595                 600                 605
```

```
Ile Ser Ser Val Gly Val Leu Ala Pro His Ser Ala Leu Ala Leu
    610             615                 620

Glu Asp Thr Val Asp Tyr Pro Ala Arg Ala His Thr Phe Asp Phe
625             630                 635                 640

Cys Pro Glu Cys Arg Thr Leu Gly Leu Gln Gly Cys Ala Phe Gln Ser
            645                 650                 655

Thr Val Ala Glu Leu Gln Arg Leu Lys Met Lys Val Gly Lys Thr Arg
            660                 665                 670

Glu Tyr

<210> SEQ ID NO 4
<211> LENGTH: 674
<212> TYPE: PRT
<213> ORGANISM: Hepatitis E virus

<400> SEQUENCE: 4

Met Asn Asn Met Phe Cys Ser Val His Gly Asp Ala Thr Met Arg
1               5                   10                  15

Ser Arg Ala Phe Leu Phe Leu Phe Leu Val Leu Leu Pro Met Leu Pro
                20                  25                  30

Ala Pro Pro Ala Gly Gln Pro Ser Gly Arg Arg Arg Gly Arg Arg Ser
            35                  40                  45

Gly Gly Ala Gly Gly Gly Phe Trp Gly Asp Arg Val Asp Ser Gln Pro
    50                  55                  60

Phe Ala Leu Pro Tyr Ile His Pro Thr Asn Pro Phe Ala Ser Asp Ile
65                  70                  75                  80

Pro Ala Ala Ala Gly Ala Gly Ala Arg Pro Arg Gln Pro Ala Arg Pro
                85                  90                  95

Leu Gly Ser Ala Trp Arg Asp Gln Ser Gln Arg Pro Ala Thr Ser Ala
            100                 105                 110

Arg Arg Arg Ser Ala Pro Ala Gly Ala Ser Pro Leu Thr Ala Val Ala
            115                 120                 125

Pro Ala Pro Asp Thr Ala Pro Val Pro Asp Val Asp Ser Arg Gly Ala
        130                 135                 140

Ile Leu Arg Arg Gln Tyr Asn Leu Ser Thr Ser Pro Leu Thr Ser Thr
145                 150                 155                 160

Ile Ala Thr Gly Thr Asn Leu Val Leu Tyr Ala Ala Pro Leu Ser Pro
                165                 170                 175

Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
            195                 200                 205

Arg Pro Leu Val Pro Asn Ala Val Gly Gly Tyr Ala Ile Ser Ile Ser
        210                 215                 220

Phe Trp Pro Gln Thr Thr Thr Thr Pro Thr Ser Val Asp Met Asn Ser
225                 230                 235                 240

Ile Thr Ser Thr Asp Val Arg Ile Leu Val Gln Pro Gly Ile Ala Ser
                245                 250                 255

Glu Leu Val Ile Pro Ser Glu Arg Leu His Tyr Arg Asn Gln Gly Trp
            260                 265                 270

Arg Ser Val Glu Thr Ser Gly Val Ala Glu Glu Ala Thr Ser Gly
        275                 280                 285

Leu Val Met Leu Cys Ile His Gly Ser Pro Val Asn Ser Tyr Thr Asn
290                 295                 300
```

Thr Pro Tyr Thr Gly Ala Leu Gly Leu Leu Asp Phe Ala Leu Glu Leu
305                 310                 315                 320

Glu Phe Arg Asn Leu Thr Pro Gly Asn Thr Asn Thr Arg Val Ser Arg
            325                 330                 335

Tyr Ser Ser Ser Ala Arg His Lys Leu Arg Arg Gly Pro Asp Gly Thr
        340                 345                 350

Ala Glu Leu Thr Thr Thr Ala Ala Thr Arg Phe Met Lys Asp Leu His
    355                 360                 365

Phe Thr Gly Thr Asn Gly Val Gly Glu Val Gly Arg Gly Ile Ala Leu
370                 375                 380

Thr Leu Phe Asn Leu Ala Asp Thr Leu Leu Gly Gly Leu Pro Thr Glu
385                 390                 395                 400

Leu Ile Ser Ser Ala Gly Gly Gln Leu Phe Tyr Ser Arg Pro Val Val
                405                 410                 415

Ser Ala Asn Gly Glu Pro Thr Val Lys Leu Tyr Thr Ser Val Glu Asn
                420                 425                 430

Ala Gln Gln Asp Lys Gly Ile Ala Ile Pro His Asp Ile Asp Leu Gly
            435                 440                 445

Glu Ser Arg Val Val Ile Gln Asp Tyr Asp Asn Gln His Glu Gln Asp
450                 455                 460

Arg Pro Thr Pro Ser Pro Ala Pro Ser Arg Pro Phe Ser Val Leu Arg
465                 470                 475                 480

Ala Asn Asp Val Leu Trp Leu Ser Leu Thr Ala Ala Glu Tyr Asp Gln
                485                 490                 495

Thr Thr Tyr Gly Ser Ser Thr Asn Pro Met Tyr Val Ser Asp Thr Val
            500                 505                 510

Thr Phe Val Asn Val Ala Thr Gly Ala Gln Gly Val Ser Arg Ser Leu
            515                 520                 525

Asp Trp Ser Lys Val Thr Leu Asp Gly Arg Pro Leu Met Thr Ile Gln
    530                 535                 540

Gln Tyr Ser Lys Thr Phe Phe Val Leu Pro Leu Arg Gly Lys Leu Ser
545                 550                 555                 560

Phe Trp Glu Ala Gly Thr Thr Lys Ala Gly Tyr Pro Tyr Asn Tyr Asn
                565                 570                 575

Thr Thr Ala Ser Asp Gln Ile Leu Ile Glu Asn Ala Ala Gly His Arg
            580                 585                 590

Val Cys Ile Ser Thr Tyr Thr Thr Asn Leu Gly Ser Gly Pro Val Ser
        595                 600                 605

Ile Ser Ala Val Gly Val Leu Ala Pro His Ser Ala Leu Ala Ala Leu
    610                 615                 620

Glu Asp Thr Val Asp Tyr Pro Ala Arg Ala His Thr Phe Asp Asp Phe
625                 630                 635                 640

Cys Pro Glu Cys Arg Thr Leu Gly Leu Gln Gly Cys Ala Phe Gln Ser
                645                 650                 655

Thr Val Ala Glu Leu Gln Arg Leu Lys Met Lys Val Gly Lys Thr Arg
            660                 665                 670

Glu Tyr

<210> SEQ ID NO 5
<211> LENGTH: 674
<212> TYPE: PRT
<213> ORGANISM: Hepatitis E virus

<400> SEQUENCE: 5

-continued

```
Met Asn Asn Met Phe Phe Cys Ser Val His Gly Asp Ala Thr Met Arg
1               5                   10                  15

Ser Arg Ala Phe Leu Phe Leu Phe Leu Val Leu Leu Pro Met Leu Pro
            20                  25                  30

Ala Pro Pro Ala Gly Gln Pro Ser Gly Arg Arg Gly Arg Arg Arg Ser
            35                  40                  45

Gly Gly Ala Gly Gly Gly Phe Trp Gly Asp Arg Val Asp Ser Gln Pro
        50                  55                  60

Phe Ala Leu Pro Tyr Ile His Pro Thr Asn Pro Phe Ala Ser Asp Ile
65                  70                  75                  80

Pro Ala Ala Ala Gly Ala Gly Ala Arg Pro Arg Gln Pro Ala Arg Pro
                85                  90                  95

Leu Gly Ser Ala Trp Arg Asp Gln Ser Gln Arg Pro Ala Thr Ser Ala
            100                 105                 110

Arg Arg Arg Ser Ala Pro Ala Gly Ala Ser Pro Leu Thr Ala Val Ala
            115                 120                 125

Pro Ala Pro Asp Thr Ala Pro Val Pro Asp Val Asp Ser Arg Gly Ala
        130                 135                 140

Ile Leu Arg Arg Gln Tyr Asn Leu Ser Thr Ser Pro Leu Thr Ser Thr
145                 150                 155                 160

Ile Ala Thr Gly Thr Asn Leu Val Leu Tyr Ala Ala Pro Leu Ser Pro
                165                 170                 175

Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
            195                 200                 205

Arg Pro Leu Val Pro Asn Ala Val Gly Gly Tyr Ala Ile Ser Ile Ser
        210                 215                 220

Phe Trp Pro Gln Thr Thr Thr Thr Pro Thr Ser Val Asp Met Asn Ser
225                 230                 235                 240

Ile Thr Ser Thr Asp Val Arg Ile Leu Val Gln Pro Gly Val Ala Ser
                245                 250                 255

Glu Leu Val Ile Pro Ser Glu Arg Leu His Tyr Arg Asn Gln Gly Trp
            260                 265                 270

Arg Ser Val Glu Thr Ser Gly Val Ala Glu Glu Ala Thr Ser Gly
            275                 280                 285

Leu Val Met Leu Cys Ile His Gly Ser Pro Val Asn Ser Tyr Thr Asn
290                 295                 300

Thr Pro Tyr Thr Gly Ala Leu Gly Leu Leu Asp Phe Ala Leu Glu Leu
305                 310                 315                 320

Glu Phe Arg Asn Leu Thr Pro Gly Asn Thr Asn Thr Arg Val Ser Arg
                325                 330                 335

Tyr Ser Ser Ser Ala Arg His Lys Leu Arg Arg Gly Pro Asp Gly Thr
            340                 345                 350

Ala Glu Leu Thr Thr Thr Ala Ala Thr Arg Phe Met Lys Asp Leu His
            355                 360                 365

Phe Thr Gly Thr Asn Gly Val Gly Glu Val Gly Arg Gly Ile Ala Leu
        370                 375                 380

Thr Leu Phe Asn Leu Ala Asp Thr Leu Leu Gly Gly Leu Pro Thr Glu
385                 390                 395                 400

Leu Ile Ser Ser Ala Gly Gly Gln Leu Phe Tyr Ser Arg Pro Val Val
                405                 410                 415
```

-continued

Ser Ala Asn Gly Glu Pro Thr Val Lys Leu Tyr Thr Ser Val Glu Asn
            420                 425                 430

Ala Gln Gln Asp Lys Gly Ile Ala Ile Pro His Asp Ile Asp Leu Gly
        435                 440                 445

Glu Ser Arg Val Val Ile Gln Asp Tyr Asp Asn Gln His Glu Gln Asp
    450                 455                 460

Arg Pro Thr Pro Ser Pro Ala Pro Ser Arg Pro Phe Ser Val Leu Arg
465                 470                 475                 480

Ala Asn Asp Val Leu Trp Leu Ser Leu Thr Ala Ala Glu Tyr Asp Gln
                485                 490                 495

Thr Thr Tyr Gly Ser Ser Thr Asn Pro Met Tyr Val Ser Asp Thr Val
            500                 505                 510

Thr Phe Val Asn Val Ala Thr Gly Ala Gln Gly Val Ser Arg Ser Leu
        515                 520                 525

Asp Trp Ser Lys Val Thr Leu Asp Gly Arg Pro Leu Met Thr Ile Gln
    530                 535                 540

Gln Tyr Ser Lys Thr Phe Phe Val Leu Pro Leu Arg Gly Lys Leu Ser
545                 550                 555                 560

Phe Trp Glu Ala Gly Thr Thr Lys Ala Gly Tyr Pro Tyr Asn Tyr Asn
                565                 570                 575

Thr Thr Ala Ser Asp Gln Ile Leu Ile Glu Asn Ala Ala Gly His Arg
            580                 585                 590

Val Cys Ile Ser Thr Tyr Thr Asn Leu Gly Ser Gly Pro Val Ser
        595                 600                 605

Ile Ser Ala Val Gly Val Leu Ala Pro His Ser Ala Leu Ala Ala Leu
    610                 615                 620

Glu Asp Thr Val Asp Tyr Pro Ala Arg Ala His Thr Phe Asp Asp Phe
625                 630                 635                 640

Cys Pro Glu Cys Arg Ala Leu Gly Leu Gln Gly Cys Ala Phe Gln Ser
                645                 650                 655

Thr Val Ala Glu Leu Gln Arg Leu Lys Met Lys Val Gly Lys Thr Arg
            660                 665                 670

Glu Tyr

<210> SEQ ID NO 6
<211> LENGTH: 674
<212> TYPE: PRT
<213> ORGANISM: Hepatitis E virus

<400> SEQUENCE: 6

Met Asn Asn Met Phe Phe Cys Ser Leu His Gly Asp Ala Thr Met Arg
1               5                   10                  15

Ser Arg Ala Leu Leu Phe Leu Leu Leu Leu Leu Pro Met Leu Pro
            20                  25                  30

Ala Pro Pro Ala Gly Gln Pro Ser Gly Arg Arg Arg Gly Arg Arg Ser
        35                  40                  45

Gly Gly Ala Gly Ser Gly Phe Trp Gly Asp Arg Val Asp Ser Gln Pro
    50                  55                  60

Phe Ala Leu Pro Tyr Ile His Pro Thr Asn Pro Phe Ala Ser Asp Ile
65                  70                  75                  80

Pro Ala Ala Ala Gly Ala Gly Ala Arg Pro Arg Gln Pro Ala Arg Pro
                85                  90                  95

Leu Gly Ser Ala Trp Arg Asp Gln Ser Gln Arg Pro Ala Ala Pro Ala
            100                 105                 110

```
Arg Arg Arg Ser Ala Pro Ala Gly Ala Ser Pro Leu Thr Ala Val Ala
        115                 120                 125

Pro Ala Pro Asp Thr Ala Pro Val Pro Asp Val Asp Ser Arg Gly Ala
130                 135                 140

Ile Leu Arg Arg Gln Tyr Asn Leu Ser Thr Ser Pro Leu Thr Ser Thr
145                 150                 155                 160

Ile Ala Thr Gly Thr Asn Leu Val Leu Tyr Ala Ala Pro Leu Ser Pro
                165                 170                 175

Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
        195                 200                 205

Arg Pro Leu Val Pro Asn Ala Val Gly Gly Tyr Ala Ile Ser Ile Ser
210                 215                 220

Phe Trp Pro Gln Thr Thr Thr Thr Pro Thr Ser Val Asp Met Asn Ser
225                 230                 235                 240

Ile Thr Ser Thr Asp Val Arg Ile Leu Val Gln Pro Gly Ile Ala Ser
                245                 250                 255

Glu Leu Val Ile Pro Ser Glu Arg Leu His Tyr Arg Asn Gln Gly Trp
            260                 265                 270

Arg Ser Val Glu Thr Ser Gly Val Ala Glu Glu Ala Thr Ser Gly
        275                 280                 285

Leu Val Met Leu Cys Ile His Gly Ser Pro Val Asn Ser Tyr Thr Asn
        290                 295                 300

Thr Pro Tyr Thr Gly Ala Leu Gly Leu Leu Asp Phe Ala Leu Glu Leu
305                 310                 315                 320

Glu Phe Arg Asn Leu Thr Pro Gly Asn Thr Asn Thr Arg Val Ser Arg
                325                 330                 335

Tyr Ser Ser Ser Ala Arg His Lys Leu Arg Arg Gly Ala Asp Gly Thr
            340                 345                 350

Ala Glu Leu Thr Thr Thr Ala Ala Thr Arg Phe Met Lys Asp Leu His
        355                 360                 365

Phe Thr Gly Thr Asn Gly Val Gly Glu Val Gly Arg Gly Ile Ala Leu
370                 375                 380

Thr Leu Phe Asn Leu Ala Asp Thr Leu Leu Gly Gly Leu Pro Thr Glu
385                 390                 395                 400

Leu Ile Ser Ser Ala Gly Gly Gln Leu Phe Tyr Ser Arg Pro Val Val
                405                 410                 415

Ser Ala Asn Gly Glu Pro Thr Val Lys Leu Tyr Thr Ser Val Glu Asn
            420                 425                 430

Ala Gln Gln Asp Lys Gly Ile Ala Ile Pro His Asp Ile Asp Leu Gly
        435                 440                 445

Glu Ser Arg Val Val Ile Gln Asp Tyr Asp Asn Gln His Glu Gln Asp
        450                 455                 460

Arg Pro Thr Pro Ser Pro Ala Pro Ser Arg Pro Phe Ser Val Leu Arg
465                 470                 475                 480

Ala Asn Asp Val Leu Trp Leu Ser Leu Thr Ala Ala Glu Tyr Asp Gln
                485                 490                 495

Thr Thr Tyr Gly Ser Ser Thr Asn Pro Met Tyr Val Ser Asp Thr Val
            500                 505                 510

Thr Phe Val Asn Val Ala Thr Gly Ala Gln Gly Val Ser Arg Ser Leu
        515                 520                 525

Asp Trp Ser Lys Val Thr Leu Asp Gly Arg Pro Leu Thr Thr Ile Gln
```

```
                    530                 535                 540
Gln Tyr Ser Lys Thr Phe Tyr Val Leu Pro Leu Arg Gly Lys Leu Ser
545                 550                 555                 560

Phe Trp Glu Ala Gly Thr Thr Lys Ala Gly Tyr Pro Tyr Asn Tyr Asn
                565                 570                 575

Thr Thr Ala Ser Asp Gln Ile Leu Ile Glu Asn Ala Ala Gly His Arg
                580                 585                 590

Val Cys Ile Ser Thr Tyr Thr Thr Asn Leu Gly Ser Gly Pro Val Ser
                595                 600                 605

Ile Ser Ala Val Gly Val Leu Ala Pro His Ser Ala Leu Ala Val Leu
                610                 615                 620

Glu Asp Thr Val Asp Tyr Pro Ala Arg Ala His Thr Phe Asp Asp Phe
625                 630                 635                 640

Cys Pro Glu Cys Arg Ala Leu Gly Leu Gln Gly Cys Ala Phe Gln Ser
                645                 650                 655

Thr Val Ala Glu Leu Gln Arg Leu Lys Met Lys Val Gly Lys Thr Arg
                660                 665                 670

Glu Tyr

<210> SEQ ID NO 7
<211> LENGTH: 674
<212> TYPE: PRT
<213> ORGANISM: Hepatitis E virus

<400> SEQUENCE: 7

Met Asn Asn Met Phe Phe Cys Ser Ala His Gly Asp Ala Thr Met Arg
1               5                   10                  15

Ser Arg Ala Leu Leu Phe Leu Leu Val Phe Leu Pro Met Leu Pro
            20                  25                  30

Ala Pro Pro Ala Gly Gln Pro Ser Gly Arg Arg Arg Gly Arg Ser
                35                  40                  45

Gly Gly Ala Gly Ser Gly Phe Trp Gly Asp Arg Val Asp Ser Gln Pro
    50                  55                  60

Phe Ala Leu Pro Tyr Ile His Pro Thr Asn Pro Phe Ala Ser Asp Ile
65              70                  75                  80

Pro Ala Ala Ala Gly Ala Gly Ala Arg Pro Arg Gln Pro Ala Arg Pro
                85                  90                  95

Leu Gly Ser Ala Trp Arg Asp Gln Ser Gln Arg Pro Ala Ala Ser Thr
            100                 105                 110

Arg Arg Arg Pro Ala Pro Ala Gly Ala Ser Pro Leu Thr Ala Val Ala
            115                 120                 125

Pro Ala Pro Asp Thr Ala Pro Val Pro Asp Val Asp Ser Arg Gly Ala
            130                 135                 140

Ile Leu Arg Arg Gln Tyr Asn Leu Ser Thr Ser Pro Leu Thr Ser Thr
145                 150                 155                 160

Ile Ala Thr Gly Thr Asn Leu Val Leu Tyr Ala Ala Pro Leu Ser Pro
                165                 170                 175

Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
            195                 200                 205

Arg Pro Leu Val Pro Asn Ala Val Gly Gly Tyr Ala Ile Ser Ile Ser
        210                 215                 220

Phe Trp Pro Gln Thr Thr Thr Thr Pro Thr Ser Val Asp Met Asn Ser
```

```
                225                 230                 235                 240
        Ile Thr Ser Thr Asp Val Arg Ile Leu Val Gln Pro Gly Ile Ala Ser
                        245                 250                 255
        Glu Leu Val Ile Pro Ser Glu Arg Leu His Tyr Arg Asn Gln Gly Trp
                        260                 265                 270
        Arg Ser Val Glu Thr Ser Gly Val Ala Glu Glu Ala Thr Ser Gly
                        275                 280                 285
        Leu Val Met Leu Cys Ile His Gly Ser Pro Val Asn Ser Tyr Thr Asn
                        290                 295                 300
        Thr Pro Tyr Thr Gly Ala Leu Gly Leu Leu Asp Phe Ala Leu Glu Leu
        305                 310                 315                 320
        Glu Phe Arg Asn Leu Thr Pro Gly Asn Thr Asn Thr Arg Val Ser Arg
                        325                 330                 335
        Tyr Ser Ser Ser Ala Arg His Lys Leu Arg Arg Gly Pro Asp Gly Thr
                        340                 345                 350
        Val Glu Leu Thr Thr Thr Ala Ala Thr Arg Phe Met Lys Asp Leu His
                        355                 360                 365
        Phe Thr Gly Thr Asn Gly Val Gly Glu Val Gly Arg Gly Ile Ala Leu
                        370                 375                 380
        Thr Leu Phe Asn Leu Ala Asp Thr Leu Leu Gly Gly Leu Pro Thr Glu
        385                 390                 395                 400
        Leu Ile Ser Ser Ala Gly Gly Gln Leu Phe Tyr Ser Arg Pro Val Val
                        405                 410                 415
        Ser Ala Asn Gly Glu Pro Thr Val Lys Leu Tyr Thr Ser Val Glu Asn
                        420                 425                 430
        Ala Gln Gln Asp Lys Gly Ile Ala Ile Pro His Asp Ile Asp Leu Gly
                        435                 440                 445
        Glu Ser Arg Val Val Ile Gln Asp Tyr Asp Asn Gln His Glu Gln Asp
                        450                 455                 460
        Arg Pro Thr Pro Ser Pro Ala Pro Ser Arg Pro Phe Ser Val Leu Arg
        465                 470                 475                 480
        Ala Asn Asp Val Leu Trp Leu Ser Leu Thr Ala Ala Glu Tyr Asp Gln
                        485                 490                 495
        Thr Thr Tyr Gly Ser Ser Thr Asn Pro Met Tyr Val Ser Asp Thr Val
                        500                 505                 510
        Thr Phe Val Asn Val Ala Thr Gly Ala Gln Gly Val Ser Arg Ser Leu
                        515                 520                 525
        Asp Trp Ser Lys Val Thr Leu Asp Gly Arg Pro Leu Thr Thr Ile Gln
        530                 535                 540
        Gln Tyr Ser Lys Thr Phe Tyr Val Leu Pro Leu Arg Gly Lys Leu Ser
        545                 550                 555                 560
        Phe Trp Glu Ala Gly Thr Thr Lys Ala Gly Tyr Pro Tyr Asn Tyr Asn
                        565                 570                 575
        Thr Thr Ala Ser Asp Gln Ile Leu Ile Glu Asn Ala Ala Gly His Arg
                        580                 585                 590
        Val Cys Ile Ser Thr Tyr Thr Asn Leu Gly Ser Gly Pro Val Ser
                        595                 600                 605
        Ile Ser Ala Val Gly Val Leu Ala Pro His Ser Ala Leu Ala Ile Leu
                        610                 615                 620
        Glu Asp Thr Ala Asp Tyr Pro Ala Arg Ala His Thr Phe Asp Phe
        625                 630                 635                 640
        Cys Pro Glu Cys Arg Ser Leu Gly Leu Gln Gly Cys Ala Phe Gln Ser
                        645                 650                 655
```

Thr Val Ala Glu Leu Gln Arg Leu Lys Met Lys Val Gly Lys Thr Arg
            660                 665                 670

Glu Tyr

<210> SEQ ID NO 8
<211> LENGTH: 672
<212> TYPE: PRT
<213> ORGANISM: Hepatitis E virus

<400> SEQUENCE: 8

Met Asn Asn Met Phe Cys Ser Val His Gly Asp Ala Thr Met Arg
1               5                   10                  15

Ser Arg Ala Leu Leu Phe Leu Leu Phe Val Leu Leu Pro Met Leu Pro
                20                  25                  30

Ala Pro Pro Ala Gly Gln Pro Ser Gly Arg Arg Arg Gly Gln Ala Gly
                35                  40                  45

Cys Gly Gly Gly Phe Trp Gly Asp Arg Val Asp Ser Gln Pro Phe Ala
            50                  55                  60

Leu Pro Tyr Ile His Pro Thr Asn Pro Phe Ala Ser Asp Ile Pro Ala
65              70                  75                  80

Ala Ala Gly Thr Gly Ala Arg Pro Arg Gln Pro Ile Arg Pro Leu Gly
                85                  90                  95

Ser Ala Trp Arg Asp Gln Ser Gln Arg Pro Ala Ala Ser Thr Arg Arg
                100                 105                 110

Arg Pro Ala Pro Ala Gly Ala Ser Pro Leu Thr Ala Val Ala Pro Ala
                115                 120                 125

Pro Asp Thr Ala Pro Val Pro Asp Ala Asp Ser Arg Gly Ala Ile Leu
                130                 135                 140

Arg Arg Gln Tyr Asn Leu Ser Thr Ser Pro Leu Thr Ser Thr Ile Ala
145             150                 155                 160

Thr Gly Thr Asn Phe Val Leu Tyr Ala Ala Pro Leu Ser Pro Leu Leu
                165                 170                 175

Pro Leu Gln Asp Gly Thr Asn Thr His Ile Met Ala Thr Glu Ala Ser
                180                 185                 190

Asn Tyr Ala Gln Tyr Arg Val Val Arg Ala Thr Ile Arg Tyr Arg Pro
                195                 200                 205

Leu Val Pro Asn Ala Val Gly Gly Tyr Ala Ile Ser Ile Ser Phe Trp
                210                 215                 220

Pro Gln Thr Thr Thr Thr Pro Thr Ser Val Asp Met Asn Ser Ile Thr
225             230                 235                 240

Ser Thr Asp Val Arg Ile Leu Val Gln Pro Gly Ile Ala Ser Glu Leu
                245                 250                 255

Val Thr Pro Ser Glu Arg Leu His Tyr Arg Asn Gln Gly Trp Arg Ser
                260                 265                 270

Val Glu Thr Ser Gly Val Ala Glu Glu Glu Ala Thr Ser Gly Leu Val
                275                 280                 285

Met Leu Cys Ile His Gly Ser Pro Val Asn Ser Tyr Thr Asn Thr Pro
                290                 295                 300

Tyr Thr Gly Ala Leu Gly Leu Leu Asp Phe Ala Leu Glu Leu Glu Phe
305             310                 315                 320

Arg Asn Leu Thr Pro Gly Asn Thr Asn Thr Arg Val Ser Arg Tyr Ser
                325                 330                 335

Ser Ser Ala Arg His His Lys Leu Arg Arg Gly Pro Asp Gly Thr Ala Glu
                340                 345                 350

Leu Thr Thr Thr Ala Ala Thr Arg Phe Met Lys Asp Leu His Phe Thr
            355                 360                 365

Gly Thr Asn Gly Val Gly Glu Val Gly Arg Gly Ile Ala Leu Thr Leu
        370                 375                 380

Phe Asn Leu Ala Asp Thr Leu Leu Gly Gly Leu Pro Thr Glu Leu Ile
385                 390                 395                 400

Ser Ser Ala Gly Gly Gln Leu Phe Tyr Ser Arg Pro Val Val Ser Ala
                405                 410                 415

Asn Gly Glu Leu Thr Val Lys Leu Tyr Thr Ser Val Glu Asn Ala Gln
            420                 425                 430

Gln Asp Lys Gly Val Ala Ile Pro His Asp Ile Asp Leu Gly Glu Ser
        435                 440                 445

Arg Val Val Ile Gln Asp Tyr Asp Asn Gln His Glu Gln Asp Arg Pro
    450                 455                 460

Thr Pro Ser Pro Ala Pro Ser Arg Pro Phe Ser Val Leu Arg Ala Asn
465                 470                 475                 480

Asp Val Leu Trp Leu Ser Leu Thr Ala Ala Glu Tyr Asp Gln Thr Thr
                485                 490                 495

Tyr Gly Ser Ser Thr Asn Pro Met Tyr Val Ser Asp Thr Val Thr Phe
            500                 505                 510

Val Asn Val Ala Thr Gly Ala Gln Gly Val Ser Arg Ser Leu Asp Trp
        515                 520                 525

Ser Lys Val Thr Leu Asp Gly Arg Pro Leu Thr Thr Ile Gln Gln Tyr
    530                 535                 540

Ser Lys Thr Phe Tyr Val Leu Pro Leu Arg Gly Lys Leu Ser Phe Trp
545                 550                 555                 560

Glu Ala Gly Thr Thr Lys Ala Gly Tyr Pro Tyr Asn Tyr Asn Thr Thr
                565                 570                 575

Ala Ser Asp Gln Ile Leu Ile Glu Asn Ala Ala Gly His Arg Val Cys
            580                 585                 590

Ile Ser Thr Tyr Thr Thr Asn Leu Gly Ser Gly Pro Val Ser Val Ser
        595                 600                 605

Ala Val Gly Val Leu Ala Pro His Ser Ala Leu Ala Ala Leu Glu Asp
    610                 615                 620

Thr Ala Asp Tyr Pro Ala Arg Ala His Thr Phe Asp Asp Phe Cys Pro
625                 630                 635                 640

Glu Cys Arg Ala Leu Gly Leu Gln Gly Cys Ala Phe Gln Ser Thr Val
                645                 650                 655

Gly Glu Leu Gln Arg Leu Lys Met Lys Val Gly Lys Thr Arg Glu Tyr
            660                 665                 670

<210> SEQ ID NO 9
<211> LENGTH: 671
<212> TYPE: PRT
<213> ORGANISM: Hepatitis E virus

<400> SEQUENCE: 9

Met Phe Phe Cys Ser Val His Gly Asp Ala Thr Met Arg Ser Arg Ala
1               5                   10                  15

Leu Leu Phe Leu Leu Phe Val Leu Leu Pro Met Leu Pro Ala Pro Pro
            20                  25                  30

Ala Gly Gln Pro Ser Gly Arg Arg Gly Arg Arg Ser Gly Gly Ala
        35                  40                  45

Gly Gly Gly Phe Trp Gly Asp Arg Val Asp Ser Gln Pro Phe Ala Leu

```
            50                  55                  60
Pro Tyr Ile His Pro Thr Asn Pro Phe Ala Ser Asp Ile Pro Thr Ala
 65                  70                  75                  80

Ala Gly Ser Gly Ala Arg Pro Arg Gln Pro Val Arg Pro Leu Gly Ser
                 85                  90                  95

Ala Trp Arg Asp Gln Ser Gln Arg Pro Ala Ala Ser Ala Arg Arg Arg
                100                 105                 110

Pro Ala Pro Ala Gly Ala Ser Pro Leu Thr Ala Val Ala Pro Ala Pro
                115                 120                 125

Asp Thr Ala Pro Val Pro Asp Val Asp Ser Arg Gly Ala Ile Leu Arg
130                 135                 140

Arg Gln Tyr Asn Leu Ser Thr Ser Pro Leu Thr Ser Thr Ile Ala Thr
145                 150                 155                 160

Gly Thr Asn Leu Val Leu Tyr Ala Ala Pro Leu Ser Pro Leu Leu Pro
                165                 170                 175

Leu Gln Asp Gly Thr Asn Thr His Ile Met Ala Thr Glu Ala Ser Asn
                180                 185                 190

Tyr Ala Gln Tyr Arg Val Val Arg Ala Thr Ile Arg Tyr Arg Pro Leu
                195                 200                 205

Val Pro Asn Ala Val Gly Gly Tyr Ala Ile Ser Ile Ser Phe Trp Pro
210                 215                 220

Gln Thr Thr Thr Pro Thr Ser Val Asp Met Asn Ser Ile Thr Ser
225                 230                 235                 240

Thr Asp Val Arg Ile Leu Val Gln Pro Gly Ile Ala Ser Glu Leu Val
                245                 250                 255

Ile Pro Ser Glu Arg Leu His Tyr Arg Asn Gln Gly Trp Arg Ser Val
                260                 265                 270

Glu Thr Ser Gly Val Ala Glu Glu Ala Thr Ser Gly Leu Val Met
                275                 280                 285

Leu Cys Ile His Gly Ser Pro Val Asn Ser Tyr Thr Asn Thr Pro Tyr
290                 295                 300

Thr Gly Ala Leu Gly Leu Leu Asp Phe Ala Leu Glu Leu Glu Phe Arg
305                 310                 315                 320

Asn Leu Thr Pro Gly Asn Thr Asn Thr Arg Val Ser Arg Tyr Ser Ser
                325                 330                 335

Ser Ala Arg His Lys Leu Arg Arg Gly Pro Asp Gly Thr Ala Glu Leu
                340                 345                 350

Thr Thr Thr Ala Ala Thr Arg Phe Met Lys Asp Leu His Phe Thr Gly
                355                 360                 365

Thr Asn Gly Val Gly Glu Val Gly Arg Gly Ile Ala Leu Thr Leu Phe
370                 375                 380

Asn Leu Ala Asp Thr Leu Leu Gly Gly Leu Pro Thr Glu Leu Ile Ser
385                 390                 395                 400

Ser Ala Gly Gly Gln Leu Phe Tyr Ser Arg Pro Val Val Ser Ala Asn
                405                 410                 415

Gly Glu Pro Thr Val Lys Leu Tyr Thr Ser Val Glu Asn Ala Gln Gln
                420                 425                 430

Asp Lys Gly Ile Ala Ile Pro His Asp Ile Asp Leu Gly Glu Ser Arg
                435                 440                 445

Val Val Ile Gln Asp Tyr Asp Asn Gln His Glu Gln Asp Arg Pro Thr
450                 455                 460

Pro Ser Pro Ala Pro Ser Arg Pro Phe Ser Val Leu Arg Ala Asn Asp
465                 470                 475                 480
```

```
Val Leu Trp Leu Ser Leu Thr Ala Ala Glu Tyr Asp Gln Thr Thr Tyr
                485                 490                 495

Gly Ser Ser Thr Asn Pro Met Tyr Val Ser Asp Thr Val Thr Phe Val
            500                 505                 510

Asn Val Ala Thr Gly Ala Gln Gly Val Ser Arg Ser Leu Asp Trp Ser
            515                 520                 525

Lys Val Thr Leu Asp Gly Arg Pro Leu Thr Thr Ile Gln Gln Tyr Ser
        530                 535                 540

Lys Thr Phe Phe Val Leu Pro Leu Arg Gly Lys Leu Ser Phe Trp Glu
545                 550                 555                 560

Ala Gly Thr Thr Lys Ala Gly Tyr Pro Tyr Asn Tyr Asn Thr Thr Ala
                565                 570                 575

Ser Asp Gln Ile Leu Ile Glu Asn Ala Ala Gly His Arg Val Cys Ile
                580                 585                 590

Ser Thr Tyr Thr Thr Asn Leu Gly Ser Gly Pro Val Ser Ile Ser Ala
            595                 600                 605

Val Gly Val Leu Ala Pro His Ser Ala Leu Ala Ala Leu Glu Asp Thr
        610                 615                 620

Val Asp Tyr Pro Ala Arg Ala His Thr Phe Asp Asp Phe Cys Pro Glu
625                 630                 635                 640

Cys Arg Thr Leu Gly Leu Gln Gly Cys Ala Phe Gln Ser Thr Val Ala
                645                 650                 655

Glu Leu Gln Arg Leu Lys Met Lys Val Gly Lys Thr Arg Glu Tyr
                660                 665                 670

<210> SEQ ID NO 10
<211> LENGTH: 668
<212> TYPE: PRT
<213> ORGANISM: Hepatitis E virus

<400> SEQUENCE: 10

Met Phe Phe Cys Ser Val His Gly Asp Ala Thr Met Arg Ser Arg Ala
1               5                   10                  15

Leu Leu Phe Leu Leu Leu Val Phe Leu Pro Met Leu Pro Ala Leu Pro
            20                  25                  30

Ala Gly Gln Pro Ser Gly Arg Arg Gly Arg Arg Ser Gly Ser Ala
            35                  40                  45

Gly Gly Gly Phe Trp Gly Asp Arg Val Asp Ser Gln Pro Phe Ala Leu
        50                  55                  60

Pro Tyr Ile His Pro Thr Asn Pro Phe Ala Ser Asp Ile Pro Thr Ala
65                  70                  75                  80

Ala Gly Ala Gly Ala Arg Pro Arg Gln Pro Ala Arg Pro Leu Gly Ser
                85                  90                  95

Ala Trp Arg Asp Gln Ser Gln Arg Pro Ala Thr Ser Thr Arg Arg Arg
                100                 105                 110

Ser Ala Pro Val Gly Ala Ser Pro Leu Thr Ala Val Ala Pro Ala Pro
            115                 120                 125

Asp Thr Ala Pro Val Pro Asp Val Asp Ser Arg Gly Ala Ile Leu Arg
        130                 135                 140

Arg Gln Tyr Asn Leu Ser Thr Ser Pro Leu Thr Ser Thr Ile Ala Thr
145                 150                 155                 160

Gly Thr Asn Leu Val Leu Tyr Ala Ala Pro Leu Ser Pro Leu Leu Pro
                165                 170                 175

Leu Gln Asp Gly Thr Asn Thr His Ile Met Ala Thr Glu Ala Ser Asn
```

-continued

```
                180                 185                 190
Tyr Ala Gln Tyr Arg Val Val Arg Ala Thr Ile Arg Tyr Arg Pro Leu
            195                 200                 205
Val Pro Asn Ala Val Gly Gly Tyr Ala Ile Ser Ile Ser Phe Trp Pro
        210                 215                 220
Gln Thr Thr Thr Thr Pro Thr Ser Val Asp Met Asn Ser Ile Thr Ser
225                 230                 235                 240
Thr Asp Val Arg Ile Leu Val Gln Ser Gly Ile Ala Ser Glu Leu Val
                245                 250                 255
Ile Pro Ser Glu Arg Leu His Tyr Arg Asn Gln Gly Trp Arg Ser Val
            260                 265                 270
Glu Thr Ser Gly Val Ala Glu Glu Ala Thr Ser Gly Leu Val Met
        275                 280                 285
Leu Cys Ile His Gly Ser Pro Val Asn Ser Tyr Thr Asn Thr Pro Tyr
        290                 295                 300
Thr Gly Ala Leu Gly Leu Leu Asp Phe Ala Leu Glu Leu Glu Phe Arg
305                 310                 315                 320
Asn Leu Thr Pro Gly Asn Thr Asn Met Arg Val Ser Arg His Ser Ser
                325                 330                 335
Ser Ala Arg His Lys Leu Arg Arg Gly Pro Asp Gly Thr Ala Glu Leu
            340                 345                 350
Thr Thr Thr Ala Ala Thr Arg Phe Met Lys Asp Leu His Phe Thr Gly
        355                 360                 365
Thr Asn Gly Val Gly Glu Val Gly Arg Gly Ile Ala Leu Thr Leu Phe
        370                 375                 380
Asn Leu Ala Asp Thr Leu Leu Gly Gly Leu Pro Thr Glu Leu Ile Ser
385                 390                 395                 400
Ser Ala Gly Gly Gln Leu Phe Tyr Ser Arg Pro Val Val Ser Ala Asn
                405                 410                 415
Gly Glu Pro Thr Val Lys Leu Tyr Thr Ser Val Glu Asn Ala Gln Gln
            420                 425                 430
Asp Lys Gly Ile Ala Ile Pro His Asp Ile Asp Leu Gly Glu Ser Arg
        435                 440                 445
Val Gly Ile Gln Asp Tyr Asp Asn Gln His Glu Gln Asp Arg Pro Thr
        450                 455                 460
Pro Ser Pro Ala Pro Ser Arg Pro Phe Ser Val Leu Arg Ala Asn Asp
465                 470                 475                 480
Val Leu Trp Leu Ser Leu Thr Ala Ala Glu Tyr Asp Gln Thr Thr Tyr
                485                 490                 495
Gly Ser Ser Thr Asn Pro Met Tyr Val Ser Asp Thr Val Thr Phe Val
            500                 505                 510
Asn Val Ala Thr Gly Ala Gln Gly Val Ser Arg Ser Leu Asp Trp Ser
        515                 520                 525
Lys Val Thr Leu Asp Gly Arg Ser Leu Thr Thr Ile Gln Gln Tyr Ser
530                 535                 540
Lys Thr Phe Phe Val Leu Pro Leu Arg Gly Lys Leu Ser Phe Trp Glu
545                 550                 555                 560
Ala Gly Thr Thr Lys Ala Gly Tyr Pro Tyr Asn Tyr Asn Thr Thr Ala
                565                 570                 575
Ser Asp Gln Ile Leu Ile Glu Asn Ala Ala Gly His Arg Val Cys Ile
            580                 585                 590
Ser Thr Tyr Thr Thr Asn Leu Gly Ser Gly Pro Val Ser Ile Ser Ala
        595                 600                 605
```

Val Gly Val Leu Ala Pro His Ser Ala Leu Ala Val Leu Glu Asp Thr
        610                 615                 620

Val Asp Tyr Pro Ala Arg Ala His Thr Phe Asp Asp Phe Cys Pro Glu
625                 630                 635                 640

Cys Arg Ala Leu Gly Leu Gln Gly Cys Ala Phe Gln Ser Thr Val Ala
                645                 650                 655

Glu Leu Gln Arg Leu Lys Met Lys Val Gly Asn His
            660                 665

<210> SEQ ID NO 11
<211> LENGTH: 660
<212> TYPE: PRT
<213> ORGANISM: Hepatitis E virus

<400> SEQUENCE: 11

Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Arg Gly Arg
                20                  25                  30

Arg Ser Gly Gly Ser Gly Gly Gly Phe Trp Gly Asp Arg Ala Asp Ser
            35                  40                  45

Gln Pro Phe Ala Ile Pro Tyr Ile His Pro Thr Asn Pro Phe Ala Pro
    50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu His Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Leu Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val

```
                305                 310                 315                 320
Ser Arg Tyr Ser Ser Thr Ala Arg His Arg Leu Arg Arg Gly Ala Asp
                    325                 330                 335

Gly Thr Ala Glu Leu Thr Thr Thr Ala Ala Thr Arg Phe Met Lys Asp
                    340                 345                 350

Leu Tyr Phe Thr Ser Thr Asn Gly Val Gly Glu Ile Gly Arg Gly Ile
                    355                 360                 365

Ala Leu Thr Leu Phe Asn Leu Ala Asp Thr Leu Leu Gly Gly Leu Pro
                370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                    405                 410                 415

Glu Asn Ala Gln Gln Asp Lys Gly Ile Ala Ile Pro His Asp Ile Asp
                    420                 425                 430

Leu Gly Glu Ser Arg Val Val Ile Gln Asp Tyr Asp Asn Gln His Glu
                    435                 440                 445

Gln Asp Arg Pro Thr Pro Ser Pro Ala Pro Ser Arg Pro Phe Ser Val
                450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                    485                 490                 495

Ser Val Thr Leu Val Asn Val Ala Thr Gly Ala Gln Ala Val Ala Arg
                    500                 505                 510

Ser Leu Asp Trp Thr Lys Val Thr Leu Asp Gly Arg Pro Leu Ser Thr
                    515                 520                 525

Thr Gln Gln Tyr Ser Lys Thr Phe Phe Val Leu Pro Leu Arg Gly Lys
                    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                    565                 570                 575

His Arg Val Ala Ile Ser Thr Tyr Thr Thr Ser Leu Gly Ala Gly Pro
                    580                 585                 590

Val Ser Ile Ser Ala Val Ala Val Leu Ala Pro His Ser Ala Leu Ala
                    595                 600                 605

Leu Leu Glu Asp Thr Met Asp Tyr Pro Ala Arg Ala His Thr Phe Asp
                610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                    645                 650                 655

Thr Arg Glu Leu
            660

<210> SEQ ID NO 12
<211> LENGTH: 660
<212> TYPE: PRT
<213> ORGANISM: Hepatitis E virus

<400> SEQUENCE: 12

Met Arg Pro Arg Pro Ile Leu Leu Leu Leu Met Phe Leu Pro Met
1               5                   10                  15
```

Leu Pro Ala Pro Pro Gly Gln Pro Ser Gly Arg Arg Gly Arg
            20              25              30

Arg Ser Gly Gly Ser Gly Gly Phe Trp Gly Asp Arg Val Asp Ser
        35              40              45

Gln Pro Phe Ala Ile Pro Tyr Ile His Pro Thr Asn Pro Phe Ala Pro
    50              55              60

Asp Val Thr Ala Ala Gly Ala Gly Pro Arg Val Arg Gln Pro Ala
65              70              75              80

Arg Pro Leu Gly Ser Ala Trp Arg Asp Gln Ala Gln Arg Pro Ala Val
            85              90              95

Ala Ser Arg Arg Arg Pro Thr Thr Ala Gly Ala Ala Pro Leu Thr Ala
        100             105             110

Val Ala Pro Ala His Asp Thr Pro Pro Val Pro Asp Val Asp Ser Arg
        115             120             125

Gly Ala Ile Leu Arg Arg Gln Tyr Asn Leu Ser Thr Ser Pro Leu Thr
        130             135             140

Ser Ser Val Ala Thr Gly Thr Asn Leu Val Leu Tyr Ala Ala Pro Leu
145             150             155             160

Ser Pro Leu Leu Pro Leu Gln Asp Gly Thr Asn Thr His Ile Met Ala
            165             170             175

Thr Glu Ala Ser Asn Tyr Ala Gln Tyr Arg Val Ala Arg Ala Thr Ile
            180             185             190

Arg Tyr Arg Pro Leu Val Pro Asn Ala Val Gly Gly Tyr Ala Ile Ser
        195             200             205

Ile Ser Phe Trp Pro Gln Thr Thr Thr Pro Thr Ser Val Asp Met
210             215             220

Asn Ser Ile Thr Ser Thr Asp Val Arg Ile Leu Val Gln Pro Gly Ile
225             230             235             240

Ala Ser Glu Leu Val Ile Pro Ser Glu Arg Leu His Tyr Arg Asn Gln
            245             250             255

Gly Trp Arg Ser Val Glu Thr Ser Gly Val Ala Glu Glu Ala Thr
        260             265             270

Ser Gly Leu Val Met Leu Cys Ile His Gly Ser Leu Val Asn Ser Tyr
        275             280             285

Thr Asn Thr Pro Tyr Thr Gly Ala Leu Gly Leu Leu Asp Phe Ala Leu
        290             295             300

Glu Leu Glu Phe Arg Asn Leu Thr Pro Gly Asn Thr Asn Thr Arg Val
305             310             315             320

Ser Arg Tyr Ser Ser Thr Ala Arg His Arg Leu Arg Arg Gly Ala Asp
            325             330             335

Gly Thr Ala Glu Leu Thr Thr Thr Ala Ala Thr Arg Phe Met Lys Asp
            340             345             350

Leu Tyr Phe Thr Ser Thr Asn Gly Val Gly Glu Ile Gly Arg Gly Ile
        355             360             365

Ala Leu Thr Leu Phe Asn Leu Ala Asp Thr Leu Leu Gly Gly Leu Pro
        370             375             380

Thr Glu Leu Ile Ser Ser Ala Gly Gly Gln Leu Phe Tyr Ser Arg Pro
385             390             395             400

Val Val Ser Ala Asn Gly Glu Pro Thr Val Lys Leu Tyr Thr Ser Val
            405             410             415

Glu Asn Ala Gln Gln Asp Lys Gly Ile Ala Ile Pro His Asp Ile Asp
            420             425             430

Leu Gly Glu Ser Arg Val Val Ile Gln Asp Tyr Asp Asn Gln His Glu

```
                435                 440                 445
Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
                500                 505                 510

Ser Leu Asp Trp Thr Lys Val Thr Leu Asp Gly Arg Pro Leu Ser Thr
                515                 520                 525

Ile Gln Gln Tyr Ser Lys Thr Phe Phe Val Leu Pro Leu Arg Gly Lys
530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Ala Pro His Ser Ala Leu Ala
                595                 600                 605

Leu Leu Glu Asp Thr Leu Asp Tyr Pro Ala Arg Ala His Thr Phe Asp
610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 13
<211> LENGTH: 660
<212> TYPE: PRT
<213> ORGANISM: Hepatitis E virus

<400> SEQUENCE: 13

Met Arg Pro Arg Ala Val Leu Leu Leu Phe Val Leu Leu Pro Met
1               5                   10                  15

Leu Pro Ala Pro Pro Ala Gly Gln Pro Ser Gly Arg Arg Gly Arg
                20                  25                  30

Arg Asn Gly Gly Ala Gly Gly Phe Trp Gly Asp Arg Val Asp Ser
                35                  40                  45

Gln Pro Phe Ala Leu Pro Tyr Ile His Pro Thr Asn Pro Phe Ala Ala
50                  55                  60

Asp Val Val Ser Gln Pro Gly Ala Gly Ala Arg Pro Arg Gln Pro Pro
65                  70                  75                  80

Arg Pro Leu Gly Ser Ala Trp Arg Asp Gln Ser Gln Arg Pro Ser Thr
                85                  90                  95

Ala Pro Arg Arg Arg Ser Ala Pro Ala Gly Ala Ala Pro Leu Thr Ala
                100                 105                 110

Val Ser Pro Ala Pro Asp Thr Ala Pro Val Pro Asp Val Asp Ser Arg
                115                 120                 125

Gly Ala Ile Leu Arg Arg Gln Tyr Asn Leu Ser Thr Ser Pro Leu Thr
                130                 135                 140
```

-continued

```
Ser Ser Val Ala Ala Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Thr Gly Val Ala Glu Glu Ala Thr
                260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
        290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Gly Ala Asp
                325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
        355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Thr Ile Pro His Asp Ile Asp
            420                 425                 430

Leu Gly Asp Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                485                 490                 495

Thr Val Thr Leu Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
        515                 520                 525

Ile Gln Gln Tyr Ser Lys Thr Phe Tyr Val Leu Pro Leu Arg Gly Lys
530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
```

```
                        565                 570                 575
His Arg Val Ala Ile Ser Thr Tyr Thr Thr Ser Leu Gly Ala Gly Pro
                580                 585                 590

Thr Ser Ile Ser Ala Val Gly Val Leu Ala Pro His Ser Ala Leu Ala
                595                 600                 605

Val Leu Glu Asp Thr Val Asp Tyr Pro Ala Arg Ala His Thr Phe Asp
            610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Met Lys Val Gly Lys
                645                 650                 655

Thr Arg Glu Ser
            660

<210> SEQ ID NO 14
<211> LENGTH: 660
<212> TYPE: PRT
<213> ORGANISM: Hepatitis E virus

<400> SEQUENCE: 14

Met Arg Pro Arg Pro Ile Leu Leu Leu Leu Met Phe Leu Pro Met
1               5                  10                  15

Leu Pro Ala Pro Pro Gly Gln Pro Ser Gly Arg Arg Gly Arg
                20                  25                  30

Arg Ser Gly Gly Ser Gly Gly Phe Trp Gly Asp Arg Val Asp Ser
                35                  40                  45

Gln Pro Phe Ala Ile Pro Tyr Ile His Pro Thr Asn Pro Phe Ala Pro
            50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
                85                  90                  95

Ala Ser Arg Arg Arg Pro Thr Thr Ala Gly Ala Ala Pro Leu Thr Ala
                100                 105                 110

Val Ala Pro Ala His Asp Thr Pro Pro Val Pro Asp Val Asp Ser Arg
            115                 120                 125

Ala Ala Ile Leu Arg Arg Gln Tyr Asn Leu Ser Thr Ser Pro Leu Thr
130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270
```

```
Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
        290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
            325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
355                 360                 365

Ala Leu Thr Leu Phe Asn Leu Ala Asp Thr Leu Leu Gly Gly Leu Pro
        370                 375                 380

Thr Glu Leu Ile Ser Ser Ala Gly Gly Gln Leu Phe Tyr Ser Arg Pro
385                 390                 395                 400

Val Val Ser Ala His Gly Glu Pro Thr Val Lys Leu Tyr Thr Ser Val
            405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
        450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Ala Pro Val Tyr Val Ser Asp
            485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
        515                 520                 525

Ile Gln Gln Tyr Pro Lys Thr Phe Phe Val Leu Pro Leu Arg Gly Lys
        530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
            565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
        595                 600                 605

Leu Leu Glu Asp Thr Leu Asp Tyr Pro Ala Cys Ala His Thr Phe Asp
        610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
            645                 650                 655

Thr Arg Glu Leu
        660

<210> SEQ ID NO 15
<211> LENGTH: 660
<212> TYPE: PRT
```

<213> ORGANISM: Hepatitis E virus

<400> SEQUENCE: 15

```
Met Gly Pro Arg Pro Ile Leu Leu Leu Phe Leu Met Phe Leu Pro Met
1               5                   10                  15

Leu Leu Ala Pro Pro Gly Gln Pro Ser Gly Arg Arg Arg Gly Arg Arg
            20                  25                  30

Arg Ser Gly Gly Ser Gly Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asn Val Thr Ala Ala Ala Gly Ala Gly Pro Arg Val Arg Gln Pro Val
65                  70                  75                  80

Arg Pro Leu Gly Ser Ala Trp Arg Asp Gln Ala Gln Arg Pro Ala Ala
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
            115                 120                 125

Gly Ala Ile Leu Arg Arg Gln Tyr Asn Leu Ser Thr Ser Pro Leu Thr
130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Pro Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
        355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400
```

```
Val Val Ser Ala Asn Gly Glu Pro Thr Val Lys Leu Tyr Thr Ser Val
            405                 410                 415

Glu Asn Ala Gln Gln Asp Lys Gly Ile Ala Ile Pro Asn Asp Ile Asp
            420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
            485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Ile Gln Gln Tyr Ser Lys Ile Phe Phe Val Leu Pro Leu Arg Gly Lys
            530                 535                 540

Leu Ser Phe Trp Glu Ala Gly Thr Thr Arg Pro Gly Tyr Pro Tyr Asn
545                 550                 555                 560

Tyr Asn Thr Thr Ala Ser Asp Gln Leu Leu Val Glu Asn Ala Ala Gly
            565                 570                 575

His Arg Val Ala Ile Ser Thr Tyr Thr Thr Ser Leu Gly Ala Gly Pro
            580                 585                 590

Val Ser Ile Ser Ala Val Ala Val Leu Gly Pro His Ser Ala Leu Ala
            595                 600                 605

Leu Leu Glu Asp Thr Leu Asp Tyr Pro Ala Arg Ala His Thr Phe Asp
            610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
            645                 650                 655

Thr Arg Glu Leu
            660

<210> SEQ ID NO 16
<211> LENGTH: 660
<212> TYPE: PRT
<213> ORGANISM: Hepatitis E virus

<400> SEQUENCE: 16

Met Arg Pro Arg Ala Val Leu Leu Leu Phe Val Leu Leu Pro Met
1               5                   10                  15

Leu Pro Ala Pro Pro Ala Gly Gln Pro Ser Gly Arg Arg Gly Arg
            20                  25                  30

Arg Ser Gly Gly Ala Gly Gly Gly Phe Trp Gly Asp Arg Val Asp Ser
            35                  40                  45

Gln Pro Phe Ala Leu Pro Tyr Ile His Pro Thr Asn Pro Phe Ala Ala
            50                  55                  60

Asp Val Val Ser Gln Pro Gly Ala Gly Thr Arg Pro Arg Gln Pro Pro
65                  70                  75                  80

Arg Pro Leu Gly Ser Ala Trp Arg Asp Gln Ser Gln Arg Pro Ser Ala
            85                  90                  95

Ala Pro Arg Arg Arg Ser Ala Pro Ala Gly Ala Ala Pro Leu Thr Ala
            100                 105                 110
```

```
Val Ser Pro Ala Pro Asp Thr Ala Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Thr Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu His Phe Ala Gly Thr Asn Gly Val Gly Glu Val Gly Arg Gly Ile
        355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Thr Ile Pro His Asp Ile Asp
            420                 425                 430

Leu Gly Asp Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                485                 490                 495

Thr Val Thr Leu Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
        515                 520                 525
```

```
Ile Gln Gln Tyr Ser Lys Thr Phe Tyr Val Leu Pro Leu Arg Gly Lys
    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
            565                 570                 575

His Arg Val Ala Ile Ser Thr Tyr Thr Thr Ser Leu Gly Ala Gly Pro
        580                 585                 590

Thr Ser Ile Ser Ala Val Gly Val Leu Ala Pro His Ser Ala Leu Ala
    595                 600                 605

Val Leu Glu Asp Thr Ile Asp Tyr Pro Ala Arg Ala His Thr Phe Asp
610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Met Lys Val Gly Lys
            645                 650                 655

Thr Arg Glu Ser
            660

<210> SEQ ID NO 17
<211> LENGTH: 660
<212> TYPE: PRT
<213> ORGANISM: Hepatitis E virus

<400> SEQUENCE: 17

Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Gly Arg
                20                  25                  30

Arg Ser Gly Gly Ser Gly Gly Gly Phe Trp Gly Asp Arg Val Asp Ser
            35                  40                  45

Gln Pro Phe Ala Ile Pro Tyr Ile His Pro Thr Asn Pro Phe Ala Pro
    50                  55                  60

Asp Val Thr Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240
```

```
Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300

Leu Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
                420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Val Leu Ala
            595                 600                 605

Leu Leu Glu Asp Thr Met Asp Tyr Pro Ala Arg Ala His Thr Phe Asp
            610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655
```

Thr Arg Glu Leu
            660

<210> SEQ ID NO 18
<211> LENGTH: 660
<212> TYPE: PRT
<213> ORGANISM: Hepatitis E virus
<220> FEATURE:
<221> NAME/KEY: misc_feature
<222> LOCATION: (481)..(481)
<223> OTHER INFORMATION: Xaa can be any naturally occurring amino acid

<400> SEQUENCE: 18

Met Arg Pro Arg Ala Val Leu Leu Phe Leu Met Phe Leu Pro Met
1               5                   10                  15

Leu Pro Ala Pro Pro Ala Gly Gln Pro Ser Gly Arg Arg Gly Arg
                20                  25                  30

Arg Ser Gly Gly Ala Gly Gly Phe Trp Ser Asp Arg Val Asp Ser
            35                  40                  45

Gln Pro Phe Ala Leu Pro Tyr Ile His Pro Thr Asn Pro Phe Ala Ala
50                  55                      60

Asp Val Val Ser Gln Pro Gly Ala Gly Thr Arg Pro Arg Gln Pro Pro
65                  70                  75                  80

Arg Pro Leu Gly Ser Ala Trp Arg Asp Gln Ser Lys Arg Pro Ser Val
                85                  90                  95

Ala Pro Arg Arg Arg Ser Thr Pro Ala Gly Ala Ala Pro Leu Thr Ala
                100                 105                 110

Ile Ser Pro Ala Pro Asp Thr Ala Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Thr Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp

```
            340                 345                 350
Leu His Phe Thr Gly Thr Asn Gly Val Gly Glu Val Gly Arg Gly Ile
        355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
            405                 410                 415

Glu Asn Ala Gln Gln Asp Lys Gly Ile Thr Ile Pro His Asp Ile Asp
        420                 425                 430

Leu Gly Asp Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
        450                 455                 460

Leu Arg Ala Asn Asp Val Leu Trp Leu Ser Leu Thr Ala Ala Glu Tyr
465                 470                 475                 480

Xaa Gln Thr Thr Tyr Gly Ser Ser Thr Asn Pro Met Tyr Val Ser Asp
            485                 490                 495

Thr Val Thr Leu Val Asn Val Ala Thr Gly Ala Gln Ala Val Ala Arg
        500                 505                 510

Ser Leu Asp Trp Ser Lys Val Thr Leu Asp Gly Arg Pro Leu Thr Thr
        515                 520                 525

Ile Gln Gln Tyr Ser Lys Lys Phe Tyr Val Leu Pro Leu Arg Gly Lys
        530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
            565                 570                 575

His Arg Val Ala Ile Ser Thr Tyr Thr Thr Ser Leu Gly Ala Gly Pro
        580                 585                 590

Thr Ser Ile Ser Ala Val Gly Val Leu Ala Pro His Ser Ala Leu Ala
        595                 600                 605

Val Leu Glu Asp Thr Val Asp Tyr Pro Ala Arg Ala His Thr Phe Asp
610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Met Lys Val Gly Lys
            645                 650                 655

Thr Arg Glu Ser
        660

<210> SEQ ID NO 19
<211> LENGTH: 660
<212> TYPE: PRT
<213> ORGANISM: Hepatitis E virus

<400> SEQUENCE: 19

Met Arg Pro Arg Ala Val Leu Leu Leu Phe Phe Val Leu Leu Pro Met
1               5                   10                  15

Leu Pro Ala Pro Pro Ala Gly Gln Pro Ser Gly Arg Arg Gly Arg
                20                  25                  30

Arg Ser Gly Gly Thr Gly Gly Gly Phe Trp Gly Asp Arg Val Asp Ser
            35                  40                  45
```

```
Gln Pro Phe Ala Leu Pro Tyr Ile His Pro Thr Asn Pro Phe Ala Ser
 50                  55                  60

Asp Ile Pro Thr Ala Thr Gly Ala Gly Ala Arg Pro Arg Gln Pro Ala
 65                  70                  75                  80

Arg Pro Leu Gly Ser Ala Trp Arg Asp Gln Ser Gln Arg Pro Ala Ala
                 85                  90                  95

Pro Ala Arg Arg Arg Ser Ala Pro Ala Gly Ala Ser Pro Leu Thr Ala
            100                 105                 110

Val Ala Pro Ala Pro Asp Thr Ala Pro Val Pro Asp Val Asp Ser Arg
            115                 120                 125

Gly Ala Ile Leu Arg Arg Gln Tyr Asn Leu Ser Thr Ser Pro Leu Thr
130                 135                 140

Ser Thr Ile Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Ile Ala
                165                 170                 175

Thr Glu Ala Ser Asn Tyr Ala Gln Tyr Arg Val Val Arg Ala Thr Ile
                180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Pro Gly Asn Thr Asn Thr Arg Val
305                 310                 315                 320

Ser Arg Tyr Ser Ser Ser Ala Arg His Lys Leu Cys Arg Gly Pro Asp
                325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
                355                 360                 365

Ala Leu Thr Leu Leu Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
                435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
```

```
                465                 470                 475                 480
        Asp Gln Thr Thr Tyr Gly Ser Ser Thr Asn Pro Met Tyr Val Ser Asp
                            485                 490                 495

Thr Val Thr Phe Val Asn Val Ala Thr Gly Thr Gln Gly Val Ser Arg
                        500                 505                 510

Ser Leu Asp Trp Ser Lys Val Thr Leu Asp Gly Arg Pro Leu Thr Thr
                        515                 520                 525

Ile Gln Gln Tyr Ser Lys Thr Phe Phe Val Leu Pro Leu Arg Gly Lys
                    530                 535                 540

Leu Ser Phe Trp Glu Ala Gly Thr Thr Lys Ala Gly Tyr Pro Tyr Asn
        545                 550                 555                 560

Tyr Asn Thr Thr Ala Ser Asp Gln Ile Leu Ile Glu Asn Ala Pro Gly
                        565                 570                 575

His Arg Val Cys Ile Ser Thr Tyr Thr Thr Asn Leu Gly Ser Gly Pro
                    580                 585                 590

Val Ser Ile Ser Ala Val Gly Val Leu Ala Pro His Ser Ala Leu Ala
                    595                 600                 605

Ala Leu Glu Asp Thr Val Asp Tyr Pro Ala Arg Ala His Thr Phe Asp
        610                 615                 620

Asp Phe Cys Pro Glu Cys Arg Ala Leu Gly Leu Gln Gly Cys Ala Phe
        625                 630                 635                 640

Gln Ser Thr Val Ala Glu Leu Gln Arg Leu Lys Met Lys Val Gly Lys
                        645                 650                 655

Thr Gln Glu Tyr
                    660

<210> SEQ ID NO 20
<211> LENGTH: 660
<212> TYPE: PRT
<213> ORGANISM: Hepatitis E virus

<400> SEQUENCE: 20

Met Arg Pro Arg Pro Ile Leu Leu Leu Leu Met Phe Leu Pro Met
 1               5                  10                  15

Leu Pro Ala Pro Pro Gly Gln Pro Ser Gly Arg Arg Gly Arg
                20                  25                  30

Arg Ser Gly Gly Ser Gly Gly Gly Phe Trp Gly Asp Arg Val Asp Ser
            35                  40                  45

Gln Pro Phe Ala Ile Pro His Ile His Pro Thr Asn Pro Phe Ala Pro
    50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95

Thr Ser Arg Arg Arg Pro Thr Thr Ala Gly Ala Ala Pro Leu Thr Ala
                100                 105                 110

Val Ala Pro Ala His Asp Thr Pro Val Pro Asp Val Asp Ser Arg
                115                 120                 125

Gly Ala Ile Leu Arg Arg Gln Tyr Asn Leu Ser Thr Ser Pro Leu Thr
            130                 135                 140

Ser Pro Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175
```

-continued

```
Thr Glu Ala Ser Asn Tyr Ala Gln Tyr Arg Val Ala Arg Ala Thr Ile
            180                 185                 190
Arg Tyr Arg Pro Leu Val Pro Asn Ala Val Gly Gly Tyr Ala Ile Ser
        195                 200                 205
Ile Ser Phe Trp Pro Gln Thr Thr Thr Pro Thr Ser Val Asp Met
    210                 215                 220
Asn Ser Ile Thr Ser Asp Val Arg Ile Leu Val Gln Pro Gly Ile
225                 230                 235                 240
Ala Ser Glu Leu Val Ile Pro Ser Glu Arg Leu His Tyr Arg Asn Gln
                245                 250                 255
Gly Trp Arg Ser Val Glu Thr Ser Gly Val Ala Glu Glu Ala Thr
            260                 265                 270
Ser Gly Leu Val Met Leu Cys Ile His Gly Leu Pro Val Asn Ser Tyr
        275                 280                 285
Thr Asn Thr Pro Tyr Thr Gly Ala Leu Gly Leu Leu Asp Phe Ala Leu
    290                 295                 300
Glu Phe Glu Phe Arg Asn Leu Thr Pro Gly Asn Thr Asn Thr Arg Val
305                 310                 315                 320
Ser Arg Tyr Ser Ser Thr Ala Arg His Arg Leu Arg Arg Gly Ala Asp
                325                 330                 335
Gly Thr Ala Glu Leu Thr Thr Ala Ala Thr Arg Phe Met Lys Asp
            340                 345                 350
Leu Tyr Phe Thr Ser Thr Asn Gly Val Gly Glu Ile Gly Arg Gly Ile
        355                 360                 365
Ala Leu Thr Leu Phe Asn Leu Ala Asp Thr Leu Leu Gly Gly Leu Pro
    370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
                405                 410                 415
Glu Asn Ala Gln Gln Asp Lys Gly Ile Ala Ile Pro His Asp Ile Asp
            420                 425                 430
Leu Gly Glu Ser Arg Val Val Ile Gln Asp Tyr Asp Asn Gln His Glu
        435                 440                 445
Gln Asp Arg Pro Thr Pro Ser Pro Ala Pro Ser Arg Pro Phe Ser Val
    450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
Ser Val Thr Leu Val Asn Val Ala Thr Gly Ala Gln Ala Val Ala Arg
            500                 505                 510
Ser Leu Asp Trp Thr Lys Val Thr Leu Asp Gly Arg Pro Leu Ser Thr
        515                 520                 525
Ile Gln Gln Tyr Ser Lys Thr Phe Phe Val Leu Pro Leu Arg Gly Lys
    530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Leu Leu Ile Glu Asn Ala Ala Gly
                565                 570                 575
His Arg Val Ala Ile Ser Thr Tyr Thr Thr Ser Leu Gly Ala Gly Pro
            580                 585                 590
Val Ala Ile Ser Ala Val Ala Val Leu Ala Pro His Ser Ala Leu Ala
```

```
            595                 600                 605
Leu Leu Glu Asp Thr Met Asp Tyr Pro Ala Arg Ala His Thr Phe Asp
        610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 21
<211> LENGTH: 660
<212> TYPE: PRT
<213> ORGANISM: Hepatitis E virus

<400> SEQUENCE: 21

Met Arg Pro Arg Ala Val Leu Leu Phe Phe Val Leu Leu Pro Met
1               5                   10                  15

Leu Pro Ala Pro Pro Ala Gly Gln Pro Ser Gly Arg Arg Gly Arg
                20                  25                  30

Arg Ser Gly Gly Ala Gly Gly Gly Phe Trp Gly Asp Arg Val Asp Ser
            35                  40                  45

Gln Pro Phe Ala Leu Pro Tyr Ile His Pro Thr Asn Pro Phe Ala Ala
50                  55                  60

Asp Val Ala Ser Gln Ser Gly Ala Gly Ala Arg Pro Arg Gln Pro Pro
65                  70                  75                  80

Arg Pro Leu Gly Ser Ala Trp Arg Asp Gln Ser Gln Arg Pro Pro Ala
                85                  90                  95

Val Pro Arg Arg Arg Ser Ala Pro Ala Gly Ala Ala Pro Leu Thr Ala
                100                 105                 110

Ile Ser Pro Ala Pro Asp Thr Ala Pro Val Pro Asp Val Asp Ser Arg
                115                 120                 125

Gly Ala Ile Leu Arg Arg Gln Tyr Asn Leu Ser Thr Ser Pro Leu Thr
            130                 135                 140

Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
                195                 200                 205

Ile Ser Phe Trp Pro Gln Thr Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Thr Gly Val Ala Glu Glu Ala Thr
                260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300
```

```
Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
            325                 330                 335

Gly Thr Ala Glu Leu Thr Thr Thr Ala Ala Thr Arg Phe Met Lys Asp
                340                 345                 350

Leu His Phe Thr Gly Thr Asn Gly Val Gly Glu Val Gly Arg Gly Ile
            355                 360                 365

Ala Leu Thr Leu Phe Asn Leu Ala Asp Thr Leu Leu Gly Gly Leu Pro
        370                 375                 380

Thr Glu Leu Ile Ser Ser Ala Gly Gly Gln Leu Phe Tyr Ser Arg Pro
385                 390                 395                 400

Val Ala Ser Ala Asn Gly Glu Pro Thr Val Lys Leu Tyr Thr Ser Val
            405                 410                 415

Glu Asn Ala Gln Gln Asp Lys Gly Ile Thr Ile Pro His Asp Ile Asp
                420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
        450                 455                 460

Leu Arg Ala Asn Asp Val Leu Trp Leu Ser Leu Thr Val Ala Glu Tyr
465                 470                 475                 480

Asp Gln Thr Thr Tyr Gly Ser Ser Thr Asn Pro Met Tyr Val Ser Asp
                485                 490                 495

Thr Ala Thr Phe Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
        515                 520                 525

Ile Gln Gln Tyr Ser Lys Thr Phe Tyr Val Leu Pro Leu Arg Gly Lys
530                 535                 540

Leu Ser Phe Trp Glu Ala Gly Thr Thr Lys Ala Gly Tyr Pro Tyr Asn
545                 550                 555                 560

Tyr Asn Thr Ala Ala Ser Asp Gln Ile Leu Ile Glu Asn Ala Ala Gly
            565                 570                 575

His Arg Val Ala Ile Ser Thr Tyr Thr Thr Ser Leu Gly Ala Ser Pro
                580                 585                 590

Thr Ser Ile Ser Ala Val Gly Val Leu Ala Pro His Ser Ala Leu Ala
            595                 600                 605

Val Leu Glu Asp Thr Val Asp Tyr Pro Ala Arg Ala His Thr Phe Asp
610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Met Lys Val Gly Lys
            645                 650                 655

Thr Arg Glu Ser
            660

<210> SEQ ID NO 22
<211> LENGTH: 660
<212> TYPE: PRT
<213> ORGANISM: Hepatitis E virus

<400> SEQUENCE: 22

Met Arg Pro Arg Ala Val Leu Leu Leu Leu Phe Val Leu Leu Pro Met
1               5                   10                  15
```

-continued

Leu Pro Ala Pro Pro Ala Gly Gln Pro Ser Gly Arg Arg Gly Arg
         20                  25                  30

Arg Ser Gly Gly Ala Gly Gly Phe Trp Gly Asp Arg Val Asp Ser
         35                  40                  45

Gln Pro Phe Ala Leu Pro Tyr Ile His Pro Thr Asn Pro Phe Ala Ala
50                   55                  60

Asp Val Val Ser Gln Pro Gly Ala Gly Thr Arg Pro Arg Gln Pro Pro
65                   70                  75                  80

Arg Pro Leu Gly Ser Ala Trp Arg Asp Gln Ser Gln Arg Pro Ser Ala
             85                  90                  95

Ala Pro Arg Arg Pro Ala Pro Ala Gly Ala Thr Pro Leu Thr Ala
            100                 105                 110

Val Ser Pro Ala Pro Asp Ala Ala Pro Val Pro Asp Val Asp Ser Arg
            115                 120                 125

Gly Ala Ile Leu Arg Arg Gln Tyr Asn Leu Ser Thr Ser Pro Leu Thr
130                 135                 140

Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
            165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Val Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Val
225                 230                 235                 240

Ala Ser Glu Leu Val Ile Pro Ser Glu Arg Leu His Tyr Arg Asn Gln
            245                 250                 255

Gly Trp Arg Ser Val Glu Thr Thr Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
            325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
            355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
            405                 410                 415

Glu Asn Ala Gln Gln Asp Lys Gly Ile Thr Ile Pro His Asp Ile Asp
            420                 425                 430

```
Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
        450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                    485                 490                 495

Thr Val Thr Leu Val Asn Val Ala Thr Gly Ala Gln Ala Val Ala Arg
                500                 505                 510

Ser Leu Asp Trp Ser Lys Val Thr Leu Asp Gly Arg Pro Leu Thr Thr
            515                 520                 525

Ile Gln Gln Tyr Ser Lys Thr Phe Tyr Val Leu Pro Leu Arg Gly Lys
        530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ser Gly
                    565                 570                 575

His Arg Val Ala Ile Ser Thr Tyr Thr Thr Ser Leu Gly Ala Gly Pro
                580                 585                 590

Thr Ser Ile Ser Ala Val Gly Val Leu Ala Pro His Ser Ala Leu Ala
            595                 600                 605

Val Leu Glu Asp Thr Ile Asp Tyr Pro Ala Arg Ala His Thr Phe Asp
        610                 615                 620

Asp Phe Cys Pro Glu Cys Arg Ala Leu Gly Phe Gln Gly Cys Ala Phe
625                 630                 635                 640

Gln Ser Thr Ile Ala Glu Leu Gln Arg Leu Lys Met Lys Val Gly Lys
                    645                 650                 655

Thr Arg Glu Ser
            660

<210> SEQ ID NO 23
<211> LENGTH: 660
<212> TYPE: PRT
<213> ORGANISM: Hepatitis E virus

<400> SEQUENCE: 23

Met Cys Pro Arg Ala Val Leu Leu Leu Leu Phe Val Leu Leu Pro Met
1               5                   10                  15

Leu Pro Ala Pro Pro Ala Gly Gln Pro Ser Gly Arg Arg Arg Gly Arg
            20                  25                  30

Arg Ser Gly Gly Ala Gly Gly Gly Phe Trp Gly Asp Arg Val Asp Ser
        35                  40                  45

Gln Pro Phe Ala Leu Pro Tyr Ile His Pro Thr Asn Pro Phe Ala Ala
    50                  55                  60

Asp Val Phe Ser Gln Ser Gly Ala Gly Ala Arg Pro Arg Gln Pro Pro
65                  70                  75                  80

Arg Pro Leu Gly Ser Ala Trp Arg Asp Gln Ser Gln Arg Pro Ser Ala
                85                  90                  95

Ala Pro Arg Arg Arg Ser Thr Pro Ala Gly Ala Ala Pro Leu Thr Ala
            100                 105                 110

Thr Ser Pro Ala Pro Asp Thr Ala Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140
```

-continued

```
Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
            165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Thr Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
            355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Thr Ile Pro His Asp Ile Asp
            420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
            485                 490                 495

Thr Val Thr Phe Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
            515                 520                 525

Ile Gln Gln Tyr Ser Lys Thr Phe Tyr Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560
```

```
Tyr Asn Thr Thr Ala Ser Asp Gln Ile Leu Ile Glu Asn Ala Ala Gly
                565                 570                 575

His Arg Val Ala Ile Ser Thr Tyr Thr Thr Ser Leu Gly Ala Gly Pro
                580                 585                 590

Thr Ser Ile Ser Ala Val Gly Val Leu Ala Pro His Ser Ala Leu Ala
            595                 600                 605

Val Leu Glu Asp Thr Val Asp Tyr Pro Ala Arg Ala His Thr Phe Asp
        610                 615                 620

Asp Phe Cys Pro Glu Cys Arg Ala Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Ser
            660

<210> SEQ ID NO 24
<211> LENGTH: 659
<212> TYPE: PRT
<213> ORGANISM: Hepatitis E virus

<400> SEQUENCE: 24

Met Arg Pro Arg Pro Leu Leu Leu Leu Phe Leu Leu Phe Leu Pro Met
1               5                   10                  15

Leu Pro Ala Pro Pro Thr Gly Gln Pro Ser Gly Arg Arg Arg Gly Arg
            20                  25                  30

Arg Ser Gly Gly Thr Gly Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Ala Ala Ala Ser Gly Ser Gly Pro Arg Leu Arg Gln Pro Ala
65                  70                  75                  80

Arg Pro Leu Gly Ser Thr Trp Arg Asp Gln Ala Gln Arg Pro Ser Ala
                85                  90                  95

Ala Ser Arg Arg Arg Pro Ala Thr Ala Gly Ala Ala Ala Leu Thr Ala
            100                 105                 110

Val Ala Pro Ala His Asp Thr Ser Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Ser Gly Thr Asn Leu Val Leu Tyr Ala Ala Pro Leu
145                 150                 155                 160

Asn Pro Pro Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Glu Ala Thr
            260                 265                 270
```

```
Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
290                 295                 300

Glu Leu Glu Phe Arg Asn Leu Thr Thr Cys Asn Thr Asn Thr Arg Val
305                 310                 315                 320

Ser Arg Tyr Ser Ser Thr Ala Arg His Ser Ala Arg Gly Ala Asp Gly
            325                 330                 335

Thr Ala Glu Leu Thr Thr Thr Ala Ala Thr Arg Phe Met Lys Asp Leu
                340                 345                 350

His Phe Thr Gly Leu Asn Gly Val Gly Glu Val Gly Arg Gly Ile Ala
            355                 360                 365

Leu Thr Leu Leu Asn Leu Ala Asp Thr Leu Leu Gly Gly Leu Pro Thr
        370                 375                 380

Glu Leu Ile Ser Ser Ala Gly Gly Gln Leu Phe Tyr Ser Arg Pro Val
385                 390                 395                 400

Val Ser Ala Asn Gly Glu Pro Thr Val Lys Leu Tyr Thr Ser Val Glu
            405                 410                 415

Asn Ala Gln Gln Asp Lys Gly Val Ala Ile Pro His Asp Ile Asp Leu
                420                 425                 430

Gly Asp Ser Arg Val Val Ile Gln Asp Tyr Asp Asn Gln His Glu Gln
            435                 440                 445

Asp Arg Pro Thr Pro Ser Pro Ala Pro Ser Arg Pro Phe Ser Val Leu
        450                 455                 460

Arg Ala Asn Asp Val Leu Trp Leu Ser Leu Thr Ala Ala Glu Tyr Asp
465                 470                 475                 480

Gln Ser Thr Tyr Gly Ser Ser Thr Gly Pro Val Tyr Ile Ser Asp Ser
            485                 490                 495

Val Thr Leu Val Asn Val Ala Thr Gly Ala Gln Ala Val Ala Arg Ser
                500                 505                 510

Leu Asp Trp Ser Lys Val Thr Leu Asp Gly Arg Pro Leu Pro Thr Val
        515                 520                 525

Glu Gln Tyr Ser Lys Thr Phe Phe Val Leu Pro Leu Arg Gly Lys Leu
        530                 535                 540

Ser Phe Trp Glu Ala Gly Thr Thr Lys Ala Gly Tyr Pro Tyr Asn Tyr
545                 550                 555                 560

Asn Thr Thr Ala Ser Asp Gln Ile Leu Ile Glu Asn Ala Ala Gly His
            565                 570                 575

Arg Val Ala Ile Ser Thr Tyr Thr Thr Arg Leu Gly Ala Gly Pro Val
                580                 585                 590

Ala Ile Ser Ala Ala Val Leu Ala Pro Arg Ser Ala Leu Ala Leu
        595                 600                 605

Leu Glu Asp Thr Phe Asp Tyr Pro Gly Arg Ala His Thr Phe Asp Asp
610                 615                 620

Phe Cys Pro Glu Cys Arg Ala Leu Gly Leu Gln Gly Cys Ala Phe Gln
625                 630                 635                 640

Ser Thr Val Ala Glu Leu Gln Arg Leu Lys Val Lys Val Gly Lys Thr
            645                 650                 655

Arg Glu Leu

<210> SEQ ID NO 25
<211> LENGTH: 12
<212> TYPE: PRT
```

<213> ORGANISM: artificial sequence
<220> FEATURE:
<223> OTHER INFORMATION: HEV peptide
<220> FEATURE:
<221> NAME/KEY: MISC_FEATURE
<222> LOCATION: (6)..(6)
<223> OTHER INFORMATION: X represents P, T, S or A
<220> FEATURE:
<221> NAME/KEY: MISC_FEATURE
<222> LOCATION: (9)..(9)
<223> OTHER INFORMATION: X represents L or F

<400> SEQUENCE: 25

Cys Pro Glu Cys Arg Xaa Leu Gly Xaa Gln Gly Cys
1               5                   10

<210> SEQ ID NO 26
<211> LENGTH: 267
<212> TYPE: PRT
<213> ORGANISM: Hepatitis E virus

<400> SEQUENCE: 26

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Ser Thr Tyr Gly Ser Ser Thr
                85                  90                  95

Gly Pro Val Tyr Val Ser Asp Ser Val Thr Leu Val Asn Val Ala Thr
            100                 105                 110

Gly Ala Gln Ala Val Ala Arg Ser Leu Asp Trp Thr Lys Val Thr Leu
        115                 120                 125

Asp Gly Arg Pro Leu Ser Thr Thr Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Leu
                165                 170                 175

Leu Val Glu Asn Ala Ala Gly His Arg Val Ala Ile Ser Thr Tyr Thr
            180                 185                 190

Thr Ser Leu Gly Ala Gly Pro Val Ser Ile Ser Ala Val Ala Val Leu
        195                 200                 205

Ala Pro His Ser Ala Leu Ala Leu Leu Glu Asp Thr Met Asp Tyr Pro
    210                 215                 220

Ala Arg Ala His Thr Phe Asp Asp Phe Cys Pro Glu Cys Arg Pro Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Leu
            260                 265

<210> SEQ ID NO 27
<211> LENGTH: 267

```
<212> TYPE: PRT
<213> ORGANISM: artificial sequence
<220> FEATURE:
<223> OTHER INFORMATION: HEV Peptide mut

<400> SEQU

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
        115                 120                 125

Asp Gly Arg Pro Leu Met Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ala Val Gly Val Leu
        195                 200                 205

Ala Pro His Ser Ala Leu Ala Ala Leu Glu Asp Thr Val Asp Tyr Pro
    210                 215                 220

Ala Arg Ala His Thr Phe Asp Asp Phe Cys Pro Glu Cys Arg Ala Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Tyr
            260                 265

<210> SEQ ID NO 29
<211> LENGTH: 267
<212> TYPE: PRT
<213> ORGANISM: artificial sequence
<220> FEATURE:
<223> OTHER INFORMATION: Hepatitis E virus

<400> SEQUENCE: 29

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
        115                 120                 125

Asp Gly Arg Pro Leu Thr Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

```
Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ser Val Gly Val Leu
        195                 200                 205

Ala Pro His Ser Ala Leu Ala Ala Leu Glu Asp Thr Val Asp Tyr Pro
    210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Tyr
                260                 265

<210> SEQ ID NO 30
<211> LENGTH: 267
<212> TYPE: PRT
<213> ORGANISM: artificial sequence
<220> FEATURE:
<223> OTHER INFORMATION: Hepatitis E virus

<400> SEQUENCE: 30

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
        115                 120                 125

Asp Gly Arg Pro Leu Thr Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ser Val Gly Val Leu
        195                 200                 205

Ala Pro His Ser Ala Leu Ala Ala Leu Glu Asp Thr Val Asp Tyr Pro
    210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Val Ala Glu Leu Gln Arg
                245                 250                 255
```

```
Leu Lys Met Lys Val Gly Lys Thr Arg Glu Tyr
        260                 265

<210> SEQ ID NO 31
<211> LENGTH: 267
<212> TYPE: PRT
<213> ORGANISM: artificial sequence
<220> FEATURE:
<223> OTHER INFORMATION: Hepatitis E virus

<400> SEQUENCE: 31

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
        115                 120                 125

Asp Gly Arg Pro Leu Met Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ala Val Gly Val Leu
        195                 200                 205

Ala Pro His Ser Ala Leu Ala Leu Glu Asp Thr Val Asp Tyr Pro
    210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Tyr
        260                 265

<210> SEQ ID NO 32
<211> LENGTH: 267
<212> TYPE: PRT
<213> ORGANISM: artificial sequence
<220> FEATURE:
<223> OTHER INFORMATION: Hepatitis E virus

<400> SEQUENCE: 32

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
```

```
                    20                  25                  30
Ala Ile Pro His Asp Ile Asp Leu Gly Glu Ser Arg Val Val Ile Gln
                35                  40                  45

Asp Tyr Asp Asn Gln His Glu Gln Asp Arg Pro Thr Pro Ser Pro Ala
            50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
        115                 120                 125

Asp Gly Arg Pro Leu Met Thr Ile Gln Gln Tyr Ser Lys Thr Phe Phe
        130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ala Val Gly Val Leu
        195                 200                 205

Ala Pro His Ser Ala Leu Ala Ala Leu Glu Asp Thr Val Asp Tyr Pro
        210                 215                 220

Ala Arg Ala His Thr Phe Asp Asp Phe Cys Pro Glu Cys Arg Ala Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Tyr
            260                 265

<210> SEQ ID NO 33
<211> LENGTH: 267
<212> TYPE: PRT
<213> ORGANISM: artificial sequence
<220> FEATURE:
<223> OTHER INFORMATION: Hepatitis E virus

<400> SEQUENCE: 33

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
                20                  25                  30

Ala Ile Pro His Asp Ile Asp Leu Gly Glu Ser Arg Val Val Ile Gln
                35                  40                  45

Asp Tyr Asp Asn Gln His Glu Gln Asp Arg Pro Thr Pro Ser Pro Ala
            50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
```

```
            115                 120                 125
Asp Gly Arg Pro Leu Thr Thr Ile Gln Gln Tyr Ser Lys Thr Phe Tyr
        130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ala Val Gly Val Leu
        195                 200                 205

Ala Pro His Ser Ala Leu Ala Val Leu Glu Asp Thr Val Asp Tyr Pro
    210                 215                 220

Ala Arg Ala His Thr Phe Asp Asp Phe Cys Pro Glu Cys Arg Ala Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Tyr
            260                 265

<210> SEQ ID NO 34
<211> LENGTH: 267
<212> TYPE: PRT
<213> ORGANISM: artificial sequence
<220> FEATURE:
<223> OTHER INFORMATION: Hepatitis E virus

<400> SEQUENCE: 34

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
                20                  25                  30

Ala Ile Pro His Asp Ile Asp Leu Gly Glu Ser Arg Val Val Ile Gln
            35                  40                  45

Asp Tyr Asp Asn Gln His Glu Gln Asp Arg Pro Thr Pro Ser Pro Ala
        50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
                100                 105                 110

Gly Ala Gln Gly Val Ser Arg Ser Leu Asp Trp Ser Lys Val Thr Leu
            115                 120                 125

Asp Gly Arg Pro Leu Thr Thr Ile Gln Gln Tyr Ser Lys Thr Phe Tyr
        130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ala Val Gly Val Leu
        195                 200                 205

Ala Pro His Ser Ala Leu Ala Ile Leu Glu Asp Thr Ala Asp Tyr Pro
```

Ala Arg Ala His Thr Phe Asp Asp Phe Cys Pro Glu Cys Arg Ser Leu
225                 230                 235                 240

Gly Leu Gln Gly Cys Ala Phe Gln Ser Thr Val Ala Glu Leu Gln Arg
            245                 250                 255

Leu Lys Met Lys Val Gly Lys Thr Arg Glu Tyr
        260                 265

<210> SEQ ID NO 35
<211> LENGTH: 267
<212> TYPE: PRT
<213> ORGANISM: artificial sequence
<220> FEATURE:
<223> OTHER INFORMATION: Hepatitis E virus

<400> SEQUENCE: 35

Gln Leu Phe Tyr Ser Arg Pro Val Val Ser Ala Asn Gly Glu Leu Thr
1               5                   10                  15

Val Lys Leu Tyr Thr Ser Val Glu Asn Ala Gln Gln Asp Lys Gly Val
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
        115                 120                 125

Asp Gly Arg Pro Leu Thr Thr Ile Gln Gln Tyr Ser Lys Thr Phe Tyr
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Val Ser Ala Val Gly Val Leu
        195                 200                 205

Ala Pro His Ser Ala Leu Ala Ala Leu Glu Asp Thr Ala Asp Tyr Pro
    210                 215                 220

Ala Arg Ala His Thr Phe Asp Asp Phe Cys Pro Glu Cys Arg Ala Leu
225                 230                 235                 240

Gly Leu Gln Gly Cys Ala Phe Gln Ser Thr Val Gly Glu Leu Gln Arg
            245                 250                 255

Leu Lys Met Lys Val Gly Lys Thr Arg Glu Tyr
        260                 265

<210> SEQ ID NO 36
<211> LENGTH: 267
<212> TYPE: PRT
<213> ORGANISM: artificial sequence
<220> FEATURE:
<223> OTHER INFORMATION: Hepatitis E virus

<400> SEQUENCE: 36

```
Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
        115                 120                 125

Asp Gly Arg Pro Leu Thr Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ala Val Gly Val Leu
        195                 200                 205

Ala Pro His Ser Ala Leu Ala Ala Leu Glu Asp Thr Val Asp Tyr Pro
    210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Tyr
            260                 265
```

<210> SEQ ID NO 37
<211> LENGTH: 264
<212> TYPE: PRT
<213> ORGANISM: artificial sequence
<220> FEATURE:
<223> OTHER INFORMATION: Hepatitis E virus

<400> SEQUENCE: 37

```
Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Gly Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80
```

```
Ser Leu Thr Ala Ala Glu Tyr Asp Gln Thr Thr Tyr Gly Ser Ser Thr
            85                  90                  95

Asn Pro Met Tyr Val Ser Asp Thr Val Thr Phe Val Asn Val Ala Thr
            100                 105                 110

Gly Ala Gln Gly Val Ser Arg Ser Leu Asp Trp Ser Lys Val Thr Leu
            115                 120                 125

Asp Gly Arg Ser Leu Thr Thr Ile Gln Gln Tyr Ser Lys Thr Phe Phe
            130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
            165                 170                 175

Leu Ile Glu Asn Ala Ala Gly His Arg Val Cys Ile Ser Thr Tyr Thr
            180                 185                 190

Thr Asn Leu Gly Ser Gly Pro Val Ser Ile Ser Ala Val Gly Val Leu
            195                 200                 205

Ala Pro His Ser Ala Leu Ala Val Leu Glu Asp Thr Val Asp Tyr Pro
            210                 215                 220

Ala Arg Ala His Thr Phe Asp Asp Phe Cys Pro Glu Cys Arg Ala Leu
225                 230                 235                 240

Gly Leu Gln Gly Cys Ala Phe Gln Ser Thr Val Ala Glu Leu Gln Arg
            245                 250                 255

Leu Lys Met Lys Val Gly Asn His
            260

<210> SEQ ID NO 38
<211> LENGTH: 267
<212> TYPE: PRT
<213> ORGANISM: artificial sequence
<220> FEATURE:
<223> OTHER INFORMATION: Hepatitis E virus

<400> SEQUENCE: 38

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
            35                  40                  45

Asp Tyr Asp Asn Gln His Glu Gln Asp Arg Pro Thr Pro Ser Pro Ala
        50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Ser Thr Tyr Gly Ser Ser Thr
            85                  90                  95

Gly Pro Val Tyr Val Ser Asp Ser Val Thr Leu Val Asn Val Ala Thr
            100                 105                 110

Gly Ala Gln Ala Val Ala Arg Ser Leu Asp Trp Thr Lys Val Thr Leu
            115                 120                 125

Asp Gly Arg Pro Leu Ser Thr Ile Gln Gln Tyr Ser Lys Thr Phe Phe
            130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Leu
            165                 170                 175
```

```
Leu Val Glu Asn Ala Ala Gly His Arg Val Ala Ile Ser Thr Tyr Thr
            180                 185                 190

Thr Ser Leu Gly Ala Gly Pro Val Ser Ile Ser Ala Val Ala Val Leu
        195                 200                 205

Ala Pro His Ser Ala Leu Ala Leu Leu Glu Asp Thr Leu Asp Tyr Pro
    210                 215                 220

Ala Arg Ala His Thr Phe Asp Asp Phe Cys Pro Glu Cys Arg Pro Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Leu
            260                 265

<210> SEQ ID NO 39
<211> LENGTH: 267
<212> TYPE: PRT
<213> ORGANISM: artificial sequence
<220> FEATURE:
<223> OTHER INFORMATION: Hepatitis E virus

<400> SEQUENCE: 39

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Thr Ile Pro His Asp Ile Asp Leu Gly Asp Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Leu Val Asn Val Ala Thr
            100                 105                 110

Gly Ala Gln Ala Val Ala Arg Ser Leu Asp Trp Ser Lys Val Thr Leu
        115                 120                 125

Asp Gly Arg Pro Leu Thr Thr Ile Gln Gln Tyr Ser Lys Thr Phe Tyr
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Ala Ile Ser Thr Tyr Thr
            180                 185                 190

Thr Ser Leu Gly Ala Gly Pro Thr Ser Ile Ser Ala Val Gly Val Leu
        195                 200                 205

Ala Pro His Ser Ala Leu Ala Val Leu Glu Asp Thr Val Asp Tyr Pro
    210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Ile Ala Glu Leu Gln Arg
                245                 250                 255

Leu Lys Met Lys Val Gly Lys Thr Arg Glu Ser
            260                 265
```

```
<210> SEQ ID NO 40
<211> LENGTH: 267
<212> TYPE: PRT
<213> ORGANISM: artificial sequence
<220> FEATURE:
<223> OTHER INFORMATION: Hepatitis E virus

<400> SEQUENCE: 40

Gln Leu Phe Tyr Ser Arg Pro Val Val Ser Ala His Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Ser Thr Tyr Gly Ser Ser Thr
                85                  90                  95

Ala Pro Val Tyr Val Ser Asp Ser Val Thr Leu Val Asn Val Ala Thr
            100                 105                 110

Gly Ala Gln Ala Val Ala Arg Ser Leu Asp Trp Thr Lys Val Thr Leu
        115                 120                 125

Asp Gly Arg Pro Leu Ser Thr Ile Gln Gln Tyr Pro Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Leu
                165                 170                 175

Leu Val Glu Asn Ala Ala Gly His Arg Val Ala Ile Ser Thr Tyr Thr
            180                 185                 190

Thr Ser Leu Gly Ala Gly Pro Val Ser Ile Ser Ala Val Ala Val Leu
        195                 200                 205

Ala Pro His Ser Ala Leu Ala Leu Leu Glu Asp Thr Leu Asp Tyr Pro
    210                 215                 220

Ala Cys Ala His Thr Phe Asp Asp Phe Cys Pro Glu Cys Arg Pro Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Leu
            260                 265

<210> SEQ ID NO 41
<211> LENGTH: 267
<212> TYPE: PRT
<213> ORGANISM: artificial sequence
<220> FEATURE:
<223> OTHER INFORMATION: Hepatitis E virus

<400> SEQUENCE: 41

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro Asn Asp Ile Asp Leu Gly Glu Ser Arg Val Val Ile Gln
        35                  40                  45
```

```
Asp Tyr Asp Asn Gln His Glu Gln Asp Arg Pro Thr Pro Ser Pro Ala
        50                  55                  60

Pro Ser Arg Pro Phe Ser Val Leu Arg Ala Asn Asp Val Leu Trp Leu
 65                  70                  75                  80

Ser Leu Thr Ala Ala Glu Tyr Asp Gln Ser Thr Tyr Gly Ser Ser Thr
                 85                  90                  95

Gly Pro Val Tyr Val Ser Asp Ser Val Thr Leu Val Asn Val Ala Thr
            100                 105                 110

Gly Ala Gln Ala Val Ala Arg Ser Leu Asp Trp Thr Lys Val Thr Leu
            115                 120                 125

Asp Gly Arg Pro Leu Ser Thr Ile Gln Gln Tyr Ser Lys Ile Phe Phe
        130                 135                 140

Val Leu Pro Leu Arg Gly Lys Leu Ser Phe Trp Glu Ala Gly Thr Thr
145                 150                 155                 160

Arg Pro Gly Tyr Pro Tyr Asn Tyr Asn Thr Thr Ala Ser Asp Gln Leu
                165                 170                 175

Leu Val Glu Asn Ala Ala Gly His Arg Val Ala Ile Ser Thr Tyr Thr
            180                 185                 190

Thr Ser Leu Gly Ala Gly Pro Val Ser Ile Ser Ala Val Ala Val Leu
        195                 200                 205

Gly Pro His Ser Ala Leu Ala Leu Leu Glu Asp Thr Leu Asp Tyr Pro
210                 215                 220

Ala Arg Ala His Thr Phe Asp Asp Phe Cys Pro Glu Cys Arg Pro Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Leu
            260                 265

<210> SEQ ID NO 42
<211> LENGTH: 267
<212> TYPE: PRT
<213> ORGANISM: artificial sequence
<220> FEATURE:
<223> OTHER INFORMATION: Hepatitis E virus

<400> SEQUENCE: 42

Gln Leu Phe Tyr Ser Arg Pro Val Val Ser Ala Asn Gly Glu Pro Thr
 1               5                  10                  15

Val Lys Leu Tyr Thr Ser Val Glu Asn Ala Gln Gln Asp Lys Gly Ile
             20                  25                  30

Thr Ile Pro His Asp Ile Asp Leu Gly Asp Ser Arg Val Val Ile Gln
             35                  40                  45

Asp Tyr Asp Asn Gln His Glu Gln Asp Arg Pro Thr Pro Ser Pro Ala
         50                 55                  60

Pro Ser Arg Pro Phe Ser Val Leu Arg Ala Asn Asp Val Leu Trp Leu
 65                 70                  75                  80

Ser Leu Thr Ala Ala Glu Tyr Asp Gln Thr Thr Tyr Gly Ser Ser Thr
                 85                  90                  95

Asn Pro Met Tyr Val Ser Asp Thr Val Thr Leu Val Asn Val Ala Thr
            100                 105                 110

Gly Ala Gln Ala Val Ala Arg Ser Leu Asp Trp Ser Lys Val Thr Leu
            115                 120                 125

Asp Gly Arg Pro Leu Thr Thr Ile Gln Gln Tyr Ser Lys Thr Phe Tyr
        130                 135                 140
```

```
Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Ala Ile Ser Thr Tyr Thr
            180                 185                 190

Thr Ser Leu Gly Ala Gly Pro Thr Ser Ile Ser Ala Val Gly Val Leu
        195                 200                 205

Ala Pro His Ser Ala Leu Ala Val Leu Glu Asp Thr Ile Asp Tyr Pro
    210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Ile Ala Glu Leu Gln Arg
                245                 250                 255

Leu Lys Met Lys Val Gly Lys Thr Arg Glu Ser
            260                 265

<210> SEQ ID NO 43
<211> LENGTH: 267
<212> TYPE: PRT
<213> ORGANISM: artificial sequence
<220> FEATURE:
<223> OTHER INFORMATION: Hepatitis E virus

<400> SEQUENCE: 43

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Ser Thr Tyr Gly Ser Ser Thr
                85                  90                  95

Gly Pro Val Tyr Val Ser Asp Ser Val Thr Leu Val Asn Val Ala Thr
            100                 105                 110

Gly Ala Gln Ala Val Ala Arg Ser Leu Asp Trp Thr Lys Val Thr Leu
        115                 120                 125

Asp Gly Arg Pro Leu Ser Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Leu
                165                 170                 175

Leu Val Glu Asn Ala Ala Gly His Arg Val Ala Ile Ser Thr Tyr Thr
            180                 185                 190

Thr Ser Leu Gly Ala Gly Pro Val Ser Ile Ser Ala Val Ala Val Leu
        195                 200                 205

Ala Pro His Ser Val Leu Ala Leu Leu Glu Asp Thr Met Asp Tyr Pro
    210                 215                 220

Ala Arg Ala His Thr Phe Asp Asp Phe Cys Pro Glu Cys Arg Pro Leu
225                 230                 235                 240
```

```
Gly Leu Gln Gly Cys Ala Phe Gln Ser Thr Val Ala Glu Leu Gln Arg
                245                 250                 255

Leu Lys Met Lys Val Gly Lys Thr Arg Glu Leu
            260                 265

<210> SEQ ID NO 44
<211> LENGTH: 267
<212> TYPE: PRT
<213> ORGANISM: artificial sequence
<220> FEATURE:
<223> OTHER INFORMATION: Hepatitis E virus
<220> FEATURE:
<221> NAME/KEY: misc_feature
<222> LOCATION: (88)..(88)
<223> OTHER INFORMATION: Xaa can be any naturally occurring amino acid

<400> SEQUENCE: 44

Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Thr Ile Pro His Asp Ile Asp Leu Gly Asp Ser Arg Val Val Ile Gln
        35                  40                  45

Asp Tyr Asp Asn Gln His Glu Gln Asp Arg Pro Thr Pro Ser Pro Ala
50                  55                  60

Pro Ser Arg Pro Phe Ser Val Leu Arg Ala Asn Asp Val Leu Trp Leu
65                  70                  75                  80

Ser Leu Thr Ala Ala Glu Tyr Xaa Gln Thr Thr Tyr Gly Ser Ser Thr
                85                  90                  95

Asn Pro Met Tyr Val Ser Asp Thr Val Thr Leu Val Asn Val Ala Thr
            100                 105                 110

Gly Ala Gln Ala Val Ala Arg Ser Leu Asp Trp Ser Lys Val Thr Leu
        115                 120                 125

Asp Gly Arg Pro Leu Thr Thr Ile Gln Gln Tyr Ser Lys Lys Phe Tyr
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Ala Ile Ser Thr Tyr Thr
            180                 185                 190

Thr Ser Leu Gly Ala Gly Pro Thr Ser Ile Ser Ala Val Gly Val Leu
        195                 200                 205

Ala Pro His Ser Ala Leu Ala Val Leu Glu Asp Thr Val Asp Tyr Pro
    210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Ile Ala Glu Leu Gln Arg
                245                 250                 255

Leu Lys Met Lys Val Gly Lys Thr Arg Glu Ser
            260                 265

<210> SEQ ID NO 45
<211> LENGTH: 267
<212> TYPE: PRT
<213> ORGANISM: artificial sequence
<220> FEATURE:
<223> OTHER INFORMATION: Hepatitis E virus
```

<400> SEQUENCE: 45

```
Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Thr Gln Gly Val Ser Arg Ser Leu Asp Trp Ser Lys Val Thr Leu
        115                 120                 125

Asp Gly Arg Pro Leu Thr Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Pro Gly His Arg Val Cys Ile Ser Thr Tyr Thr
            180                 185                 190

Thr Asn Leu Gly Ser Gly Pro Val Ser Ile Ser Ala Val Gly Val Leu
        195                 200                 205

Ala Pro His Ser Ala Leu Ala Ala Leu Glu Asp Thr Val Asp Tyr Pro
    210                 215                 220

Ala Arg Ala His Thr Phe Asp Asp Phe Cys Pro Glu Cys Arg Ala Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Gln Glu Tyr
            260                 265
```

<210> SEQ ID NO 46
<211> LENGTH: 267
<212> TYPE: PRT
<213> ORGANISM: artificial sequence
<220> FEATURE:
<223> OTHER INFORMATION: Hepatitis E virus

<400> SEQUENCE: 46

```
Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Ala Ile Pro His Asp Ile Asp Leu Gly Glu Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80
```

Ser Leu Thr Ala Ala Glu Tyr Asp Gln Ser Thr Tyr Gly Ser Ser Thr
                85                  90                  95

Gly Pro Val Tyr Val Ser Asp Ser Val Thr Leu Val Asn Val Ala Thr
            100                 105                 110

Gly Ala Gln Ala Val Ala Arg Ser Leu Asp Trp Thr Lys Val Thr Leu
        115                 120                 125

Asp Gly Arg Pro Leu Ser Thr Ile Gln Gln Tyr Ser Lys Thr Phe Phe
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Leu
                165                 170                 175

Leu Ile Glu Asn Ala Ala Gly His Arg Val Ala Ile Ser Thr Tyr Thr
            180                 185                 190

Thr Ser Leu Gly Ala Gly Pro Val Ala Ile Ser Ala Val Ala Val Leu
        195                 200                 205

Ala Pro His Ser Ala Leu Ala Leu Leu Glu Asp Thr Met Asp Tyr Pro
    210                 215                 220

Ala Arg Ala His Thr Phe Asp Asp Phe Cys Pro Glu Cys Arg Pro Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Leu
                260                 265

<210> SEQ ID NO 47
<211> LENGTH: 267
<212> TYPE: PRT
<213> ORGANISM: artificial sequence
<220> FEATURE:
<223> OTHER INFORMATION: Hepatitis E virus

<400> SEQUENCE: 47

Gln Leu Phe Tyr Ser Arg Pro Val Ala Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Thr Ile Pro His Asp Ile Asp Leu Gly Asp Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Val Ala Glu Tyr Asp Gln Thr Thr Tyr Gly Ser Ser Thr
                85                  90                  95

Asn Pro Met Tyr Val Ser Asp Thr Ala Thr Phe Val Asn Val Ala Thr
            100                 105                 110

Gly Ala Gln Ala Val Ala Arg Ser Leu Asp Trp Ser Lys Val Thr Leu
        115                 120                 125

Asp Gly Arg Pro Leu Thr Thr Ile Gln Gln Tyr Ser Lys Thr Phe Tyr
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Ala Ala Ser Asp Gln Ile
                165                 170                 175

```
Leu Ile Glu Asn Ala Ala Gly His Arg Val Ala Ile Ser Thr Tyr Thr
            180                 185                 190

Thr Ser Leu Gly Ala Ser Pro Thr Ser Ile Ser Ala Val Gly Val Leu
            195                 200                 205

Ala Pro His Ser Ala Leu Ala Val Leu Glu Asp Thr Val Asp Tyr Pro
            210                 215                 220

Ala Arg Ala His Thr Phe Asp Asp Phe Cys Pro Glu Cys Arg Thr Leu
225                 230                 235                 240

Gly Leu Gln Gly Cys Ala Phe Gln Ser Thr Ile Ala Glu Leu Gln Arg
                245                 250                 255

Leu Lys Met Lys Val Gly Lys Thr Arg Glu Ser
            260                 265
```

<210> SEQ ID NO 48
<211> LENGTH: 267
<212> TYPE: PRT
<213> ORGANISM: artificial sequence
<220> FEATURE:
<223> OTHER INFORMATION: Hepatitis E virus

<400> SEQUENCE: 48

```
Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Thr Ile Pro His Asp Ile Asp Leu Gly Asp Ser Arg Val Val Ile Gln
            35                  40                  45

Asp Tyr Asp Asn Gln His Glu Gln Asp Arg Pro Thr Pro Ser Pro Ala
        50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Leu Val Asn Val Ala Thr
            100                 105                 110

Gly Ala Gln Ala Val Ala Arg Ser Leu Asp Trp Ser Lys Val Thr Leu
            115                 120                 125

Asp Gly Arg Pro Leu Thr Thr Ile Gln Gln Tyr Ser Lys Thr Phe Tyr
        130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ser Gly His Arg Val Ala Ile Ser Thr Tyr Thr
            180                 185                 190

Thr Ser Leu Gly Ala Gly Pro Thr Ser Ile Ser Ala Val Gly Val Leu
            195                 200                 205

Ala Pro His Ser Ala Leu Ala Val Leu Glu Asp Thr Ile Asp Tyr Pro
            210                 215                 220

Ala Arg Ala His Thr Phe Asp Asp Phe Cys Pro Glu Cys Arg Ala Leu
225                 230                 235                 240

Gly Phe Gln Gly Cys Ala Phe Gln Ser Thr Ile Ala Glu Leu Gln Arg
                245                 250                 255

Leu Lys Met Lys Val Gly Lys Thr Arg Glu Ser
            260                 265
```

<210> SEQ ID NO 49
<211> LENGTH: 267
<212> TYPE: PRT
<213> ORGANISM: artificial sequence
<220> FEATURE:
<223> OTHER INFORMATION: Hepatitis E virus

<400> SEQUENCE: 49

```
Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Ile
            20                  25                  30

Thr Ile Pro His Asp Ile Asp Leu Gly Asp Ser Arg Val Val Ile Gln
        35                  40                  45

Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65                  70                  75                  80

Ser Leu Thr Ala Ala Glu Tyr Asp Gln Thr Thr Tyr Gly Ser Ser Thr
                85                  90                  95

Asn Pro Met Tyr Val Ser Asp Thr Val Thr Phe Val Asn Val Ala Thr
            100                 105                 110

Gly Ala Gln Ala Val Ala Arg Ser Leu Asp Trp Ser Lys Val Thr Leu
        115                 120                 125

Asp Gly Arg Pro Leu Thr Thr Ile Gln Gln Tyr Ser Lys Thr Phe Tyr
    130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Ile
                165                 170                 175

Leu Ile Glu Asn Ala Ala Gly His Arg Val Ala Ile Ser Thr Tyr Thr
            180                 185                 190

Thr Ser Leu Gly Ala Gly Pro Thr Ser Ile Ser Ala Val Gly Val Leu
        195                 200                 205

Ala Pro His Ser Ala Leu Ala Val Leu Glu Asp Thr Val Asp Tyr Pro
    210                 215                 220

Ala Arg Ala His Thr Phe Asp Asp Phe Cys Pro Glu Cys Arg Ala Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Ser
            260                 265
```

<210> SEQ ID NO 50
<211> LENGTH: 267
<212> TYPE: PRT
<213> ORGANISM: artificial sequence
<220> FEATURE:
<223> OTHER INFORMATION: Hepatitis E virus

<400> SEQUENCE: 50

```
Gln Leu Phe Tyr Ser Arg Pro Val Val Ser Ala Asn Gly Glu Pro Thr
1               5                   10                  15

Val Lys Leu Tyr Thr Ser Val Glu Asn Ala Gln Gln Asp Lys Gly Val
            20                  25                  30

Ala Ile Pro His Asp Ile Asp Leu Gly Asp Ser Arg Val Val Ile Gln
        35                  40                  45
```

-continued

```
Asp Tyr Asp Asn Gln His Glu Gln Asp Arg Pro Thr Pro Ser Pro Ala
    50                  55                  60

Pro Ser Arg Pro Phe Ser Val Leu Arg Ala Asn Asp Val Leu Trp Leu
65              70                  75                      80

Ser Leu Thr Ala Ala Glu Tyr Asp Gln Ser Thr Tyr Gly Ser Ser Thr
                85                  90                  95

Gly Pro Val Tyr Ile Ser Asp Ser Val Thr Leu Val Asn Val Ala Thr
                100             105                 110

Gly Ala Gln Ala Val Ala Arg Ser Leu Asp Trp Ser Lys Val Thr Leu
            115             120                 125

Asp Gly Arg Pro Leu Pro Thr Val Glu Gln Tyr Ser Lys Thr Phe Phe
    130             135                 140

Val Leu Pro Leu Arg Gly Lys Leu Ser Phe Trp Glu Ala Gly Thr Thr
145             150                 155                     160

Lys Ala Gly Tyr Pro Tyr Asn Tyr Asn Thr Thr Ala Ser Asp Gln Ile
                165             170                 175

Leu Ile Glu Asn Ala Ala Gly His Arg Val Ala Ile Ser Thr Tyr Thr
                180             185                 190

Thr Arg Leu Gly Ala Gly Pro Val Ala Ile Ser Ala Ala Ala Val Leu
        195             200                 205

Ala Pro Arg Ser Ala Leu Ala Leu Leu Glu Asp Thr Phe Asp Tyr Pro
    210             215                 220

Gly Arg Ala His Thr Phe Asp Asp Phe Cys Pro Glu Cys Arg Ala Leu
225             230                 235                     240

Gly Leu Gln Gly Cys Ala Phe Gln Ser Thr Val Ala Glu Leu Gln Arg
                245             250                 255

Leu Lys Val Lys Val Gly Lys Thr Arg Glu Leu
                260             265
```

MUTATED HEV POLYPEPTIDES AND THE USE THEREOF FOR ASSAYING ANTI-HEV ANTIBODIES

The present invention relates to the field of hepatitis E virus (HEV) infections. In particular, the invention relates to the detection of hepatitis caused by the hepatitis E virus.

Hepatitis is inflammatory lesions of the liver, of which there may be many causes: infectious, drug-related, auto-immune, etc. Acute hepatic damage of viral origin is frequent, often asymptomatic. It is due either to a direct cytopathic action of the virus, or, usually, to the immune reaction directed against the infected hepatic cells. The symptoms, when they exist, combine febrile, pruritic jaundice, a discoloration of the stools, browning of the urine and a more or less large increase in transaminases, attesting to the cytolysis and the hepatic dysfunction.

Many viruses are capable of causing hepatic lesions, for example Epstein-Barr virus (EBV) or the cytomegalo virus (CMV), but only six viruses are acknowledged to be responsible for what is commonly referred to as "viral hepatitis". These viruses are the hepatitis A, B, C, Delta, E and G viruses, which are viruses belonging to very different families.

The hepatitis G virus is not very widely described.

The hepatitis A virus, or HAV, belongs to the Picornaviridae family and is the only one which represents the Hepato virus genus. It is a naked RNA virus. The virus reservoir is the infected subject, who may or may not be ill. The modes of transmission are determined by the exceptional resistance of the virus and its high concentration in the stools. The principal mode of transmission is essentially fecal-oral. A particular risk is associated with the consumption of shellfish and unclean raw vegetables.

The hepatitis B virus, or HBV, belongs to the hepadnaviridae family. It is a circular DNA virus which is double-stranded over ¾ of its circumference. This virus exposes to the risk of fulminant hepatitis, active chronic hepatitis, cirrhosis and hepatocarcinoma. The principal vector of the virus is the blood, but it can be transmitted sexually. Worldwide, the number of individuals chronically infected with this virus is estimated at 350 million and it is estimated to be responsible for more than one million deaths annually.

The hepatitis C virus, or HCV or NANBH for "Non-A, Non-B Hepatitis", which is a virus with an RNA genome of positive polarity, has an organization close to that of flaviviruses with 9500 nucleotides (9.5 kb), non-coding 5' and 3' ends, and, starting from the 5' end, capsid (C), envelope (E1 and E2) and non-structural protein (NS1 to NS5) genes. HCV is a strictly human virus. The mode of contamination is principally the venous route, for example through using non-sterilized needles, contamination by blood transfusion still being present in developing countries where there is no screening of donors. The most worrying element of hepatitis C is that, beyond a generally asymptomatic primary infection (90% of cases), it progresses 70 to 80% of cases toward chronicity, with, in 20% of chronically infected individuals, a risk of cirrhosis and of primary liver cancer after an incubation of on average 20 years for cirrhosis and 30 years for cancer.

The hepatitis DELTA virus, or HDV, is a very small RNA virus which is incapable of replicating without HBV, which loans it its HBs surface antigen. Infection with DELTA virus occurs only at the same time as an HBV infection, the prognosis of which is as a result worsened: increased risk of fulminant hepatitis and progression to active chronic hepatitis.

The hepatitis E virus, or HEV or ET-NANBH for "Enterically Transmitted Non-A, Non-B Hepatitis", is a small non-enveloped naked virus, the genome of which is a single-stranded RNA of positive polarity. Initially classed in the Caliciviridae family to which it is similar, knowledge of its entire genome has today led to it being classified on its own, as the only member of the *Hepevirus* genus, of the Hepeviridcae family (Emerson, S. U., & Purcell, R. H., 2007). The inter-human transmission of this virus takes place principally via the fecal-oral route (dirty water, food). Infections are endemic in certain regions of Asia, Africa and Central and South America. The hepatitis E virus is identified as the principal agent of epidemics of acute hepatitis in countries with a low hygiene level. More recently, it has been clearly defined as being responsible for actual sporadic cases of acute hepatitis in industrialized countries in patients who have never spent time in an endemic zone. It is currently clearly demonstrated that hepatitis E is a zoonosis and that numerous domestic and wild animal species are infected with HEV, constituting the virus reservoir. Hepatitis E, like hepatitis A, does not generally progress to chronicity, except for certain groups of patients such as those who have received a solid organ transplant. However, it has one poorly explained particularity: although it is generally spontaneously resolved, it has been observed that, in India, mortality could reach 20% in pregnant women, as the gestational age increases, which could make HEV infection the most serious hepatitis of all the types of viral hepatitis during pregnancy. It is therefore essential to have available effective and reliable tools for detecting HEV infection.

The genome of the hepatitis E virus has an approximate length of 7.5 kb and has 3 partially overlapping reading frames (ORF1, ORF2 and ORF3) framed at the 5' end by a non-coding sequence of 27 to 32 nucleotides and at the 3' end by a sequence of 65 to 74 bases, followed by a polyadenylated end of variable length depending on the virus. ORF1 encodes a polyprotein of approximately 186 kDa, called p-ORF1 protein, which is subsequently cleaved into non-structural proteins, including a methyl transferase, demonstrating that the virus is capped at its 5' end, and the RNA-dependent RNA polymerase. ORF2 encodes the glycosylated capsid protein, called p-ORF2 protein, having from 659 to 674 amino acids depending on the variants described to date, the majority of the p-ORF2 proteins of the variants having 660 amino acids. This p-ORF2 protein has several immunogenic sites, including a conformational immunodominant epitope between the amino acids 394 and 457, numbered in relation to the protein of 660 amino acids, and a target epitope for neutralizing antibodies, which is also conformational, located between amino acids 452 and 617, with the same numbering (Meng J, et al., 2001). It also comprises another immunodominant epitope, called epitope 406.3-2, which corresponds to amino acids 613-654 of an ORF2 variant of 660 amino acids (WO 93/14116). The phosphoprotein having a molecular weight of 13 kDa, encoded by ORF3, called p-ORF3 protein, is very variable depending on the virus. This protein, the role of which remains to be specified, appears to be involved in viral replication regulation functions or in nucleocapsid assembly.

Current diagnosis is based either on detection of the virus by gene amplification from stool and serum samples, or even bile or liver biopsy, or on detection of the anti-HEV serum antibody response.

The gene amplification is carried out by RT-PCR, nested PCR or real-time PCR using several pairs of primers according to genotypes, from the most conserved regions of the genome. With a detection threshold of from 10 to $10^3$ cDNA molecules/reaction, depending on techniques, the viral excretion in the stools can reach $10^6$ cDNA molecules. The genotype can be characterized in a second step. These techniques are essentially of use for detecting viremia in the blood early on compared with infection, before the appearance of symptoms and antibodies. However, these techniques which target the detection of the viral nucleic acids have the drawbacks that the period of viremia is short (1 to 2 weeks in the blood, 3 to 4 weeks in the stools) and that they require expensive equipment that cannot be used very close to the patient.

The serological diagnosis of HEV infection is based on the detection of specific anti-HEV antibodies of IgM and/or IgG type, the principal target of which is p-ORF2. Several kits are commercially available. Thus, the company MP Diagnostic™ proposes the ASSURE® HEV IgM kit which is an immunochromatographic testing device intended for rapid detection of IgM antibodies directed against the p-ORF2 protein of the hepatitis E virus. To do this, the kit uses a recombinant polypeptide, the polypeptide 394-660, numbered in relation to the sequence 1-660 of p-ORF2, otherwise known as p-ORF2.1 polypeptide, corresponding to the final 267 amino acids of the protein. Mouse antibodies directed against human IgMs are immobilized on the immunochromatography membrane, thereby making it possible to capture the various human IgMs present in the sample. The presence of IgMs directed specifically against HEV is revealed using, as detection partner, the recombinant polypeptide 394-660 complexed to a gold-labeled anti-HEV monoclonal antibody. The reasons for the use of the recombinant polypeptide 394-660 rather than the whole protein are disclosed in application WO 95/08632. According to the teachings of this patent application, the immunological reactivity of the complete p-ORF2 protein expressed in *E. coli* is not optimal, one part of the molecule possibly reducing or even inhibiting the immunoreactivity of another part of the molecule. To overcome this inhibitory effect, patent application WO 95/08632 proposed using deleted or truncated p-ORF2 proteins. Among the various constructs tested, the recombinant polypeptide 394-660, deleted of the first 393 amino acids, exhibited the best immunoreactivity.

The detailed characterization of the antigenic structure of the polypeptide 394-660 and comparison thereof with that of the virus-like particles or VLPs, formed by self-assembly in vitro and antigenically close to the HEV viral particle, are described in Riddell M. A., et al., 2000.

The drawback of using the polypeptide 394-660 is that it contains, in its C-terminal part, a domain which at least partially inhibits the self-assembly of the polypeptide into oligomers and VLPs. This can interfere with the correct presentation of the conformational epitopes.

In order to overcome these drawbacks, the company Wantai modified the polypeptide 394-660 by deleting amino acids 607-660 (numbered in relation to a sequence 1-660 of p-ORF2) which interfere with the oligomerization and the self-assembly capacity. The polypeptide thus obtained was called polypeptide pE2, as described in patent application WO 01/22916. The advantage of this polypeptide pE2, of sequence 394-606, is that it naturally dimerizes and that the immunoreactivity of the dimeric pE2 is much higher than that of the monomeric pE2, promoting correct presentation of the conformational epitopes. The drawback is that such a truncated polypeptide does not comprise a large epitope, the epitope 406.3-2 corresponding to amino acids 613-654 of an ORF2 variant of 660 amino acids, as indicated in patent application WO 93/14116. Such a deletion can therefore result in a decrease in the sensitivity of a diagnostic test using such a truncated polypeptide.

The applicant has discovered, against all expectations, that it is possible to overcome the drawbacks of the prior art polypeptides by carrying out, in the HEV ORF2 peptide 394-660, numbered in relation to a p-ORF2 protein of 660 amino acids, 3 mutations at positions 627, 630 and 638, this being while improving its antigenicity and its immunoreactivity. Thus, the mutated peptide, which can be called p-ORF2-MUT, has all the large epitopes, dimerizes naturally in a non-covalent manner, is capable of oligomerizing without any aggregation and has an immunoreactivity greater than that of the non-mutated recombinant polypeptide 394-660.

Thus, the invention relates to a polypeptide derived from the p-ORF2 protein of the hepatitis E virus, comprising (i) at least the amino acid sequence 394-660, numbered in relation to a p-ORF2 protein of 660 amino acids, in which the three cysteines at positions 627, 630 and 638 have been mutated, or (ii) for a p-ORF2 protein of different length, at least the amino acid sequence corresponding to amino acids 394-660 of the p-ORF2 protein of 660 amino acids, in which the three cysteines located at the three positions corresponding to positions 627, 630 and 638 of the p-ORF2 protein of 660 amino acids have been mutated.

Another subject of the invention relates to the isolated nucleic acids comprising a nucleotide sequence encoding the polypeptides of the invention or a sequence complementary to said coding sequence, and also the expression vectors comprising these sequences.

Yet another subject relates to the host cells comprising these same nucleic sequences, inserted directly or by means of the expression vectors.

In addition, it relates to the use of the polypeptides of the invention for determining the presence of an antibody response directed against the p-ORF2 protein of the hepatitis E virus or else for determining the titer of these antibodies.

Thus, another subject of the invention relates to a method for determining, by immunoassay, the presence of an antibody response directed against the p-ORF2 protein of the hepatitis E virus in a biological sample from a subject, which may contain the antibodies of said response, which method comprises the following steps:
  bringing said biological sample into contact with a polypeptide of the invention,
  detecting a signal emitted by the binding between said polypeptide and said antibodies, if they are present, using a label capable of emitting a detectable signal,
  comparing the signal thus obtained with a reference signal S predetermined with two populations of controls, one having developed said antibodies and the other not having developed said antibodies,
  a signal lower than said reference signal S signifying that the sample does not contain said antibodies, and
  a signal higher than said reference signal S signifying that the sample contains said antibodies.

Another subject also relates to a method for determining, by immunoassay, the titer of antibodies directed against the p-ORF2 protein of the hepatitis E virus in a biological sample from a subject, which may contain said antibodies, which method comprises the following steps:
  bringing said biological sample into contact with a polypeptide of the invention,
  detecting a signal emitted by the bonding between said polypeptide and said antibodies, if they are present, using a label capable of emitting a detectable signal,
  converting the detected signal into an antibody titer.

Yet another subject relates to the use of these methods for assisting with in vitro diagnosis, for the in vitro diagnosis of a hepatitis E virus infection in a subject who may be infected, for therapeutic monitoring of a subject infected with the hepatitis E virus, for carrying out epidemiological studies of the sero prevalence of anti-HEV antibodies in a population or in a given geographic territory or for determining whether a subject needs to be vaccinated or revaccinated against the hepatitis E virus.

Finally, a last subject relates to the kits for determining, by immunoassay, the presence of the humoral response or of the titer of antibodies directed against the p-ORF2 protein of the hepatitis E virus in a subject who may have produced these antibodies, comprising a polypeptide of the invention.

The invention will be understood more clearly on reading the nonlimiting description which follows and the appended FIGS. 1 to 6, in which:

FIG. 1 gives an alignment of amino acid sequences of various p-ORF2 proteins of the principal HEV virus variants obtained from the Uniprot database, the first column corresponding to the UNIPROT reference, the second column corresponding to the name of the HEV strain and the last column corresponding to the sequence alignment. The sequence alignment was carried out using the Clustal Omega program accessible on the UNIPROT website. The last line under each sequence alignment shows the amino acid identity or non-identity between each variant, "*" indicating a totally conserved position, with the amino acids which are identical in all the variants, ":" indicating a very conserved position, with amino acids having strongly similar properties and a score >0.5 in the Gonnet PAM 250 matrix, "." indicating quite a conserved position, with amino acids having weakly similar properties and a score=<0.5 in the Gonnet PAM 250 matrix. The other positions are marked with "º". The various parts of the alignment are distributed from FIGS. 1A to 1R. FIGS. 1A to 1L give the alignment of the whole proteins of the different variants. The sequence 394-660 of the Q81871 variant, of 660 amino acids (SEQ ID No. 11), is underlined therein as reference. The arrows on FIG. 1G indicate the first amino acid of the minimal sequence of the polypeptides of the invention and the rectangle on FIG. 1K shows the sequence of 12 amino acids of the Q81871 variant in which are the 3 cysteines to be mutated. FIGS. 1M to 1R give the alignment of the minimal sequences of the polypeptides of the invention of the different variants extracted from FIGS. 1A to 1L starting from the arrows. The sequence 394-660 of the reference polypeptide of the Q81871 variant (SEQ ID No. 26) is underlined.

FIG. 2 shows the representations of the electron density maps of the side chains of natural amino acids, obtained by X-ray diffraction, calculated at a resolution of 1.5 Angstrom, printed from the website (reference dated Nov. 13, 2015): http://people.mbi.ucla.edu/sawaya/m230d/Modelbuilding/modelbuilding.html.

Figure 3:
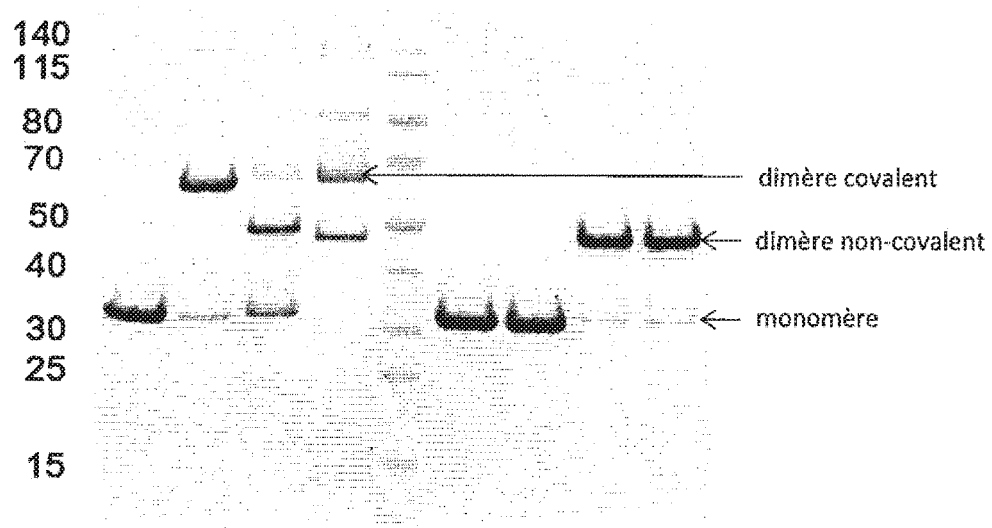

FIG. 3 is the photograph of a (4-12%) SDS-PAGE analysis gel stained with Coomassie blue in order to visualize a polypeptide of the invention, ORF2-MUT, and a non-mutated polypeptide, ORF2-REF which corresponds to the polypeptide p-ORF2.1 (amino acids 394-660) disclosed in application WO 95/08632. Before the analysis on gel, the purified and dialyzed polypeptides ORF2-REF and ORF2-MUT were subjected either to a reduction by addition of dithiothreitol (DTT), or a denaturation by heating (10 min at 75° C.), or both treatments at the same time, or no treatment, as shown in the table above the gel. The line M corresponds to the Page Ruler molecular weight marker (Pierce), the apparent molecular weights of the bands are indicated on the left in kilo Daltons (kDa).

FIG. 4 represents the size exclusion chromatograms obtained by following the UV absorbance at 280 nm for the prior art polypeptide ORF2-REF (FIG. 4A) and the polypeptide of the invention ORF2-MUT (FIG. 4B). In order to allow good visualization of the various peaks of FIG. 4A, the two chromatograms are not presented at the same scale for the y-axis.

Figure 5:
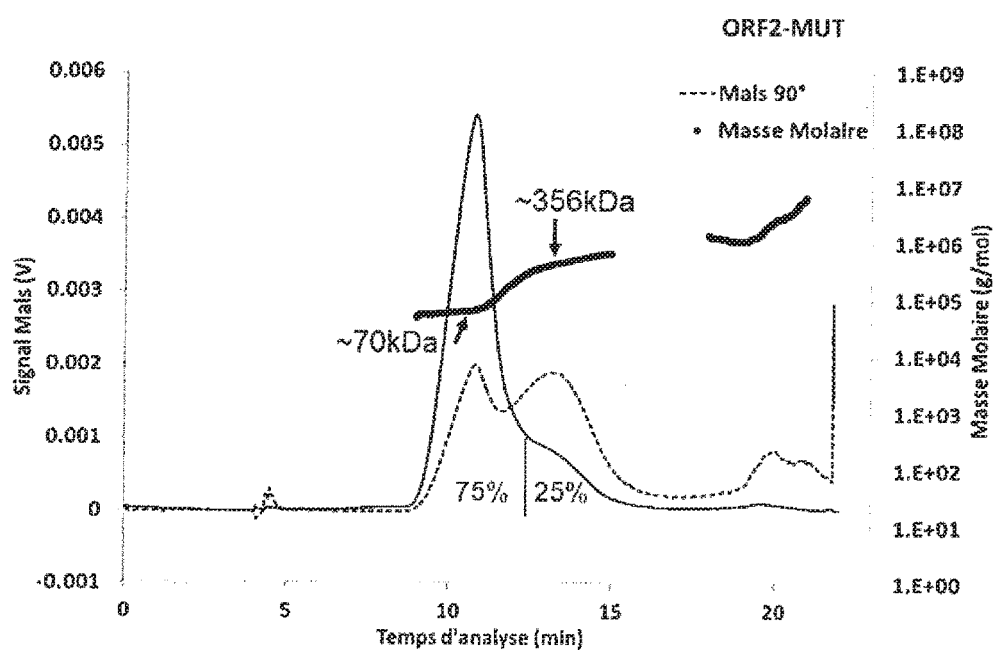

FIG. 5 represents the graph giving the results obtained using the AsFlFFF-MALS ("asymmetric flow field flow fractionation-multi angle light scattering") technique for the polypeptide of the invention ORF2-MUT. The UV absorbance at 280 nm (thin solid line), the multi-angle light scattering signal (MALS, hatched line) and the molar mass estimation (thick solid line) are represented superimposed in the y-axis as a function of the analysis time (min).

Figure 6:
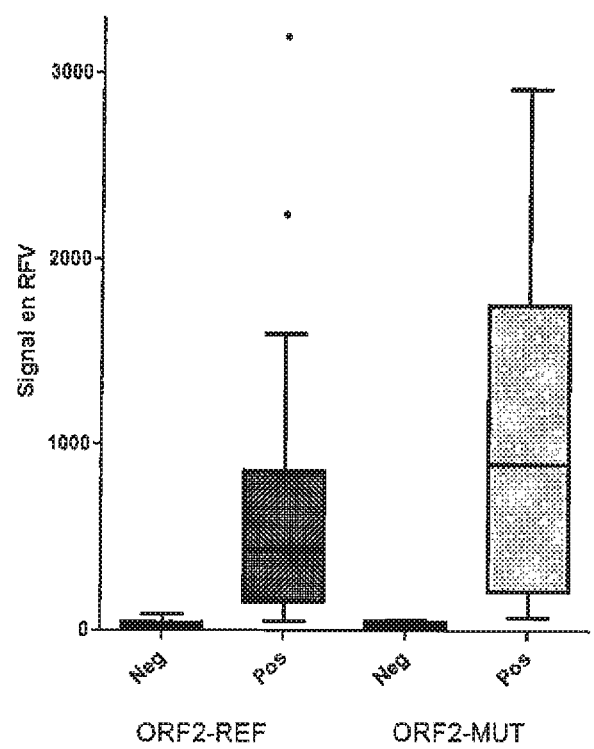

FIG. 6 is a box plot representation of the distributions of the RFV signals obtained with an immunoassay (VIDAS® automated device, bioMérieux) using, as capture antigen, the prior art polypeptide ORF2-REF or the polypeptide of the invention ORF2-MUT, on samples not containing anti-ORF2 antibodies (Neg) and REV-positive samples containing anti-ORF2 antibodies (Pos). The box plots were plotted according to the Tukey method: the high and low limits of the box correspond to the $25^{th}$ and $75^{th}$ percentile of the distributions, respectively. The value plotted around half the box is the median. The high plot corresponds to the $75^{th}$ percentile+1.5× the interquartile range and the low plot corresponds to the $25^{th}$ percentile−1.5× the interquartile range. The values above and below the plots are represented in the form of individual points since they are extreme values that are not very common.

The applicant has shown, against all expectations, that it was possible, with a view to treating subjects with a hepatitis E infection, to use polypeptides derived from the p-ORF2 protein of the hepatitis E virus, comprising at least the amino acid sequence 394-660, numbered in relation to a p-ORF2 protein of 660 amino acids, while at the same time avoiding the drawbacks of the prior art when amino acids 607-660 are included in the polypeptides, namely that they all have the large epitopes, naturally dimerize in a non-covalent manner, and are capable of oligomerizing without any aggregation. Moreover, the polypeptides of the invention are produced homogeneously, contrary to the prior art polypeptides. Indeed, during their production, the final product reproducibly exhibits more than 75% of non-covalent dimers, the remainder consisting of dodecamers, whereas the proportion of non-covalent dimers, covalent dimers and aggregates of the prior art polypeptides varies from one population to another. Furthermore, the polypeptides of the invention have an immunoreactivity greater than that of the non-mutated recombinant polypeptide 394-660. Finally, the polypeptides of the invention make it possible, when they are used in a immunoassay, to increase the diagnostic specificity of the test, without modifying the diagnostic sensitivity thereof, which is essential for a test for detecting the hepatitis E virus.

As previously indicated and as previously illustrated in FIG. 1, the p-ORF2 protein of the HEV virus has various lengths, from 659 to 674 amino acids (see FIG. 1L giving the last amino acids of the p-ORF2 protein). Since the majority of the proteins have 660 amino acids, it is a protein of 660 amino acids which is often taken as reference. In the present application, the reference sequence of 660 amino acids is that of the Q81871 variant (SEQ ID No. 11). However, the proteins of the other variants, although they have a different amino acid sequence, for example of 674 amino acids (SEQ ID Nos. 1 to 7), of 672 amino acids (SEQ ID No. 8), of 671 amino acids (SEQ ID No. 9), of 668 amino acids (SEQ ID No. 10) or of 659 amino acids (SEQ ID No. 24), and also those of the variants of which the protein has the same length (SEQ ID Nos. 12 to 23) are indeed included in the scope of the invention.

Thus, in order to find all the polypeptides of the invention, which are defined as comprising:
- when the p-ORF2 protein has 660 amino acids, at least the amino acid sequence 394-660, numbered in relation to a p-ORF2 protein of 660 amino acids, in which the three cysteines at positions 627, 630 and 638 are mutated, and
- when the p-ORF2 protein is of a different length, at least the amino acid sequence corresponding to amino acids 394-660 of the p-ORF2 protein of 660 amino acids, in which the three cysteines located in the three positions corresponding to positions 627, 630 and 638 of the p-ORF2 protein of 660 amino acids are mutated, it is sufficient for those skilled in the art to perform an alignment with respect to a protein of 660 amino acids. Thus, for example, if reference is made to FIG. 1, whether the protein belonging to the Q81871 variant (in which the sequence 394-660 is underlined in FIG. 1) is taken as reference protein of 660 amino acids and, for example, the proteins of the variants of 672, 671, 659, 668 and 674 amino acids are considered, the polypeptides of the invention comprise at least:
- the amino acid sequence 394-660 (SEQ ID No. 26, and SEQ ID Nos. 38 to 49) of which the cysteines at positions 627, 630 and 638 are mutated (derived from the variants Q81871, P29326, Q6J8F7, Q04611, Q68965, Q9YLQ9, P33426, Q9YLR2, Q0QC51, Q69411, A0A024D9U6, A0A024D9R2, Q8V729), or
- the amino acid sequence 408-674 (SEQ ID Nos. 28 to 34) of which the cysteines at positions 641, 644 and 652 are mutated (derived from the variants Q8JJN2, Q80IR5, Q806D7, Q6BD83, Q6BD78, B6VC89, Q6PMR3),
- the amino acid sequence 406-672 (SEQ ID No. 35) of which the cysteines at positions 639, 642 and 650 are mutated (derived from the Q9IVZ8 variant), or
- the amino acid sequence 405-671 (SEQ ID No. 36) of which the cysteines at positions 638, 641 and 649 are mutated (derived from the Q8JJM1 variant), or
- the amino acid sequence 405-668 (SEQ ID No. 37) of which the cysteines at positions 638, 641 and 649 are mutated (derived from the Q2PYP3 variant), or
- the amino acid sequence 393-659 (SEQ ID No. 50) of which the cysteines at positions 626, 629 and 637 are mutated (derived from the Q03500 variant).

Thus, the various fragments 394-660, 408-674, 406-672, 405-671, 405-668 and 393-659 of the variants described in FIGS. 1M to 1R and extracted from FIGS. 1G to 1L, starting from the arrow in FIG. 1G, correspond to the following sequences:

| Fragments 394-660 | | | | | |
|---|---|---|---|---|---|
| Q81871 | P29326 | Q6J8F7 | Q04611 | Q68985 | Q9YLQ9 |
| SEQ ID No. 26 | SEQ ID No. 38 | SEQ ID No. 39 | SEQ ID No. 40 | SEQ ID No. 41 | SEQ ID No. 42 |
| P33426 | Q9YLR2 | Q0QC51 | Q69411 | A0A024D9U6 | A0A024D9R2 |
| SEQ ID No. 43 | SEQ ID No. 44 | SEQ ID No. 45 | SEQ ID No. 46 | SEQ ID No. 47 | SEQ ID No. 48 |
| Q8V729 | | | | | |
| SEQ ID No. 49 | | | | | |

| Fragments 408-674 | | | | | |
|---|---|---|---|---|---|
| Q8JJN2 | Q80IR5 | Q806D7 | Q6BD83 | Q6BD78 | B6VC89 |
| SEQ ID No. 28 | SEQ ID No. 29 | SEQ ID No. 30 | SEQ ID No. 31 | SEQ ID No. 32 | SEQ ID No. 33 |
| Q6PMR3 | | | | | |
| SEQ ID No. 34 | | | | | |

Fragment 406-672
Q9IVZ8
SEQ ID No. 35
Fragment 405-671
Q8JJM1
SEQ ID No. 36
Fragment 405-668
Q2PYP3
SEQ ID No. 37
Fragment 393-659
Q03500
SEQ ID No. 50

FIG. 1 also shows that, if the amino acid sequence 394-660 of the Q81871 variant is taken as reference sequence (SEQ ID No. 26) for all the proteins of 660 amino acids, the amino acid sequences 394-660 of the other variants (SEQ ID Nos. 38 to 49) have between 90.64% and 99.25% identity with the sequence SEQ ID No. 26, while if the total sequence of the protein of 660 amino acids of this same variant (SEQ ID No. 11) is taken, the sequences of 660 amino acids of the other variants (SEQ ID Nos. 12 to 23) have between 90.45% and 99.09% identity with this sequence SEQ ID No. 11.

Likewise, if the amino acid sequence 408-674 of the variant Q8JJN2 is taken as reference sequence (SEQ ID No. 28) for all the proteins of 674 amino acids, the amino acid sequences 408-674 of the other variants (SEQ ID Nos. 29 to 34) have between 98.50% and 98.88% identity with the sequence SEQ ID No. 28, while if the total sequence of the protein of 674 acids of this same variant is taken (SEQ ID No. 1), the sequences of 674 amino acids of the other variants (SEQ ID Nos. 2 to 7) have between 98.22% and 98.37% identity with this sequence SEQ ID No. 1.

More globally, if the amino acid sequence 394-660 of the Q81871 variant is taken as reference sequence (SEQ ID No. 26), the corresponding amino acid sequences of the other variants (SEQ ID Nos. 28 to 50) have between 90.64% and 99.25% identity with the sequence SEQ ID No. 26, therefore at least 90% identity, while if the total sequence of the protein of 660 amino acids of this same variant (SEQ ID No. 11) is taken, the total sequences of the proteins of the other variants (SEQ ID Nos. 1 to 10 and 12 to 24) have between 89.97% and 99.09% identity with this sequence SEQ ID No. 11, therefore at least 89% identity.

The percentage identity between 2 sequences is calculated from the alignment of the multiple sequences. The Clustal Omega program accessible in a more parameterizable version on the EMBL-EMI website (http://www.ebi.ac.uk/Tools/msa/clustalo/) generates an alignment score at the same time as the multiple alignment. This score is connected to the degrees of similarity between 2 compared sequences, for all the sequences, as illustrated in FIG. 1.

As shown in FIG. 1K, the 3 cysteines to be mutated are in a sequence of 12 amino acids which is defined as follows: $CPECRX_1LGX_2QGC$ (SEQ ID No. 25), in which $X_1$ represents P, T, S or A and $X_2$ represents L or F.

The mutations at the three cysteines above are carried out by substitution of said cysteines with any amino acid other than the cysteine well known to those skilled in the art, for instance the proteinogenic amino acids histidine, isoleucine, leucine, lysine, methionine, phenylalanine, threonine, tryptophan, valine, alanine, arginine, aspartic acid, asparagine, glutamic acid, glutamine, glycine, proline, serine and tyrosine.

However, it is preferable to select the substitution amino acid according to the following two criteria:
1) the "size or volume" of the amino acid side chain by relying on the representations of the maps of electron density obtained by X-ray diffraction, as for example shown in FIG. 2 giving such a representation, calculated at a resolution of 1.5 Angstrom, and derived from the website (printing of Nov. 13, 2013): http://people.mbi.ucla.edu/sawaya/m230d/Modelbuilding/modelbuilding.html
Indeed, on the basis of these maps, the amino acids of which the electron density is the most similar to that of cysteine (for example serine, valine and threonine) or amino acids "smaller" than cysteine (for example glycine, alanine) are selected. The amino acids that are too "big" (for example lysine, histidine, phenylalanine, tyrosine, arginine and tryptophan) are preferably discarded.
2) The possible reactivities. It is not desirable for the substituted amino acid to easily react with other surrounding amino acids. The charged amino acids such as basic amino acids (already excluded with the $1^{st}$ criterion) and acidic amino acids are preferably discarded.

According to one embodiment, the mutations in the polypeptides of the invention are carried out by replacing the three cysteines with any amino acid with the exception of proline, amino acids of which the side chains are charged, such as lysine, arginine, histidine, aspartic acid or glutamic acid, and amino acids of which the side chains comprise an aromatic benzene ring, such as tyrosine, phenylalanine or tryptophan.

Preferably, the mutations in the polypeptides of the invention are carried out by replacing the three cysteines with an amino acid chosen from alanine, glycine, threonine, valine and serine.

The 3 cysteines can be substituted with the same amino acid or with different amino acids, preferably according to the criteria above.

According to another embodiment, the mutations carried out consist in substituting the 3 cysteines with the same amino acid and preferably with serine.

The polypeptides of the invention comprise at least the amino acid sequence 394-660, numbered in relation to a p-ORF2 protein of 660 amino acids, and for a p-ORF2 protein of different length, they comprise at least the amino acid sequence corresponding to amino acids 394-660 of the p-ORF2 protein of 660 amino acids, said sequences being mutated as previously indicated.

The expression "polypeptide derived from the p-ORF2 protein of the hepatitis E virus" is intended to mean a continuous series of amino acids at positions 394-660 or equivalent positions, derived from the p-ORF2 protein of the hepatitis E virus. Reference is also made, without distinction, to polypeptide derived from the p-ORF2 protein, polypeptide of the p-ORF2 protein, p-ORF2 polypeptide, mutated p-ORF2 polypeptide, protein derived from the p-ORF2 protein, protein resulting from the p-ORF2 protein or mutated p-ORF2 protein.

The expression "comprises at least the sequence" is intended to mean that the polypeptide has said continuous series of amino acids derived from the p-ORF2 protein, or else it has this series of amino acids to which may be added:
(i) one or more amino acids belonging to the p-ORF2 protein, which are located before said sequence, and/or
(ii) one or more amino acids which do not belong to the p-ORF2 protein, such as a polyhistidine tail, a polysine tail, or a fusion protein, for example GST (Glutathione S Transferase), MBP (Maltose Binding Protein), CBP (Calmodulin Binding Peptide), CBD (Chitin Binding Domain), protein A, thioredoxin, and/or
(iii) a labeling, for example (a) by coupling to a label molecule known to those skilled in the art, such as biotin, an enzyme, a fluorescent label, a radioactive molecule or any other label as defined below, or (b) by phosphorylation.

Thus, according to one embodiment, the polypeptides of the invention comprise one or more of the following characteristics:
they consist of the polypeptides of amino acid sequence 394-660, numbered in relation to a p-ORF2 protein of 660 amino acids, in which the three cysteines at positions 627, 630 and 638 have been mutated or, for a p-ORF2 protein of different length, of amino acid sequence corresponding to amino acids 394-660 of the p-ORF2 protein of 660 amino acids, in which the three cysteines located at the three positions corresponding to positions 627, 630 and 638 of the p-ORF2 protein of 660 amino acids have been mutated;
they comprise one or more amino acids which do not belong to the p-ORF2 protein;
they are labeled, for example as illustrated above.

The polypeptides of the invention can be produced by techniques well known to those skilled in the art. For example, the polypeptides of the invention can be obtained by genetic engineering using steps, conventionally known to those skilled in the art, consisting in:
providing the DNA coding the polypeptides of the invention,
inserting this DNA by cloning into an expression vector such as a plasmid, a cosmid, a λ phage or a viral vector (baculovirus (*Autographa californica* Nuclear Polyhedrosis Virus), vaccinia virus, Semliki forest virus, adenovirus, lentivirus, etc.), which vector also comprises an origin of replication (for plasmids or cosmids) or a replication system which allows its amplification in the host cell and one or more promoters which allow the transcription of RNA messengers which will be translated into proteins, introducing the vector for expression into a host cell, such as a prokaryotic cell (for example bacterium such as *Escherichia coli, Bacillus subtilis*) by transformation or infection, or a eukaryotic cell (for example yeasts (*Saccharomyces cerevisiae, Pichia pastoris*), insect cells (Sf9, Sf21, High5 cells), mammalian cells (CHO, 293, Per.C6, BHK-21, Vero, etc.) by transient or permanent transfection, or else viral infection, culturing and optionally multiplying the host cell containing the expression vector, optionally with amplification of the vector in the host cell, as required, inducing transcription and protein synthesis for the production of the recombinant polypeptides of the invention, and purifying in order to extract said polypeptides, for example by means of a polyhistidine tail. The polypeptides are then said to be recombinant.

Thus, a subject of the invention is also:

the isolated nucleic acids comprising nucleotide sequences encoding the polypeptides of the invention as previously defined or sequences complementary to said coding sequences;

the expression vectors comprising a nucleic acid sequence as defined above, the prokaryotic or eukaryotic host cells comprising a nucleotide sequence encoding the polypeptides of the invention as defined above or a sequence complementary to said coding sequence or an expression vector as defined above.

When the polypeptides of the invention comprise other components, such as labels of polypeptide nature or fusion proteins, as described above, the nucleic acid sequence encoding these components can also be inserted into the same reading frame in the vector in order to allow a fusion production.

The addition of non-protein labels to the polypeptides of the invention can be carried out by techniques known to those skilled in the art using —NH—OC— bonds formed from the —NH$_2$ and —COOR groups (R being for example an activated ester group) of the labels and of the polypeptides of the invention. Thus, for example, when the label is biotin, those skilled in the art may use commercial reagents, such as the EZ-Link® NHS-Biotin reagents (ThermoScientific No. 20217, 21336 and 21343), which comprise a —COO-activated ester group to be reacted with the —NH$_2$ group of the polypeptides according to the invention according to the supplier's recommendations.

As previously indicated, the polypeptides of the invention are particularly of use for determining the presence of an antibody response directed against the p-ORF2 protein of the hepatitis E virus.

The determination of the presence of an antibody response against the p-ORF2 protein of the hepatitis E virus in a biological sample from a subject, which may contain the antibodies of said response, can be carried out by immunoassay and comprises or consists of the following steps:

bringing said biological sample into contact with a polypeptide as defined previously, detecting a signal emitted by the binding between said polypeptide and said antibodies, if they are present, using a label capable of emitting a detectable signal, comparing the signal thus obtained with a reference signal S predetermined with two populations of controls, one having developed said antibodies and the other not having developed said antibodies, a signal lower than said reference signal S signifying that the sample does not contain said antibodies, and a signal higher than said reference signal S signifying that the sample contains said antibodies.

The subjects who may be infected with the HEV virus, in whom the determination of the presence of the antibody response or of the antibody titer is carried out, may be any subject and in particular:

subjects having acute hepatitis symptoms, for instance yellowness of the skin and of the eyes (jaundice), dark urine, discolored stools, extreme fatigue, nausea, vomiting, fever, abdominal pain or "influenza-like" syndrome. These symptoms may or may not be accompanied by elevated hepatic enzymes (ALAT/ASAT). These subjects may or may not have already tested positive for the HAV, HBV or HCV viruses;

asymptomatic subjects with elevated hepatic enzymes (ALAT/ASAT). These subjects may or may not have already tested positive for the HAV, HBV or HCV viruses;

individuals belonging to a population "at risk" either of the condition becoming chronic, or of a fulminant severe form, such as:

individuals who are immunodepressed for any reason, including subjects who have undergone a transplant, subjects receiving one or more immunomodulatory or immunosuppressive therapies, such as a chemotherapy, an anti-TNF alpha treatment or else a corticotherapy, subjects who have a co-infection with HIV, elderly individuals (immunosenescence), pregnant women, subjects having a chronic hepatopathy beforehand.

The subjects may be mammals, such as human beings, domestic animals (dogs, cats, horses, etc.) and farm animals (members of the ovine race, cattle, members of the goat family), preferably human beings.

By way of biological samples of the subjects which may contain the anti-hepatitis E virus p-ORF2 antibodies, mention may be made of biological fluids such as whole blood or derivatives thereof, for example serum or plasma, urine, saliva and effusions, and also stools. Blood or derivatives thereof is preferred, and also stools. These samples can be used as they are in the method of the invention or may have undergone a pretreatment according to methods known to those skilled in the art.

The expression "determining the antibody response directed against the p-ORF2 protein of the hepatitis E virus in the biological sample from a subject" is intended to mean determining the presence or absence of antibodies produced by the subject in the case of an infection with the HEV virus, these antibodies being directed against the p-ORF2 protein.

This determination is carried out by immunoassay, which is an assay widely known to those skilled in the art. Briefly, it consists in determining an analyte, in the present case the anti-p-ORF2 antibodies of the antibody response (also called humoral response), using at least one partner for binding to the analyte.

Of course, the prefix "immuno" in the term "immunoassay", for example, should not be considered in the present application as strictly indicating that the binding partner is necessarily a partner of immunological origin, such as an antibody or an antibody fragment. Indeed, as is well known to those skilled in the art, this term is more widely used to also denote tests and methods in which the binding partner is not a partner of immunological origin/nature but consists, for example, of a receptor for the analyte that it is desired to detect and/or quantify. The essential condition is that the binding partner in question is capable of binding to the analyte being sought, in the present case of antibody nature, preferably specifically. Thus, it is known practice to refer to the ELISA assay for assays which use binding partners that are non-immunological stricto sensu, more widely called "ligand binding assay", whereas the term "immuno" is included in the title in extenso corresponding to the acronym ELISA. In the interests of clarity and uniformity, the term "immuno" is used in the present application to denote any biological analysis using at least one binding partner suitable for binding to the analyte being sought and detecting and/or quantifying the latter, preferably specifically, even when said binding partner is not of immunological nature or origin in the strict sense.

The expression "partner for binding to the anti-p-ORF2 antibodies" is intended to mean any molecule capable of binding to these antibodies. By way of example of such binding partners, mention may be made of antigens such as the native or recombinant p-ORF2 protein, fragments of this protein, and in particular the polypeptides as described previously, antibodies such as anti-Ig antibodies, for example anti-total Igs for a given species, or else an anti-IgG or an anti-IgM depending on whether IgGs or IgMs are sought (using an anti-species IgG or anti-species IgM for the detection of IgG or IgM in this species), antibody analogs (molecules capable of mimicking antibodies) such as nanofitins, aptamers or else "DARPins", or any other molecule which is known to have an interaction with antibodies. The essential condition for carrying out the method for determining the presence of the antibody response according to the invention is the use, as binding partner, at least of the polypeptides of the invention as previously described.

The antibody binding partners are for example either polyclonal antibodies or monoclonal antibodies, the obtaining of which is widely known to those skilled in the art.

By way of example of antibody fragments, mention may be made of Fab, Fab' and F(ab')2 fragments and also scFv (single chain variable fragments) and dsFv (double-stranded variable fragments). These functional fragments can in particular be obtained by genetic engineering.

The nanofitin antibody analogs are small proteins which, like antibodies, are capable of binding to a biological target, thus making it possible to detect it, to capture it or quite simply to target it within an organism.

The aptamer antibody analogs are oligonucleotides, generally RNA or DNA, identified in libraries containing up to $10^{15}$ different sequences, by a combinatorial method of in vitro selection called SELEX for "Systematic Evolution of Ligands by Exponential Enrichment" (Ellington A D and Szostak J W., 1990). Most aptamers are RNA compounds, owing to the capacity of RNA to adopt varying complex structures, thereby making it possible to create, at its surface, cavities of varied geometries, making it possible to bind various ligands. They are biochemical tools of interest which which can be used in biotechnological, diagnostic or therapeutic applications. Their selectivity and their ligand-binding properties are comparable to those of antibodies.

The "DARPins" antibody analogs, DARPins standing for Designed Ankyrin Repeat ProteINS (Boersma Y L and Plütckthun A, 2011), are another class of proteins which make it possible to mimic antibodies and to be able to bind to target proteins with high affinity and high selectivity. They derive from the family of ankyrin proteins which are adapter proteins making it possible to bind the integral membrane proteins to the spectrin/actin network which constitutes the "backbone" of the cell plasma membrane. The ankyrin structure is based on the repetition of a motif of approximately 33 amino acids and the same is true for the DARPins. Each motif has a secondary structure of helix-turn-helix type. DARPins contain at least three, preferably four to five, repeat units and are obtained by screening combinatorial libraries.

The immunoassay consisting in determining the antibody response is a qualitative, semi-quantitative or quantitative assay widely known to those skilled in the art, which preferably uses two antibody-binding partners. One of the two partners can be coupled to a label so as to form a conjugate or a tracer. The other binding partner can be captured on a solid support. Reference is then made to capture partner for the latter and detection partner for the former.

The formats using two binding partners are sandwich formats well known to those skilled in the art, namely:
 a format commonly known as the double-antigen sandwich, using, in capture and in detection, two antigens, of identical or different nature, capable of being recognized by the antibody being sought, it being understood that at least one of the antigens is a polypeptide of the invention;
 a format commonly known as immunocapture, using, in capture, an antibody, an antibody fragment or an antibody analog, as previously described, and, in detection, a polypeptide of the invention; and
 a format commonly known as indirect sandwich, using, in capture, a polypeptide of the invention and, in detection, an antibody, an antibody fragment or an antibody analog.

Preferably, the capture partner is a polypeptide of the invention and the detection partner is an anti-human IgG or anti-human IgM antibody (indirect sandwich format).

The measured signal emitted during the immunoassay is then proportional to the amount of antibodies of the biological sample.

The term "label" is intended to mean in particular any molecule containing a group that reacts with a group of the binding partner, directly without chemical modification, or after chemical modification so as to include such a group, which molecule is capable of directly or indirectly generating a detectable signal. A nonlimiting list of these direct-detection labels consists of:
 enzymes which produce a signal that is detectable for example by colorimetry, fluorescence, luminescence, such as horseradish peroxidase, alkaline phosphatase, β-galactosidase or glucose-6-phosphate dehydrogenase,
 chromophores such as fluorescent, luminescent or dye compounds,
 radioactive molecules such as $^{32}P$, $^{35}S$ or $^{125}I$,
 fluorescent molecules such as Alexa or phycocyanins, and electrochemiluminescent salts such as acridinium-based or ruthenium-based organometallic derivatives.

Indirect detection systems can also be used, for instance ligands capable of reacting with an anti-ligand. The ligand then corresponds to the label for constituting, with the binding partner, the conjugate.

The ligand/anti-ligand pairings are well known to those skilled in the art, which is the case for example with the following pairings: biotin/streptavidin, hapten/antibody, antigen/antibody, peptide/antibody, sugar/lectin, polynucleotide/sequence complementary to the polynucleotide.

The anti-ligand can then be directly detectable using the direct detection labels previously described or can itself can be detectable by means of another ligand/anti-ligand pairing, and so on.

These indirect detection systems can, under certain conditions, result in an amplification of the signal. This signal amplification technique is well known to those skilled in the art, and reference may be made to the prior patent applications FR 2781802 or WO 95/08000 by the applicant.

These various labels can be coupled to the polypeptides of the invention as previously indicated.

Depending on the type of labeling used, those skilled in the art will add reagents which allow the visualization of the labeling or the emission of a signal that is detectable by any type of appropriate measurement device, for instance a spectrophotometer, a spectrofluorimeter, a densitometer, a luminometer or else a high-definition camera.

The immunoassay can also comprise other steps known to those skilled in the art, such as washing steps and incubation steps.

The immunoassay can be a single-step or two-step assay, as is widely known to those skilled in the art. Briefly, a one-step immunoassay comprises bringing the sample to be tested simultaneously into contact with the two binding partners, including the polypeptides of the invention as previously defined, whereas a two-step immunoassay comprises bringing the sample to be tested firstly into contact with the first binding partner, then bringing the analyte-first binding partner complex thus formed into contact with the second binding partner, one of the two binding partners being a polypeptide of the invention as previously defined.

The reference signal S used in the method according to the invention is a signal obtained beforehand with two populations of controls, one having developed an antibody response directed against the p-ORF2 protein following an infection with the HEV virus and the other not having developed such an antibody response. Such a determination is widely known to those skilled in the art. It consists in particular in carrying out an immunoassay identical to that implemented in the method of the invention, in biological samples from these two populations (of nature identical to the samples that will be used in the method for determining the presence of the antibody response in the subjects tested), and in determining the value of the test (signal) making it possible to distinguish between these two populations.

The detected signal, compared with the reference signal, used to know whether or not the sample contains the antibodies sought, can correspond to the signal as such emitted by the label, or else it can be converted into an index which is a detected signal/reference signal ratio. According to one simple example, for which no gray zone exists, if the reference index is fixed at "1", an index for the sample tested that is higher than "1" signifies that the sample contains said antibodies and an index that is lower than "1" signifies that the sample does not contain said antibodies.

Or course, all the definitions previously given with regard to the polypeptides apply to the method for determining the presence of an antibody response directed against the p-ORF2 protein of the hepatitis E virus described above.

The polypeptides of the invention can also be of use for determining the titer of antibodies directed against the p-ORF2 protein of the hepatitis E virus in a biological sample from a subject, which may contain said antibodies. This determination can be carried out by immunoassay and comprises or consists of the following steps:

bringing said biological sample into contact with a polypeptide as previously defined, detecting a signal emitted by the binding between said polypeptide and said antibodies, if they are present, using a label capable of emitting a detectable signal, converting the detected signal into an antibody titer.

Of course, once again, all the definitions previously given with regard to the polypeptides, and also those linked to the method for determining the presence of the antibody response, apply to the method for determining the antibody titer. The only difference consists of the result given, which is not a result of "yes"/"no" type following the comparison of the detected signal with a reference signal, but a result of concentration, or titer, or amount, type following the final step consisting in converting the detected signal into an antibody titer.

This step of converting the detected signal into an antibody titer is widely known to those skilled in the art. It consists in using a mathematical model pre-established on the basis of a standard range. This standard range will be obtained beforehand in a known manner. Briefly, the obtaining of a standard range consists in measuring the signal generated by increasing and known amounts or concentrations of the target antibody, in plotting the curve giving the signal as a function of the antibody titer and in finding a mathematical model with represents this relationship as accurately as possible. The mathematical model will be used to determine the unknown amounts, titers or concentrations of anti-p-ORF2 antibodies contained in the biological sample to be tested.

The antibodies sought in the biological sample from the subjects are of various natures: IgM, IgG, IgA, IgE, the antibodies of IgG and IgM type being preferred. It is possible to look for antibodies of the same nature, for example IgGs alone or IgMs alone, or else it is possible to search for antibodies of different nature in a combined manner, for example IgGs and IgMs simultaneously or all the types of anti-ORF2 immunoglobulins at the same time (total Ig).

Regardless of the nature of the antibodies sought, and preferably when they are IgGs or IgMs, the methods for determining the presence of the antibody response or the antibody titer as previously described are particularly of use for the treatment of subjects in connection with the hepatitis E virus infection.

The term "hepatitis E virus infection" is intended to mean a current infection, that is to say that the subject in whom the immunoassay is carried out is in the process of becoming infected, and a past infection, that is to say that the subject in whom the immunoassay is carried out no longer has any symptoms, but has been in previous contact either with the virus, or with a vaccine against the virus.

Thus, another subject of the invention relates to the use of a method as previously defined, for assisting with the in vitro diagnosis, for the in vitro diagnosis of a hepatitis E virus infection in a subject who may be infected, for therapeutic monitoring of a subject infected with the hepatitis E virus or for carrying out epidemiological studies of the seroprevalence of anti-HEV antibodies in a population or in a given geographic territory.

All these uses are well known to those skilled in the art, the only condition being that they are carried out with the methods previously described and therefore the polypeptides previously described.

When the antibodies sought are IgGs, the methods as previously defined are also particularly of use for determining whether a subject needs to be vaccinated or revaccinated against the hepatitis E virus, which constitutes another subject of the invention.

Specifically, for determining whether or not the subject needs to be vaccinated or revaccinated against HEV, the following steps can be carried out:

1. determining the titer of anti-HEV IgG antibodies in a biological sample, in particular in a sample of blood or blood derivative, according to a method as previously defined, in a healthy subject or preferably in patients at risk, such as those previously described,
2. comparing the response obtained with a threshold, such a threshold being determined beforehand according to the requirements in force,
3. if the response obtained is lower than the threshold, this signifies that the subject should be vaccinated or revaccinated,
4. if the response obtained is higher than the threshold, this signifies that it is not necessary to vaccinate or revaccinate the subject.

Of course, the characteristics previously described in the context of the methods for determining the presence of the antibody response or of the antibody titer apply to the uses made of these methods, for instance the polypeptides and their various lengths and mutations, the biological samples and the subjects involved.

For carrying out the methods of the invention, used in particular according to the uses described above, the polypeptides of the invention can be contained in kits.

Thus, another subject of the invention relates to the kits for determining, by immunoassay, the presence of the antibody response or of the titer of antibodies directed against the p-ORF2 protein of the hepatitis E virus in a subject who may have produced these antibodies, comprising a polypeptide as previously defined.

Once again, the characteristics previously described in the context of the polypeptides and methods of the invention apply to the kits of the invention.

According to one particular embodiment, the kits also comprise or contain at least one positive control. This positive control comprises a compound capable of binding to the binding partners employed during the use of the kit, the compound being present in a predetermined amount.

By way of nonlimiting examples of such compounds, mention may be made of natural anti-ORF2 immunoglobulins (in this case, the positive control may be an ORF2 seropositive biological sample), non-natural, for example humanized, anti-ORF2 immunoglobulins, or anti-ORF2 monoclonal antibodies, for example mouse monoclonal antibodies.

The kits can also contain all the compounds required for carrying out the reaction between the binding partner(s) and the target antibodies, such as washing buffers or reagents allowing the visualization of a labeling or the emission of a detectable signal.

The invention will be understood more clearly by means of the following examples which are given by way of nonlimiting illustration.

EXAMPLES

Example 1: Construction, Expression and Purification of Mutated and Non-Mutated 394-660 Fragments of the ORF2 Capsid Protein of the Hepatitis E Virus The ORF2 sequence expressed is that of the Human/China/HeBei/1987 isolate of the hepatitis E virus, which is of genotype 1 (Uniprot accession No. Q81871—see also FIG. 1—SEQ ID No. 11). For the reference construction (ORF2-REF), the sequence corresponding to ORF2 amino acids 394-660 (SEQ ID No. 26) was fused on the N-terminal side with a polyhistidine tag (8-his). For the construction according to the invention (ORF2-MUT), 3 non-conservative mutations (cysteine to serine) were carried out in the ORF2 394-660 fragment at the 3 cysteines at positions 627, 630 and 638 (SEQ ID No. 27). Like ORF2-REF, ORF2-MUT comprises an 8-his tag on the N-terminal side.

```
SEQ ID No. 26:
QLFYSRP VVSANGEPTV KLYTSVENAQ QDKGIAIPHD

IDLGESRVVI QDYDNQHEQD RPTPSPAPSR PFSVLRANDV

LWLSLTAAEY DQSTYGSSTG PVYVSDSVTL VNVATGAQAV

ARSLDWTKVT LDGRPLSTTQ QYSKTFFVLP LRGKLSFWEA

GTTKAGYPYN YNTTASDQLL VENAAGHRVA ISTYTTSLGA

GPVSISAVAV LAPHSALALL EDTMDYPARA HTFDDFCPEC

RPLGLQGCAF QSTVAELQRL KMKVGKTREL

SEQ ID No. 27:
QLFYSRP VVSANGEPTV KLYTSVENAQ QDKGIAIPHD

IDLGESRVVI QDYDNQHEQD RPTPSPAPSR PFSVLRANDV

LWLSLTAAEY DQSTYGSSTG PVYVSDSVTL VNVATGAQAV

ARSLDWTKVT LDGRPLSTTQ QYSKTFFVLP LRGKLSFWEA

GTTKAGYPYN YNTTASDQLL VENAAGHRVA ISTYTTSLGA

GPVSISAVAV LAPHSALALL EDTMDYPARA HTFDDFSPES

RPLGLQGSAF QSTVAELQRL KMKVGKTREL
```

The DNA fragments corresponding to the ORF2-REF and ORF2-MUT constructs were obtained in the form of synthetic genes from the company GeneArt® (Life Technologies). They were cloned, between the Nco I (5') and Bam HI (3') sites, into the pET3d vector (Novagen, EMD Millipore) under the control of the IPTG (isopropyl beta-D-1-thiogalactopyranoside)-inducible T7 promoter. The plasmids obtained were verified by sequencing at the level of the inserts in order to be sure that they did not contain errors.

The expression plasmids are introduced into E. coli BL21 DE3 bacteria (Stratagene, Agilent Technologies) by heat-shock transformation. After isolation of the colonies on a Petri dish of LB-agar containing ampicillin, one colony corresponding to ORF2-REF and one corresponding to ORF2-MUT were removed and inoculated into 200 ml of 2×YT culture medium containing 0.5% glucose, in the presence of 100 µg/ml of ampicillin, overnight at 37° C., with stirring at 250 rpm. A volume of 16 ml of each preculture is used to inoculate 400 ml of 2×YT-0.5% glucose-100 µg/ml of ampicillin medium. These cultures are incubated at 37° C. with stirring at 250 rpm. When the optical density (OD) measured at 600 nm reaches approximately 1 OD unit, the protein expression is induced by adding 1 mM of IPTG. The growth of the cultures is monitored by measuring the optical density at regular intervals. After approximately 3 h of incubation, when the cultures reach the stationary phase, the cultures are stopped and the bacteria are collected by centrifugation (5000 g, 20 min, +2/8° C.). The bacterial pellets are weighed and then frozen at −80° C. until purification.

For the purification, the pellets (2 to 2.2 g) are taken up with 30 ml of lysis buffer (20 mM Tris HCl, 100 Mm NaCl, 5% glycerol, 5 U/ml Benzonase® Nuclease (Novagen), 0.48 g/l MgCl$_2$, EDTA-free complete protease inhibitors (Roche, Ref 045-66462) 1 chip/50 ml, pH 7.4). The bacteria are lysed by disintegration, using a Cell Disruption System (Constant Systems Ltd, Northants, United Kingdom), at 1600 bar while maintaining a refrigeration of the system at +2/8° C. The disintegrator is rinsed with an additional 30 ml of lysis buffer in order to recover all of the lysate. The lysates are then centrifuged at 10 000 g, 40 min, +2/8° C. and the pellets are recovered.

In order to dissolve the inclusion bodies, each pellet is taken up with 30 ml of a 20 mM Tris HCl buffer containing 100 mM NaCl, 5% glycerol and 5M urea, pH 7.4, and stirred for 1 h 30 at +18/25° C. The supernatants are recovered by centrifugation at 10 000 g, 20 min, ambient temperature, then successively filtered through 1.2 µm and 0.8 µm nitrocellulose filters.

The ORF2-REF and ORF2-MUT proteins are purified by single-step metal chelate affinity chromatography, by means of their polyhistidine tags. The purification is carried out on an automated system of ÄKTA type (GE Healthcare Lifesciences). The supernatant obtained after centrifugation is loaded onto a column of Ni-NTA resin (Roche, Ref 058-93682001) equilibrated in 20 mM Tris HCl buffer containing 100 mM NaCl, 5% glycerol and 5M urea, pH 7.4 (equilibration buffer, identical to the dissolving buffer). The elution buffer is equilibration buffer containing 300 mM of imidazole and the pH of which has been readjusted to 7.4. A washing cycle is carried out with the equilibration buffer containing 40 mM of imidazole. The protein is then eluted by means of a plateau at 100% of elution buffer, that is to say 300 mM of imidazole. The purification fractions are analyzed on SDS-PAGE gel stained with Coomassie blue. This analysis makes it possible to verify the conducting of the purification method and the selection of the fractions containing the protein of interest.

The fractions selected are pooled and dialyzed in 40 mM Tris HCl buffer containing 250 mM NaCl, 10% mannitol, 0.4 M arginine and 2M urea, pH 7.4. Two successive dialyses are carried out at +18/25° C. against a volume of buffer 100 times greater than that of the sample. The proteins dialyzed are assayed for total protein by measuring the optical density at 280 nm, then stored at −80° C.

Example 2: Characterization by SDS-PAGE Analysis of the ORF2-REF and ORF2-MUT Proteins A first characterization of the purified ORF2-REF and ORF2-MUT proteins was carried out by SDS-PAGE analysis on a NuPAGE® Bis-Tris 4-12% gel in NuPAGE® MES SDS buffer (Life Technologies). Before loading onto the gel (10 µL/well), the proteins were diluted in a 4× NuPAGE® LDS Sample Buffer (Life Technologies) (3/1, volume/volume) and were subjected to various treatments. The reduction is carried out by adding 50 mM, final concentration, of dithiothreitol (DTT). The heating is for 10 min at 75° C. The combinations tested are the following:
HEATED and REDUCED (with DTT)
HEATED and NON-REDUCED (without DTT)
NON-HEATED and REDUCED (with DTT)
NON-HEATED and NON-REDUCED (without DTT).

A photograph of the SDS-PAGE gel stained with Coomassie blue in order to visualize total proteins is presented in FIG. 3. Reduced and heated (bands under the + and + columns in the table), the ORF2-REF and ORF2-MUT proteins have the same molecular weight, which is slightly higher than 30 kDa. This analysis condition makes it possible to visualize the monomeric form of the two proteins.

Under the non-reduced and heated condition (bands under the columns + for heated and − for reduced in the table), the ORF2-REF has 4 bands including a majority of apparent molecular weight less than 70 kDa. This band corresponds to a dimeric form of the ORF2-REF protein: the two monomers are linked by at least one covalent bond (disulfide bridge) which is not destroyed by heat denaturation and which requires the addition of a reducing agent. Under the same analysis conditions, the ORF2-MUT has a single band, it is therefore monomeric.

Under the non-heated condition, with or without the presence of reducing agent (band under the columns—for heated and respectively + or − for reduced in the table), the ORF2-REF has a complex migration signal with numerous bands, underlining the diversity of the interactions taking place between the monomers. The oligomeric form heterogeneity present in the ORF2-REF is clearly demonstrated in the line analyzed under the non-denaturing conditions, that is to say non-heated and non-reduced. The presence of at least 5 bands of high molecular weight is observed in addition to the bands which correspond to the covalent and non-covalent dimer. Conversely, the non-heated ORF2-MUT which is reduced or non-reduced (band under the columns—for heated and respectively + or − for reduced in the table), has a very simple migration profile, with a largely predominant band which corresponds to the non-covalent dimer. Traces of monomer and a band which migrates at approximately 80 kDa, which is very probably the non-covalent tetrameric form, are also noted.

Thus, the ORF2-MUT protein is clearly more homogeneous than the ORF2-REF protein and is essentially in the form of a non-covalent dimer. The ORF2-REF, which is very heterogeneous, contains at the same time covalent dimers (major form), non-covalent dimers and various high-molecular-weight forms.

Example 3: Characterization of the ORF2-REF and ORF2-MUT Proteins by Fluorescent Labeling of the Free Cysteines In order to refine the previous results, it was desired to determine, for each protein preparation, the proportion of free cysteines and of cysteines involved in disulfide bridges. The protein sample is divided into two: the first half undergoes a direct alkylation of the free thiols of the accessible cysteines; the second half undergoes an alkylation after reduction and heating, which treatment makes all the cysteines accessible.

The alkylation is carried out using the BODIPY® FL iodoacetamide fluorescent reagent (Life Technologies, Ref. D-6003) which has spectral characteristics very similar to fluorescein. The labeling is carried out according to the manufacturer's instructions. Very briefly, it is necessary to extemporaneously prepare a stock solution of BODIPY® FL iodoacetamide at 1 or 10 mM and to dilute the proteins to 100 µM. In the dark, the BODIPY® FL iodoacetamide is added dropwise to the protein solution to be labeled (10 to 20 mol of BODIPY® FL iodoacetamide per mole of protein) and the mixture is incubated for 30 to 60 min in the dark. The protein thus labeled is migrated on an SDS-PAGE gel in order to separate it from the excess fluorophore. The gel is then visualized on a fluorescence imaging system (Chemi-Doc™ XRS+, Bio-Rad) and the fluorescence intensity at the level of the protein band is measured. This fluorescence is specific and proportional to the number of cysteines labeled.

The analysis is carried out in relative amount while taking as reference the fluorescence intensity of the ORF2-REF monomer obtained after heating and reduction. In this molecule, there are 3 cysteines and in theory, under these conditions, all the cysteines are labeled (100% fluorescence) . The ORF2-MUT protein is not labeled with the BODIPY® FL iodoacetamide. Approximately 1% of fluorescence is detected for the ORF2-MUT protein; it is the nonspecific background noise. With regard to the ORF2-REF protein, there is no fluorescence detected in the non-heated, non-reduced sample. This indicates that no cysteine is accessible to the alkylating agent, which is in agreement with the profile observed in SDS-PAGE (FIG. 3). For the heated ORF2-REF sample, the monomer band corresponds to a fluorescence intensity of 5%, which indicates that 5% of the cysteines of ORF2-REF are not involved in disulfide bridges, but buried in the core of the protein and therefore non-accessible when the sample is not heated.

This analysis clearly makes it possible to confirm that the ORF2-REF protein is predominantly non-monomeric. Forming both covalent dimers and non-covalent dimers, the ORF2-REF protein is much more heterogeneous than the ORF2-MUT protein.

Example 4: Characterization of the ORF2-REF and ORF2-MUT Proteins by Size Exclusion Chromatography (SEC)

Size exclusion chromatography makes it possible to separate molecules according to their size. Each exclusion chromatography resin is characterized by a specific fractionation range, expressed in molecular weight, within which it is possible to separate the molecules. Molecules of which the size is below the lower limit of the fractionation range or above its upper limit are not efficiently fractionated. Molecules of which the size exceeds the exclusion limit, also expressed in molecular weight, are not fractionated and are eluted together in the dead volume of the column.

Size exclusion chromatography analyses were carried out on a Waters Alliance HPLC (high performance liquid chromatography) system with a Superdex 200 10/300 GL column (GE Healthcare) in PBS (phosphate buffered saline) buffer. The efficient fractionation range of the Superdex 200 resin is from 10 to 600 kDa and its exclusion limit is 1300 kDa. For each ORF2 protein, 100 μl of sample (approximately 175 μg) were injected at 0.5 ml/min. The detection was carried out by measuring the absorbance at 280 nm. The chromatograms obtained for each protein are presented in FIG. 4. The ORF2-REF chromatogram (FIG. 4A) shows 3 populations, one major population representing 86.9% of the forms observed and two additional populations, corresponding to 8.5% and 4.2% of the forms observed, eluting slightly before and slightly after the major peak, respectively. On the other hand, on the ORF2-MUT chromatogram (FIG. 4B), the presence of a single peak, representing 99.9% of the forms observed, is observed.

For each of the chromatograms, integration of the signal of absorbance at 280 nm at the level of the peaks makes it possible to determine the total amount of protein that was fractionated during the analysis. For the ORF2-REF protein, the sum of the areas under each of the 3 peaks is 6800 mU*dry. For the ORF2-MUT protein, the area under the single peak is 16 100 mU*dry. The amount of ORF2-REF fractionated during the analysis represents only 42% of the amount of ORF2-MUT fractionated (ratio of the areas), whereas, initially, the same amount of each of the proteins had been injected. It can be deduced therefrom that a large fraction of ORF2-REF did not enter the resin and is therefore in the form of precipitate retained at the column prefilter. The precipitation by aggregation is promoted because, unlike the SDS-PAGE electrophoresis, no reagent of the SEC chromatography analysis contains SDS or another detergent that could contribute to dissolving the proteins.

In conclusion, the size exclusion chromatography analysis made it possible to confirm by means of an independent technique that the ORF2-MUT protein (1 form observed) is much more homogeneous than the ORF2-REF protein (3 forms observed). Under the conditions of the analysis, a large part of the ORF2-REF protein is in the form of precipitate and cannot therefore be studied. Moreover, it cannot be excluded that a similar precipitation phenomenon or else a self-assembly phenomenon also occurs for the ORF2-MUT protein and that at least a part thereof could not be analyzed. In order to supplement the SEC analysis and to be able to demonstrate more definitely that the ORF2-MUT protein does not contain aggregates, it is necessary to use an alternative biophysical characterization technique which makes it possible to perform analyses on a very wide range of molecular sizes.

Example 5: Characterization of the ORF2-REF and ORF2-MUT Proteins by the AsFlFFF-MALS (Asymmetric Flow Field Flow Fractionation-Multi-Angle Light Scattering) Technique In order to be able to study the state of aggregation of the ORF2-REF and ORF2-MUT proteins under native conditions, a technique was carried out which enables the separation of a wide range of molecules of from 5 kDa to 10 μm. The technique is asymmetric flow field flow fractionation (AsFlFFF or AF4) coupled to multi-angle light scattering (MALS). The macromolecules are separated according to their scattering coefficient, under the effect of cross flows, without any stationary phase and under native conditions. The absence of stationary phase is a considerable advantage since the latter can interact with one or some of the molecular species that it is sought to separate and thus bias the analysis.

The AsFlFFF-MALS analysis was carried out by the "Biological and Technological Qualities of Plant Raw Materials" team of the INP of Toulouse (Ecole d'ingénieurs [Graduate Engineering School] Purpan, Toulouse). The experimental conditions of the analysis as carried out are the following:

| | |
|---|---|
| HPLC | Ultimate 3000 Dionex |
| AsFlFFF | Eclipse 2 Wyatt |
| MALS | Heleos II Wyatt (633 nm) |
| Eluent | 1x PBS + 500 mM of NaCl |
| Sample volume injected | 30 μL and 60 μL |
| AsFlFFF cell | Small |
| Membrane | RC 5 kDa |
| Spacer | 350 μm W |
| Linear flow | 1 ml/min |
| Cross flow | 3 to 0.1 |
| Injection flow rate | 0.2 ml/min |
| Detectors | UV 280 nm_1A |
| Data processing parameters | MALS: Model Zimm |
| | dn/dc 0.185 ml/g |
| | UV extinction: 1246 ml/(g cm) |

The profile of the fractogram obtained for the ORF2-REF protein is not presented since the analysis is difficult to interpret. This is because a first peak overloads the entire MALS signal of the analysis, making the molecular weight estimations imprecise and unreliable. However, it is possible to conclude that very large aggregates, the size of which is estimated at $10^5$-$10^6$ kDa, are present.

The profiles of fractograms obtained for the UV (thin solid line) and MALS (hatched line) signals of the ORF2-MUT protein are given in FIG. 5. A major peak with a shoulder which elutes from 9 to 15 minutes is observed under UV (thin solid line). The bimodal nature of this peak, suggested under UV, appears very clearly in MALS (hatched line). In the latter, a first population of molar mass estimated at approximately 70 kDa (75% of the sample, elution between 9.2 and 11.7 min) and a second population of molar mass estimated at approximately 356 kDa (25% of the sample, elution between 11.7 and 15.0 min) are present. For a monomer of the ORF2-MUT protein, the theoretical molar mass calculated from its sequence is 31 kDa. This theoretical calculation was confirmed experimentally during the SDS-PAGE analysis presented in Example 2. Thus, the observed molar mass of approximately 70 kDa corresponds to a dimer, and that of 356 kDa corresponds to a dodecamer (12-mer) of ORF2-MUT. Finally, and contrary to ORF2-REF, ORF2-MUT does not contain large detectable aggregates which elute in steric mode at the beginning of the fractogram.

In conclusion, the AsFlFFF-MALS analysis, which is a sophisticated method enabling a characterization of the molecular species under native conditions, without any interactions with a stationary phase, makes it possible to show that the ORF2-MUT protein i) is a mixture of 75% of non-covalent dimers and 25% of non-covalent dodecamers, ii) contains no aggregates in the native state, and iii) is much more homogeneous than ORF2-REF. The heterogeneity of the molecular species in the ORF2-REF protein is so great that even a technique as sophisticated and resolutive as AsFlFFF-MALS does not make it possible to reliably characterize the distribution of the various forms.

Example 6: Comparison of the Immunological Reactivities of the ORF2-REF and ORF2-MUT Antigens and of the Diagnostic Performance Levels of the Immunoassays Using these Antigens for the Detection of Anti-ORF2 IgMs The antigenicity of the ORF2-REF and ORF2-MUT proteins was compared by immunoassay using the VIDAS® automated immunoanalysis device (bioMérieux). The single-use tip serves both as a solid phase for the reaction and as a pipetting system. The cartridge is composed of 10 wells (X0 to X9) covered with a sealed and labeled aluminum foil. The first well (X0) comprises a precut part for facilitating the introduction of the sample. The final well (X9) is an optical cuvette in which the fluorescence of the substrate is measured. The various reagents required for the analysis are contained in the intermediate wells (X1 to X8). All the steps of the test are carried out automatically by the instrument. They consist of a succession of cycles of suction/delivery of the reaction medium.

a) Sensitization and Passivation of the Tips (Coating)

The tips were sensitized with 300 μL of a solution of ORF2-REF or ORF2-MUT at 2 μg/ml in a 77 mM carbonate buffer, pH 9.2. After approximately 20 h of incubation at +18/25° C. with the sensitizing solution, the tips are emptied. 300 μL of a solution of 200 mM Tris containing 5 g/L of bovine albumin are then added. The passivation continues at +18/25° C. overnight. The tips are emptied, dried, and then stored at +4° C. protected from moisture, until use.

b) Immunoassay Procedure

The VIDAS® automated device mixes 600 μL of sample diluent containing 20 mM Tris, pH 7.4, 300 mM NaCl and 5 g/l of serum albumin with 38.3 μl of the sample of serum or of plasma to be tested. As soon as the VIDAS® tip is in contact with the sample, the first step of the immunological reaction begins. This step enables the specific binding of the anti-ORF2 IgMs, which may or may not be present in the serum or plasma sample, to the ORF2 protein adsorbed onto the tip. After 4 minutes of incubation at 37° C., the unbound components are removed by washing with a 200 mM Tris buffer, pH 9 containing 300 mM NaCl and 0.275% Triton X-100. During the second step, the tip is incubated with a solution of conjugate containing approximately 60 ng/mL of an anti-human IgM mouse IgG (bioMérieux), coupled to alkaline phosphatase, in a 10 mM phosphate buffer containing 300 mM of NaCl and 5 g/l of bovine serum albumin. The X5 well contains 400 μl of this solution that the tip suctions/delivers for 5 minutes, still at 37° C. The second step leads to the formation of a complex between the anti-ORF2 IgMs present in the sample and the alkaline phosphatase-coupled anti-IgM conjugate. This step is followed by 2 successive washes in order to remove the unbound compounds.

During the final revealing step, the 4-methylumbelliferyl phosphate substrate is suctioned and then delivered in the tip; the alkaline phosphatase of the conjugate catalyzes the reaction for hydrolysis of this substrate to 4-methylumbelliferone, the emitted fluorescence of which is measured at 450 nm. The value of the fluorescence signal (RFV=relative fluorescence value) is proportional to the concentration of the anti-ORF2 IgMs present in the sample.

The immunoassay procedure for the detection of the anti-ORF2 IgMs was carried out in 18 HEV-positive IgM samples and 21 HEV-negative IgM samples. These samples, serums or plasmas, were mainly obtained via the Etablissements Francais du Sang (EFS) [French Blood Bank] and were characterized beforehand by using various commercial tests: Wantai HEV-IgM ELISA (Ref. WE-7196), recomWell HEV IgM (Ref. 5005, Mikrogen Diagnostik) or EIAgen HEV IgM kit (Ref. 071050 Adaltis). The REV-positive IgM status of the samples was thus defined if the sample was positive at least in one of the tests mentioned above. The "HEV-negative" samples are for their part negative in all of the commercial techniques used.

Immunoreactivity.

At equal amounts, the ORF2-MUT protein has an antigenic reactivity that is much higher than that of the ORF2-REF protein. This superiority is very statistically significant (P<0.0001, one-sided paired Wilcoxon test) and is illustrated in FIG. 6 which represents the distributions of the RFV signals obtained by the IgM immunoassays using either the ORF2-REF antigen (subsequently referred to as ORF2-REF IgM test), or the ORF2-MUT antigen (subsequently referred to as ORF2-MUT IgM test), on HEV-positive samples (Table 1) and HEV-negative samples (Table 2). For all the positive samples, the RFV signals obtained with the ORF2-MUT antigen are higher than those obtained with the ORF2-

REF antigen. For the samples 155797, 154183, 154053 and 154050, the gain in RFV, very significantly, reaches approximately 1000 RFV. Furthermore, the RFV signals obtained on the REV-negative samples by the ORF2-REF and ORF2-MUT IgM tests are comparable and remain very low (FIG. 6).

Diagnostic Sensitivity.

On the panel of positive samples analyzed, presented in Table 1, the ORF2-REF IgM test, according to the prior art, exhibits two false negatives (samples 155118 and 136997), which corresponds to a sensitivity of only 88.9%, whereas the ORF2-MUT IgM test has no false negative, which results in an increased sensitivity at 100%.

Furthermore, the panel analyzed was tested beforehand using the Wantai test in order to be able to identify samples for which said test is negative, but which were confirmed positive by two other IgM kits. The objective of this selection was to demonstrate the advantages of the polypeptides 394-660 of the invention. The Wantai IgM kit is the only commercial IgM kit comprising only an ORF2 antigen, called pE2, therefore directly comparable to an IgM immunoassay using ORF2-REF or else ORF2-MUT. However, unlike the polypeptides 394-660, the sequence of the pE2 antigen does not comprise the C-terminal epitope (aa 613-654). On the panel of positive samples tested, the Wantai test exhibits 6 false negatives, that is to say a sensitivity of only 66.6%. Among these samples, 4/6 are detected as positive by the ORF2-REF IgM test, illustrating the diagnostic advantage of the C-terminal epitope, and especially 6/6 are detected by the ORF2-MUT IgM test, illustrating once again the superiority of this polypeptide, and also its contribution to the improved sensitivity of an immunoassay.

Diagnostic Specificity.

On the panel of negative samples analyzed (Table 2), the ORF2-REF IgM test exhibits two false positives (samples 129534 and 137163), which corresponds to a specificity of only 88.9%, whereas the ORF2-MUT IgM test has no false positive, which is reflected by an increased specificity at 100%.

It should be noted that the improved sensitivity of the ORF2-MUT IgM test does not occur to the detriment of its specificity.

TABLE 2

Search for anti-ORF2 IgMs in the sera of patients with a definite hepatitis E infection. Specificity study on confirmed negative samples

| Sample Identifier | VIDAS ORF2-REF IgM immunoassay (Neg if RFV < 70) | | VIDAS ORF2-MUT IgM immunoassay (Neg if RFV < 70) | |
| --- | --- | --- | --- | --- |
| | Signal (RFV) | Interpretation | Signal (RFV) | Interpretation |
| 34848 | 27 | Neg | 17 | Neg |
| 39418 | 39 | Neg | 39 | Neg |
| 40880 | 13 | Neg | 14 | Neg |
| 123933 | 33 | Neg | 24 | Neg |
| 129534 | 89 | Pos | 48 | Neg |
| 129624 | 30 | Neg | 44 | Neg |
| 134067 | 25 | Neg | 18 | Neg |
| 134700 | 48 | Neg | 50 | Neg |
| 134733 | 44 | Neg | 55 | Neg |
| 59091077237 | 67 | Neg | 54 | Neg |
| 134718 | 36 | Neg | 34 | Neg |
| 137163 | 82 | Pos | 54 | Neg |
| 141316 | 48 | Neg | 40 | Neg |
| 144810 | 50 | Neg | 49 | Neg |
| 144098 | 59 | Neg | 45 | Neg |
| 155122 | 41 | Neg | 61 | Neg |
| 34678 | 20 | Neg | 13 | Neg |

TABLE 1

Search for anti-ORF2 IgMs in the sera of patients with a definite acute hepatitis E infection. Sensitivity study on confirmed positive samples

| Sample Identifier | Wantai Test (Pos if Index >=1) | | VIDAS ORF2-REF IgM immunoassay (Pos if RFV >=70) | | VIDAS ORF2-MUT IgM immunoassay (Pos if RFV >=70) | |
| --- | --- | --- | --- | --- | --- | --- |
| | Index | Interpretation | Signal (RFV) | Interpretation | Signal (RFV) | Interpretation |
| 155118 | 0.0 | Neg | 50 | Neg | 76 | Pos |
| 136997 | 0.5 | Neg | 64 | Neg | 122 | Pos |
| 123971 | 0.5 | Neg | 98 | Pos | 145 | Pos |
| 143289 | 0.4 | Neg | 115 | Pos | 159 | Pos |
| 136360 | 1.5 | Pos | 156 | Pos | 225 | Pos |
| 130162 | 2.2 | Pos | 209 | Pos | 236 | Pos |
| 144054 | 0.0 | Neg | 217 | Pos | 252 | Pos |
| 39417 | 0.4 | Neg | 291 | Pos | 536 | Pos |
| 9264883 | 7.5 | Pos | 646 | Pos | 785 | Pos |
| 9264884 | 5.7 | Pos | 753 | Pos | 1014 | Pos |
| 155798 | 4.6 | Pos | 821 | Pos | 1025 | Pos |
| 155795 | 5.6 | Pos | 484 | Pos | 1072 | Pos |
| 155799 | 8.3 | Pos | 934 | Pos | 1191 | Pos |
| 155797 | 3.5 | Pos | 394 | Pos | 1737 | Pos |
| 154183 | 1.8 | Pos | 843 | Pos | 1820 | Pos |
| 154050 | 10.1 | Pos | 1596 | Pos | 2705 | Pos |
| 155796 | 8.5 | Pos | 2237 | Pos | 2916 | Pos |
| 154053 | 13.6 | Pos | 3200 | Pos | 4503 | Pos |

Neg = Negative and
Pos = Positive

TABLE 2-continued

Search for anti-ORF2 IgMs in the sera of patients with a definite hepatitis E infection. Specificity study on confirmed negative samples

| Sample Identifier | VIDAS ORF2-REF IgM immunoassay (Neg if RFV < 70) | | VIDAS ORF2-MUT IgM immunoassay (Neg if RFV < 70) | |
|---|---|---|---|---|
| | Signal (RFV) | Interpretation | Signal (RFV) | Interpretation |
| 34745 | 15 | Neg | 10 | Neg |
| 35049 | 17 | Neg | 14 | Neg |
| 39321 | 8 | Neg | 7 | Neg |
| 40879 | 15 | Neg | 10 | Neg |

In conclusion, the ORF2-MUT antigen exhibits a better immunoreactivity than the ORF2-REF antigen, which results in better diagnostic performance levels in terms of both sensitivity and specificity. This better immunoreactivity of the ORF2-MUT protein could be explained by a better presentation of the immunodominant conformational epitopes due to its more homogeneous and more oligomeric structure, as shown in Example 2 (more non-covalent dimers) and in Example 5 (formation of dodecamers), which would allow it to exhibit, overall, an antigenic structure that is much closer to that of the viral particle.

Example 7: Reproducibility of the Tests for Detecting Anti-Hepatitis E Virus IgMs Using ORF2-REF or ORF2-MUT The same positive sample was assayed in duplicate, in two different series, 3 days in a row, using the ORF2-REF IgM test and the ORF2-MUT IgM test according to the procedure described in Example 6. The results are presented in Table 3. The coefficient of variation (CV) is the ratio of the standard deviation to the mean and allows the comparison of distributions of values of which the measurement scales are not comparable. The lower the value of the coefficient of variation, the smaller the dispersion around the mean, and therefore the more reproducible the measurement. The coefficient of variation is 5.4% for the ORF2-REF IgM test and 2.1% for the ORF2-MUT IgM test. The two immunoassays are clearly reproducible; the ORF2-MUT IgM test appears to be better.

TABLE 3

Reproducibility of the tests for detecting anti-ORF2 IgMs using the ORF2-REF or ORF2-MUT protein.

| | RFV Signal | |
|---|---|---|
| | ORF2-REF IgM | ORF2-MUT IgM |
| Day 1 - Series 1 | 274 | 566 |
| Day 1 - Series 1 | 293 | 552 |
| Day 1 - Series 2 | 289 | 577 |
| Day 1 - Series 2 | 296 | 589 |
| Day 2 - Series 1 | 307 | 554 |
| Day 2 - Series 1 | 287 | 563 |
| Day 2 - Series 2 | 269 | 547 |
| Day 2 - Series 2 | 273 | 559 |
| Day 3 - Series 1 | 297 | 573 |
| Day 3 - Series 1 | 309 | 560 |
| Day 3 - Series 2 | 265 | 553 |
| Day 3 - Series 2 | 267 | 563 |
| Mean | 286 | 563 |
| Total % CV | 5.4% | 2.1% |

In order to be able to determine whether the difference observed between the 2 CVs is statistically significant, the uncertainty of each of them is estimated. Accepting a risk of $\alpha=0.05$ (confidence interval CI at 95%) and assuming that the risk is distributed symmetrically and bilaterally (i.e. as much risk that the CV is overestimated as that it is underestimated), the upper limit CV is deduced therefrom by applying the following formula:

$$CV_{upper\ limit} = \sqrt{Chi^2(0.025, ddl) \div \sqrt{ddl}} \times CV$$

$Chi^2$ (0.025, ddl) is the value of the $Chi^2$ law for a risk of 0.025 (half of $\alpha=0.05$) and a given degree of freedom (ddl). For the series presented, the number of repetitions is n=12 and ddl=n−1, i.e. 11. The $Chi^2$ law value (0.025, 11) is 21.92. The upper limit of the 95% CI of the CV is given by the formula. The lower limit of the 95% CI is deduced by subtracting from the CV observed the difference between the upper limit and the CV observed. The following estimations are thus obtained:

| | CV observed | CV upper limit | CV lower limit |
|---|---|---|---|
| ORF2-REF | 5.4% | 7.7% | 3.2% |
| ORF2-MUT | 2.1% | 3.0% | 1.3% |

According to these calculations, the CV of the ORF2-REF IgM test can be between 3.2% and 7.7% and that of the ORF2-MUT IgM test can be between 1.3% and 3.0%. The two intervals do not overlap, and the two CVs observed, of 5.4% and 2.1%, are therefore significantly different.

Consequently, the ORF2-MUT IgM test is more reproducible than the ORF2-REF IgM test.

LITERATURE REFERENCES

Boersma Y L, Plückthun A, 2011, Curr. Opin. Biotechnol, 22: 849-857

Ellington A D and Szostak J W., 1990, Nature, 346: 818-822

Emerson, S. U., & Purcell, R. H., 2007, Hepatitis E Virus. In D. M. Knipe, P. M. Howley, D. E. Griffin, R. A. Lamb, M. A. Martin & B. a. S. Roizman S. E. (Eds.), Fields Virology (5th ed., pp. 3047-3058). Philadelphia, USA: Lippincott Williams & Wilkins Fields and Noble, 1990, Int J Pept Protein Res., 35:161-214

Meng J, et al., 2001, Virology, 288: 203-211

Merrifield 1963, J Am Chem Soc. 85:2149-2154

Riddell M. A., et al., 2000, Journal of Virology, 74(17): 8011-8017

The invention claimed is:

1. A polypeptide of the p-ORF2 protein of the hepatitis E virus, comprising at least the amino acid sequence 394-660, numbered in relation to a p-ORF2 protein of 660 amino acids, in which the three cysteines at positions 627, 630 and 638 have been mutated or, for a p-ORF2 protein of different length, at least the amino acid sequence corresponding to amino acids 394-660 of the p-ORF2 protein of 660 amino acids, in which the three cysteines located at the three positions corresponding to positions 627, 630 and 638 of the p-ORF2 protein of 660 amino acids have been mutated.

2. The polypeptide as claimed in claim 1, wherein the mutations are carried out by replacing the three cysteines with any amino acid with the exception of proline, amino acids of which the side chains are charged and amino acids of which the side chains comprise an aromatic benzene ring.

3. The polypeptide as claimed in claim 1, wherein the mutations are carried out by replacing the three cysteines with an amino acid chosen from alanine, glycine, threonine, valine and serine.

4. The polypeptide as claimed in claim 1, wherein the mutations consist in substituting the cysteines with the same amino acid.

5. The polypeptide as claimed in claim 4, wherein the mutations are carried out by replacing the three cysteines with serine.

6. The polypeptide as claimed in claim 1, wherein it consists of the polypeptide of amino acid sequence 394-660, numbered in relation to a p-ORF2 protein of 660 amino acids, in which the three cysteines at positions 627, 630 and 638 have been mutated or, for a p-ORF2 protein of different length, of amino acid sequence corresponding to amino acids 394-660 of the p-ORF2 protein of 660 amino acids, in which the three cysteines located at the three positions corresponding to positions 627, 630 and 638 of the p-ORF2 protein of 660 amino acids have been mutated.

7. The polypeptide as claimed in claim 1, wherein it also comprises one or more amino acids which do not belong to the p-ORF2 protein or in that it is labeled.

8. An isolated nucleic acid comprising a nucleotide sequence encoding the polypeptide as defined in claim 1 or a sequence complementary to the coding sequence.

9. An expression vector comprising a nucleic acid sequence as defined in claim 8.

10. A host cell comprising a nucleotide sequence encoding the polypeptide as defined in claim 1 or a sequence complementary to the coding sequence or an expression vector comprising a nucleic acid sequence encoding the polypeptide or a sequence complementary to the coding sequence.

11. A method for determining, by immunoassay, the presence of an antibody response directed against the p-ORF2 protein of the hepatitis E virus in a biological sample from a subject, which may contain the antibodies of the response, which method comprises the following steps:

bringing the biological sample into contact with a polypeptide as defined in claim 1, detecting a signal emitted by the binding between the polypeptide and the antibodies, if they are present, using a label capable of emitting a detectable signal, comparing the signal thus obtained with a reference signal S predetermined with two populations for controls, one having developed the antibodies and the other not having developed the antibodies, a signal lower than the reference signal S signifying that the sample does not contain the antibodies, and a signal higher than the reference signal S signifying that the sample contains the antibodies.

12. A method for determining, by immunoassay, the titer of antibodies directed against the p-ORF2 protein of the hepatitis E virus in a biological sample from a subject, which may contain the antibodies, which method comprises the following steps:

bringing the biological sample into contact with a polypeptide as defined in claim 1, detecting a signal emitted by the binding between the polypeptide and the antibodies, if they are present, using a label capable of emitting a detectable signal, converting the detected signal into an antibody titer.

13. The method as claimed in claim 11, wherein the antibodies which are sought are IgMs or IgGs.

14. The method as defined in claim 11 further comprising assisting with the in vitro diagnosis, the in vitro diagnosis of a hepatitis E virus infection in a subject who may be infected, therapeutic monitoring of a subject infected with the hepatitis E virus or carrying out epidemiological studies of the seroprevalence of anti-HEV antibodies in a population or in a given geographic territory.

15. The method as defined in claim 11 further comprising determining whether a subject needs to be vaccinated or revaccinated against the hepatitis E virus, in which the antibodies which are sought are IgGs.

16. A kit for determining, by immunoassay, the presence of the antibody response or the titer of antibodies directed against the p-ORF2 protein of the hepatitis E virus in a subject who may have produced these antibodies, comprising a polypeptide as defined in claim 1.

17. The kit as claimed in claim 16, also comprising at least one positive control sample which is a sample containing a given titer of antibodies directed against the p-ORF2 protein of the hepatitis E virus.

* * * * *